United States Patent [19]
Deretic et al.

[11] Patent Number: 6,083,691
[45] Date of Patent: *Jul. 4, 2000

[54] DETECTION OF CONVERSION TO MUCOIDY IN *PSEUDOMONAS AERUGINOSA* INFECTING CYSTIC FIBROSIS PATIENTS

[75] Inventors: Vojo Deretic, San Antonio, Tex.; Daniel W. Martin, Palo Alto, Calif.

[73] Assignee: Board of Regents, The University of Texas System, Austin, Tex.

[ * ] Notice: This patent is subject to a terminal disclaimer.

[21] Appl. No.: 08/505,307

[22] Filed: Nov. 24, 1995

Related U.S. Application Data

[63] Continuation-in-part of application No. 08/017,114, Feb. 12, 1993, Pat. No. 5,591,838.

[51] Int. Cl.⁷ ..................................................... C12Q 1/68
[52] U.S. Cl. .............................................. 435/6; 536/23.7
[58] Field of Search ......................... 435/6, 320.1, 255.1, 435/252.1, 419, 410; 536/23.7

[56] References Cited

FOREIGN PATENT DOCUMENTS

WO 86/07095  12/1986  WIPO.
WO 94/18223  8/1994  WIPO.

OTHER PUBLICATIONS

Allen and Hanson, "Construction of Broad–Host–Range Cosmid Cloning Vectors: Identification of Genes Necessary for Growth of *Methylobacterium Organophilum* on Methanol", *Journal of Bacteriology*, 161(3):955–962, Mar. 1985.

Anwar et al., "Establishment of Aging Biofilms: Possible Mechanism of Bacterial Resistance to Antimicrobial Therapy", *Antimicrobial Agents and Chemotherapy*, 36(7):1347–1351, Jul. 1992.

Barry et al., "Nucleoid Condensation in *Escheerichia Coli* That Express a Chlamydial Histone Homolog", *Science*, 256:377–379, Apr. 1992.

Berry et al., "High Osmolarity is a Signal for Enhanced algD Transcription in Mucoid and Nonmucoid *Pseudomonas aeruginosa* Strains", *Journal of Bacteriology*, 171(5):2312–2317, May 1989.

Burbulys et al., "Initiation of Sporulation in *B. subtilis* Is Controlled by a Multicomponent Phosphorelay", *Cell*, 64:545–552, Feb. 1991.

Chater et al., "The Development Fate of S. coelicolor Hyphae Depends Upon a Gene Product Homologous with the Motility δ Factor of *B. subtilis*", *Cell*, 59:133–143, Oct. 1989.

Costerton et al., "Bacterial Biofilms in Nature and Disease", *Am. Rev. Microbiol*, 44:435–464.

Darzins et al., "Clustering of Mutations Affecting Alginic Acid Biosynthesis in Mucoid *Pseudomonas aeruginosa*", *Journal of Bacteriology*, 164(2):516–524, Nov. 1985.

Deretic et al., "Common Denominators of Promoter Control in Pseudomonas and Other Bacteria", *Bio/Technology*, 7:1249–1254, Dec. 1989.

Deretic et al., "A Set of Cassettes and Improved Vectors for Genetic and Biochemical Characterization of Pseudomonas Genes", *Gene*, 57:61–72, 1987.

Deretic et al., "Gene algD Coding for GDPmannose Dehydrogenase is Transcriptionally Activated in Mucoid *Pseudomonas aeruginosa*", *Journal of Bacteriology*, 169(1):351–358, Jan. 1987.

Deretic et al., "Conversion to Mucoidy in *Pseudomonas aeruginosa*", *Bio/Technology*, 11:1133–1136, Oct. 1993.

Deretic et al., "Conversion of *Pseudomonas aeruginosa* to Mucoidy in Cystic Fibrosis: Environmental Stress and Regulation of Bacterial irulence by Alternative Sigma Factors", *Journal of Bacteriology*, 176(10):2273–2780, May 1994.

Deretic et al., "*Pseudomonas aeguginosa*, Mucoidy and the Chronic Infection Phenotype in Cystic Fibrosis", *Trends in Microbiology*, 3:351–356, 1995.

Deretic et al., "Immunocytochemical Analysis of AlgP ($H_p1$), a Histonelike Element Participating in Control of Mucoidy in *Pseudomonas aeruginosa*", *Journal of Bacteriology*, 174(3):824–831, Feb. 1992.

Deretic et al., "Mucoid *Pseudomonas aeruginosa* in Cystic Fibrosis: Signal Transduction and Histone–Like Elements in the Regulation of Bacterial Virulence", *Molecular Microbiology*, 5(7):1577–1583, 1991.

Deretic et al., "The algR Gene, Which Regulates Mucoidy in *Pseudomonas aeruginosa*, Belongs to a Class of Environmentally Responsive Genes", *Journal of Bacteriology*, 171(5):1278–1283, Mar. 1989.

Deretic et al., "Control of Mucoidy in *Pseudomonas aeruginosa*: Transcriptional Regulation of algR and Identification of the Second Regulatory Gene, algQ", *Journal of Bacteriology*, 171(7):3680–3688, Jul. 1989.

(List continued on next page.)

Primary Examiner—Scott W. Houtteman
Attorney, Agent, or Firm—Arnold, White & Durkee

[57] ABSTRACT

Compositions and methods for detecting the conversion to mucoidy in *Pseudomonas aeruginosa* are disclosed. Chronic respiratory infections with mucoid *Pseudomonas aeruginosa* are the leading cause of high mortality and morbidity in cystic fibrosis. The initially colonizing strains are nonmucoid but in the cystic fibrosis lung they invariably convert into the mucoid form causing further disease deterioration and poor prognosis. Mucoidy is a critical *P. aeruginosa* virulence factor in cystic fibrosis that has been associated with biofilm development and resistance to phagocytosis. The molecular basis of this conversion to mucoidy is also disclosed. The present invention provides for detecting the switch from nonmucoid to mucoid state as caused by either frameshift deletions and duplications or nonsense changes in the second gene of the cluster, mucA. Inactivation of mucA results in constitutive expression of genes, such as algD, dependent on algU for transcription. Also disclosed is a novel alginate biosynthesis heterologous expression system for use in screening candidate substances that inhibit conversion to mucoidy.

21 Claims, 16 Drawing Sheets

OTHER PUBLICATIONS

Deretic et al., "In Vitro Phosphorylation of AlgR, a Regulator of Mucoidy in *Pseudomonas aeruginosa*, by a Histidine Protein Kinase and Effects of Small Phospho–Donor Molecules", *Molecular Microbiology*, 6(19):2761–2767, 1992.

Deretic et al., "A Procaryotic Regulatory Factor with a Histone H1–Like Carboxy–Terminal Domain: Clonal Variation of Repeats Within algP, a Gene Involved in Regulation of Mucoidy in *Pseudomonas aeruginosa*", *Journal of Bacteriology*, 172(10):5544–5554, Oct. 1990.

Deretic et al., "Mucoid *Pseudomonas aeruginosa* in Cystic Fibrosis: Mutations in the muc Loci Affect Transcription of the algR and algD Genes in Response to Environmental Stimuli", *Molecular Microbiology*, 4(2):189–196, 1990.

DeVault et al., "Pulmonary Dehydration and Infection in Cystic Fibrosis: Evidence That Ethanol Activiates Alginate Gene Expression and Induction of Mucoidy in *Pseudomonas aeruginosa*", *Molecular Microbiology*, 4(5):737–745, 1990.

Dubnau et al., "Bacillus Sporulation Gene spoOH Codes for $\delta^{30}$ ($\delta^H$)", *Journal of Bacteriology*, 170(3):1054–1062, Mar. 1988.

Dubnau, "The Regulation of Genetic Competence in *Bacillus subtilis*", *Molecular Microbiology*, 5(1):11–18, 1991.

Figurski and Helinski, "Replication of an Origin–Containing Derivative of Plasmid RK2 Dependent on a Plasmid Function Provided in Trans", *Proc. Natl. Acad. Sci, USA*, 76(4):1648–1652, Apr. 1979.

Fyfe and Govan, "Alginate Synthesis in Mucoid *Pseudomonas aeruginosa*: A Chromosomal Locus Involved in Control", *Journal of General Microbiology*, 119:443–450, 1980.

Fyfe and Govan, "Synthesis, Regulation and Biological Function of Bacterial Alginate", In Progress in *Inductrial Microbiloogy*, 18:45–83, (Bushnell, M. E., ed.) Elsevier, Amsterdam, 1983.

Goldberg et al., "Precise Excision and Instability of the Transposon Tn5 in *Pseudomonas aeruginosa*", *Journal of General Microbiology*, 136:789–796, 1990.

Goldberg et al., "A Mutation in algN Permits Trans Activation of Alginate Production by algT in Pseudomonas Species", *Journal of Bacteriology*, 175(5):1303–1308, Mar. 1993.

Govan and Harris, "*Pseudomonas aeruginosa* and Cystic Fibrosis: Unusual Bacterial Adaptation and Pathogenesis", *Microbiological Sciences*, 3(10):302–308, 1986.

Helmann and Chamberlin, "Structure and Function of Bacterial Sigma Factors", *Am. Rev. Biochem.*, 57:839–872, 1988.

Hindahl et al., "Characterization of a Gene That Regulates Toxin A Synthesis in *Pseudomonas aeruginosa*", *Nucleic Acids Research*, 16(12):5699, 1988.

Holloway, "Genetic Recombination in *Pseudomonas aeruginosa*", *Journal of General Microbiology*, 13:572–581, 1955.

Ishimoto and Lory, "Formation of Pilin in *Pseudomonas aeruginosa* Requires the Alternative $\delta$ Factor (RpoN) of RNA Polymerase", *Proc. Natl. Acad. Sci., USA*, 86:1954–1957, Mar. 1989.

Kato et al., "AlgR3, A Protein Resembling Eukaryotic Histone H1, Regulates Alginate Synthesis in *Pseudomonas aeruginosa*", *Proc. Natl. Acad. Sci., USA*, 87:2887–2891, Apr. 1990.

Kalman et al., "Similar Organization of the sigB and spoIIA Operons Encoding Alternate Sigma Factors of *Bacillus subtilis* RNA Polymerase", *Journal of Bacteriology*, 172(10):5575–5585, Oct. 1990.

Kimbara and Chakrabarty, "Control of Alginate Synthesis in *Pseudomonas aeruginosa*: Regulation of the algR1 Gene", *Biochemical and Biophysical Research Communications*, 164(2):601–608, Oct. 1989.

Knutson and Jeanes, "A New Modification of the Carbazole Analysis: Application to Heteropolysaccharides", *Analytical Biochemistry*, 24:470–481, 1968.

Konyecsni and Deretic, "Broad–Host–Range Plasmid and M13 Bacteriophage–Derived Vectors for Promoter Analysis in *Escherichia coli* and *Pseudomonas aeruginosa*", *Gene*, 74:375–386, 1988.

Krieg et al., "Resistance of Mucoid *Pseudomonas aeruginosa* to Nonopsonic Phagocytosis by Alveolar Macrophages In Vitro", *Infection and Immunity*, 56(12):3173–3179, Dec. 1988.

Krishnapillai, "A Novel Transducing Phage: Its Role in Recognition of a Possible New Host–Controlled Modification System in *Pseudomonas aeruginosa*", *Molecular General Genetics*, 114:134–143, 1971.

Lonetto et al., "The $\delta$ Family: Sequence Conservation and Evolutionary Relationships", *Journal of Bacteriology*, 174(12):3843–3849, Jun. 1992.

Merrick and Gibbins, "The Nucleotide Sequence of the Nitrogen–Regulation Gene ntrA of *Klebsiella pneumoniae* and Comparison with Conserved Features in Bacterial RNA Polymerase Sigma Factors", *Nucleic Acids Research*, 13(21):7607–7620, 1985.

May et al., "Alginate Synthesis by *Pseudomonas aeruginosa*: A Key Pathogenic Factor in Chronic Pulmonary Infections of Cystic Fibrosis Patients", *Clinical Microbiology Reviews*, 4(2):191–206, Apr. 1991.

MacGeorge et al., "Transfer of a Chromosomal Locus Responsible for Mucoid Colony Morphology in *Pseudomonas aeruginosa* Isolated from Cystic Fibrosis Patients to *P. aeruginosa* PAO", *Journal of Medical Microbiology*, 21:331–336, 1986.

Martin et al., "Mechanism of Conversion to Mucoidy in *Pseudomonas aeruginosa* Infecting Cystic Fibrosis Patients", *Proc. Natl. Acad. Sci., USA*, 90:8377–8381, Sep. 1993.

Martin et al., "Analysis of Promoters Controlled by the Putative Sigma Factor AlgU Regulating Conversion to Mucoidy in *Pseudomonas aeruginosa*: Relationship to $\delta^E$ and Stress Response", *Journal of Bacteriology*, 176(21):6688–6696, Nov. 1994.

Meile et al., "Regulation of Proline Catabolism in *Pseudomonas aeruginosa* PAO", *Archives of Microbiology*, 132:189–193, 1982.

Miller et al., "Coordinate Regulation and Sensory Transduction in the Control of Bacterial Virulence", *Science*, 243:916–922, Feb. 1989.

Mohr et al., "Role of the Far–Upstream Sites of the algD Promoter and the algR and rpoN Genes in Environmental Modulation of Mucoidy in *Pseudomonas aeruginosa*", *Journal of Bacteriology*, 172(11):6576–6580, Nov. 1990.

Mohr and Deretic, "Gene–Scrambling Mutagenesis: Generation and Analysis of Insertional Mutations in the Alginate Regulatory Region of *Pseudomonas aeruginosa*", *Journal of Bacteriology*, 172(11):6252–6260, Nov. 1990.

Mohr et al., "AlgR, A Response Regulator Controlling Mucoidy in *Pseudomonas aeruginosa*, Binds to the FUS Sites of the algD Promoter Located Unusually Far Upstream from the mRNA Start Site", *Journal of Bacteriology*, 173(16):5136–5143, Aug. 1990.

Mohr et al., "AlgR–Binding Sites Within the algD Promoter Make Up a Set of Inverted Repeats Separated by a Large Intervening Segment of DNA", *Journal of Bacteriology*, 174(20):6624–6633, Oct. 1992.

Mohr and Deretic, "In Vitro Interactions of the Histone–Like Protein IHF With the algD Promoter, A Critical Site for Control of Mucoidy in *Pseudomonas aeruginosa*", *Biochemical and Biophysical Research Communications*, 189(2):837–844, Dec. 1992.

Ohnishi et al., "A Novel Transcriptional Regulation Mechanism in the Flagellar Regulon of *Salmonella typhimurium*: An Anti–Sigma Factor Inhibits the Activity of the Flagellum–Specific Sigma Factor, $\delta^F$", *Molecular Microbiology*, 6(21):3149–3157, 1992.

Pearson and Lipman, "Improved Tools for Biological Sequence Comparison", *Proc. Natl. Acad. Sci., USA*, 85:2444–2448, Apr. 1988.

Pedersen et al., "*Pseudomonas aeruginosa* Alginate in Cystic Fibrosis Sputum and the Imflammatory Response", *Infection and Immunity*, 58(10):3363–3368, Oct. 1990.

Pier et al., "Opsonophagocytic Killing Antibody to *Pseudomonas aeruginosa* Mucoid Exopolysaccharide in Order Noncolonized Patients With Cystic Fibrosis", *The New England Journal of Medicine*, 317(13):793–798, Sep. 1987.

Pier et al., "Protection Against Mucoid *Pseudomonas aeruginosa* in Rodent Models of Endobronchial Infections", *Science*, 249:537–540, Aug. 1990.

Predich et al., "*Bacillus subtilis* Early Sporulation Genes kinA, spoOF, and spoOA are Transcribed by the RNA Polymerase Containing $\delta^H$", *Journal of Bacteriology*, 174(9):2771–2778, May 1992.

Rappuoli et al. "Thermoregulation and Reversible Differentiation in Bordetella: A Model for Pathogenic Bacteria", *Molecular Microbiology*, 6(13):2209–2211, 1992.

Pressler et al., "Immunoglobulin Allotypes and IgG Subclass Antibody Response to *Pseudomonas aeruginosa* Antigens in Chronically Infected Cystic Fibrosis Patients", *Clin. Exp. Immunol.*, 90:209–214, 1992.

Ratnaningsih et al., "A Combined Physical and Genetic Map of *Pseudomonas aeruginosa* PAO", *Journal of General Microbiology*, 136:2351–2357, 1990.

Shortridge et al., "Physical Mapping of Virulence–Associated Genes in *Pseudomonas aeruginosa* by Transverse Alternating–Field Electrophoresis", *Infection and Immunity*, 59(10):3596–3603, Oct. 1991.

Schmidt et al., "Control of Developmental Transcription Factor $\delta^F$ by Sporulation Regulatory Proteins SpoIIAA and SpoIIAB in *Bacillus subtilis*", *Proc. Natl. Acad. Sci., USA*, 87:9221–9225, Dec. 1990.

Schurr et al., "Multiple Promoters and Induction by Heat Shock of the Gene Encoding the Alternative Sigma Factor AlgU ($\delta^E$) Which Controls Mucoidy in Cystic Fibrosis Isolates of *Pseudomonas aeruginosa*", *Journal of Bacteriology*, 177(19):5670–5679, Oct. 1995.

Simon et al., "A Broad Host Range Mobilization System for In Vivo Genetic Engineering: Transposon Mutagenesis in Gram Negative Bacteria", *Bio/Technology*, 1:784–790, Nov. 1993.

Stock et al., "Protein Phosphorylation and Regulation of Adaptive Responses in Bacteria", *Microbiological Reviews*, 53(4):450–490, Dec. 1989.

Stragier et al., "Chromosomal Rearrangement Generating a Composite Gene for a Developmental Transcription Factor", *Science*, 243:507–512, Jan. 1989.

Tatti et al., "Sigma H–Directed Transcription of citG in *Bacillus subtilis*", *Journal of Bacteriology*, 171(11):5928–5932, Nov. 1989.

Terry et al., "Environmental Conditions Which Influence Mucoid Conversion in *Pseudomonas aeruginosa* PAO1", *Infection and Immunity*, 59(2):471–477, Feb. 1991.

Tosi et al., "Neutrophil Elastase Cleaves C3bi on Opsonized Pseudomonas as Well as CR1 on Neutrophils to Create a Functionally Important Opsonin Receptor Mismatch", *J. Clin. Invest.*, 86:300–308, Jul. 1990.

Totten et al., "The rpoN Gene Product of *Pseudomonas aeruginosa* Is Required for Expression of Diverse Genes, Including the Flagellin Gene", *Journal of Bacteriology*, 172(1):389–396, Jan. 1990.

Trempy et al., "Synthesis of $\delta^{29}$, An RNA Polymerase Specificity Determinant, Is a Developmentally Regulated Event in *Bacillus subtilis*", *Journal of Bacteriology*, 161(1):340–346, Jan. 1985.

West and Iglewski, "Codon Usage in *Pseudomonas aeruginosa*", *Nucleic Acids Research*, 16(19):9323–9335, 1988.

Woodruff et al., "Sequence Analysis of *Pseudomonas aeruginosa* DNA Containing the Alginate Gene algT Revealed the Adjacent Gene nadB Encoding Aspartate Oxidase", American Society for Microbiology, p. 103, Abstracts of the General Meeting 1992.

Wozniak and Ohman, "*Pseudomonas aeruginosa* AlgB, A Two–Component Response Regulator of the NtrC Family, Is Required for algD Transcription", *Journal of Bacteriology*, 173(4):1406–1413, Feb. 1991.

Yu et al., "Functional Equivalence of *Escherichia coli* $\delta^E$ and *Pseudomonas aeruginosa* AlgU: *E. coli* rpoE Restores Mucoidy and Reduces Sensitivity to Reactive Oxygen Intermediates in algU Mutants of *P. aeruginosa*", *Journal of Bacteriology*, 177(11):3259–3268, Jun. 1995.

```
U4/76  ⊕
     ↱
     GTCTATCTTG  GCAAGACGAT  TCGCTGGGAC  GCTCGAAGCT  CCTCCAGGTT  CGAAGAGGAG    60
                                                                     SD

M   L      T   Q   E      Q   Q   Q   Q      L   Y   E      R   V   Q      R   G   D   K
     CTTTCATGCT  AACCCAGGAA  CAGGATCAGC  AACTGGTTGA  ACGGGTACAG  CGCGGAGACA   120

R   A   F      D   L   L      V   L   K   Y      Q   H   K      I   L   G      L   I   V   R
     AGCGGGCTTT  CGATCTGCTG  GTACTGAAAT  ACCAGCACAA  GATACTGGGA  TTGATCGTGC   180

F   V   H      D   A   Q      E   A   Q      V   A   Q      E   A   F      I   K   A   Y
     GGTTCGTGCA  CGACGCCCAG  GAAGCCCAGG  ACGTAGCGCA  GGAAGCCTTC  ATCAAGGCAT   240

R   A   L      G   N   F      R   G   D   S      A   F   Y      T   V   L      Y   R   I   A
     ACCGTGCGCT  CGGCAATTTC  CGGCGGGATA  GTGCTTTTTA  TACCTGGCTG  TATCGGATCG   300
                                                     U4/33
                                                    ↱ V   A      R   G   R
      I   N   T      A   K   N      H   L   V   A      R   G   R      R   P   P      D   S   D   V
     CCATCAACAC  CGCGAAGAAC  CACCTGGTCG  CTCGCGGGGG  TCGGCCACCG  GACAGCGATG   360
                                              ⊖
      T   A   E      D   A   E      F   F   E   G      D   H   A      L   K   D      I   E   S   P
     TGACCGGCAGA  GGATGCGGAG  TTCTTCGAGG  GCGACCACGC  CCTGAAGGAC  ATCGAGTCGC   420

E   R   A      H   L   R      D   E   I   E      A   T   V      R   E   F      I   Q   Q   L
     CGGAACGGGC  GATGTTGCGG  GATGAGATCG  AGGCCACCGT  GCGCGAGTTC  ATCCAGCAGT   480

P   E   D      L   R   T      A   L   T   L      C   P   V   G      E   G   L      S   Y   E   D
     TGCCCGAGGA  TTTGCGCACG  GCCCTGACCC  TGCCGGAGTT  CGAAGGTTTG  AGTTACGAAG   540

I   A   T      V   M   Q      C   G   T   D      L   Q   P   L      L   R   E      S   R   I      F   R   A   R
     ATATCGCCAC  CGTGATGCAG  CTGCAGCCTT  TGTTGCGAGA  AGCCTGA      (SEQ ID NO:9)
     EcoRV

E   A   I      D   K   A
     GTGAAGCAAT  CGACAAAGCT
```

FIG. 1

```
                 algU
TTTGTTGCGA  GAAGCCTGAC  ACAGCGGGCAA  ATGCCAAGAG  AGGTATCGCT                                60
 L  L  R     E  A  * mucA
                                                              ATGAGTCGTG                   
                                                               M  E  R  E AAGCCCTGCA  GGAAACTCTG  TCCGCTGTGA  TGGATAACGA  AGCGGATGAA  CTCGAGTTGC                     120
 A  L  Q     E  T  L    S  A  V  M   D  N  E    A  D  E     L  E  L  R GGCGGGGTGCT  CGCAGCTTGC  GGCGAGGATG  CCGAGCTGCC  AGCGGATGAA  TCGCGTTACC                    180
 R  V  L     A  A  C    G  E  D  A   E  L  P    S  T  W     S  P  Y  Q AGTTGGCGCG  GTCCGTCATG  CACCCGCGAGC  CTACCCTGCC  GAAGCTGGAT  ATCGCTGCGG                    240
 L  A  R     S  V  M    H  R  E  P    T  L  P    K  L  D     I  A  A  A CGGTCTCTGC  TGCCCTGGCC  GACGAGGCCG  CTCCGCCGAA  AGCGGAGAAG  GGACCGTGGG                     300
 V  S  A    L  A        D  E  A  A    P  P  K    A  E  K     G  P  W  R GGATGGTCGG  TCGCCTGGCG  GTCGCTGCCT  CGGTGACCCT  GGCGGGTCTG  GCCGGGGTGTG                    360
 M  V  G     R  L  A    V  A  A  S    V  T  L    A  G  V     A  G  V  R GTCTGTACAA  CCAGAACGAC  AAATGGCGCA  ACAGGGGACC  CTACAGCGAA  ACCCCGCAGA                    420
 L  Y  N     Q  N  D    M  A  Q       Q  G  T    Y  S  E     T  P  Q  I TCGCCCCTGCC  TCAGGTGAAA  TGCTGGCCGG  TCAGGTGAAA  CTGGCATGAG  GAGCAGGGGG                    480
 A  L  P     Q  V  K    L  A  G       Y  S  E    W  H  E     E  Q  G  A CGCCGGCAGGT  GATCACCAAC  GCGATACCCG  CTACAGCGAA  CTGGCATGAG  CAGCGGGTCTGC                  540
 P  Q  V     I  T  N    D  T  R      W  H  E     Q  R  L  P CGATCTACCT  GCGTCAGCAC  GTGCAACAAT  CCGCCGTCAG  TGGTACAGAG  AGCGGCGCTGC                    600
 I  Y  L     R  Q  H    V  Q  Q  S    A  V  S    G  T  E     S  A  L  P
```

FIG. 2A

```
                                                             mucB
CCTACGCTCG GGCAGCCAGC CTGGAAAACC GCTGAGGAGA GACATGCGCA CCACCTCCCT   660
 Y  A  R    G  S  Q    L  E  N    R  *  SD       M  R  T  T  S  L GTTGCTTTTG CTTGGCAGCC TGATGGCGGT TCCCGCCACT CAGGCTGCCG ACGCTTCCGA   720
 L  L  L    L  G  S  L  M  A  V   P  A  T    Q  A  A  D  A  S  D CTGGCTGAAT CGTCTCGCCG AGGCCGATCG CCAGAACAGT TTCCAAGGCA CCTTCGTCTA   780
 W  L  N  R  L  A  E    A  D  R   Q  N  S   F  Q  G  T   F  V  Y
                                BgIII
CGAGCGCAAT GGCAGCTTCT CCACCCATGA GATCTGGCAT CGCGTGGAGA GCGATGGTGC   840
 E  R  N   G  S  F  S   T  H  E   I  W  H    R  V  E  S   D  G  A GGTTCGCGAG CGCCTGCTCC AGCTCGACGG CGGCGCCCAG GAAGTGGTCC GGGTCGACGG   900
 V  R  E    R  L  L  Q  L  D  G   A  R  Q    E  V  V  R   V  D  G GCGCACCCAG TGCATCAGCG GCGGCCTTGC CGACCAAACTG GCCGATGCCC AGCTGTGGCC   960
 R  T  Q   C  I  S  G   L  A  D   Q  L  A  D   A  Q    L  W  P GGTGCGCAAG TTCGATCCCT CCCAGCTGGC TTCCTGGTAC GACCTGCGCC TGGTCGGGGA   1020
 V  R  K    F  D  P  S   Q  L  A   S  W  Y    D  L  R  L   V  G  E ATCCCGTGTC GCCGGCCGCC CGGCAGTGGT CCTTGCCGTG ACTCCGCGCG ACCAGCATCG   1080
 S  R  V    A  G  R  P  A  V  V   L  A  V    T  P  R  D   Q  H  R CTACGGCTTC GAGCTGCACC TGGACCGCGA CACCGGCCTG CCGTTGAAGT CGCTGCTGCT   1140
 Y  G  F    E  L  H  L   D  R  D   T  G  L   P  L  K  S    L  L  L GAACGAGAAG GGGCAGTTGC TCGAGCCGCTT CCAGTTCACC CAGTTGAATA CCGGCGGCGC  1200
 N  E  K    G  Q  L    Q  L       Q  F  T    Q  L  N  T   G  A  A
```

FIG. 2B

```
ACCTGCCGAA GACCAGTTGC AGGCGGGCGC CGAATGCCAG GTCGTCGGCC CGGCCAAGGC   1260
 P  A  E    D  Q  L  Q    A  G  A    E  C  Q    V  V  G  P    A  K  A

CGACGGGGAG AAGACCGTGG CCTGGCGCTC GGAATGGCTG CCGCCAGGTT TCACCCTGAC   1320
 D  G  E    K  T  V  A    W  R  S    E  W  L    P  P  G  F    T  L  T
              ΔUM9
             ┌──►
CCGCAGTTTC ATGCGGTCGCA GTCCGGTCAC CCCCGATCCG GTCGCCCTGCC TGACCTATGG   1380
 R  S  F    M  R  S    P  V  T    P  D  P    V  A  I  L    T  Y  D

CGATGGCCTG GCACGATTCT CGGTGTTCAT CGAGCCGCTG CACGGTGCCA TGGTTGGCGA   1440
 D  G  L    A  R  F  D    V  F  I    E  P  L    H  G  A  M    V  G  D

CGGCGCGAGC CAGCTCGGCC CGACCGTGGT GGTTTCCAAG CGCCTGCAGA CCGATGACGG   1500
 A  R  S    Q  L  G  P    T  V  V    V  S  K    R  L  Q  T    D  D  G

CGGCCAGATG GTGACCGTCG TCGGCGAAGT GCCGCTGGGC ACCGCCGAGC GGGTGGCGCT   1560
 G  Q  M    V  T  V  V    G  E  V    P  L  G    T  A  E  R    V  A  L

GTCCATCCGG CCCGAGGCCG CCGCCCAGAA ATGATCGAGG AGCAGGGGCG AGTGGTGGCG   1620
 S  I  R    P  E  A  A    A  Q  K    *

ACCGAGCCGG GAGCGGGTATG GGTCGAGACC GTGCGCCGAG TACCTGCTCG TCCTGCTCGG   1680

CCAATGCCGG TTGCGGCCAG GGGCTGATGC AGCGCCTGGG CGTCGGCCGC GGGCCGTGCC   1740

GGGTGCGCGC GTTGAGCCGAC CTGAGCCTGC GGGTCGGGCGA TGCGGGTCGTC CTAGGAATTC   1800
                                                           EcoRI (SEQ ID NO:10)
```

FIG. 2C

```
 1                                                          ⬜T CF8
AGGTATCGCTATGAGTCGTGAAGCCCTG..........    ....CTGCCGCAAATGGCGAAC̄AGG
        M  S  R  E  A  L  .              .   L  P  Q  M  A  Q  Q  G
                   mucA2                          Δ(mucA22 CF14 CF23)
GGCCCCGGCCGTGCTGGCCGGCTACAGCGAAGAGCAGGGḠCGCCGCAGGT̄GĀTCACCAACTCCTCG
 G  P  A  V  L  A  G  Y  S  E  E  Q  G  ▲ A  P  Q  V  I  T  N  S  S
                                         Δ(mucA22 CF14 CF23)
CGATCTACCTGCGTCAGCACGTGCAACAATCCGCCGTCAGTGGTACAGAGAGCGCCCTACG
 I  Y  L  R  Q  H  V  Q  Q  S  A  V  S  G  T  E  S  A  L  P  Y  A
```

```
 ΔCF1                                               400
       GACCAC̄CCCCGCAGATCGCCCTGCCTCAGGT̄GĀAA
        T  T  P  Q  I  A  L  P  Q  V  K
                                          500
TCCAGGGATACCCGCTGGCATGAGCAGCGTCTGC
 S  S  D  T  R  W  H  E  Q  R  L  P
                                     595
CTCGGGGCAGCCAGCCTGGAAAACCGCTGA
 R  A  A  S  L  E  N  R  *
                (SEQ ID NO:1)
```

```
         M  L  T  Q  E  Q  D  Q  Q  L                   Y  T  W  L  Y  R  I
AGGAGCTTTCATGCTAACCCAGGAACAGGATCAGCAACTG......TATACCTGGCTGTATCGGATC
    SD                                                            A (algU74-1)

V  M  Q  C  P  V  G  T  V  R  S  R  I  F  R  A  R  E  A  I  D  K  A
GTTGATGCAGTGTCCGGTACGGTCCGCTCGCGGATCTTCCGCGCTCGTGAAGCAATCGACAAAGC
```

FIG. 9A-1

```
                   158
         Y  E  D  I  A  T
      ....TACGAAGATATCGCCACC
                 ΔT (algU160-1)

L  Q  P  L  L  R  E  A  *
TCTGCAGCCTTTGTTGCGAGAAGCCTGA (SEQ ID NO:19)
```

FIG. 9A-2

```
                          SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
        (A) LENGTH: 595 base pairs
        (B) TYPE: nucleic acid
        (C) STRANDEDNESS: single
        (D) TOPOLOGY: linear (xi) SEQUENCE DESCRIPTION: SEQ ID NO:1:

AGGTATCGCT ATGAGTCGTG AAGCCCTGCA GGAAACTCTG TCCGCTGTGA TGGATAACGA      60

AGCGGATGAA CTCGAGTTGC GGCGGGTGCT CGCAGCTTGC GGCGAGGATG CCGAGCTGCG     120

TTCCACCTGG TCGCGTTACC AGTTGGCGCG GTCCGTCATG CACCGCGAGC CTACCCTGCC     180

GAAGCTGGAT ATCGCTGCGG CGGTCTCTGC TGCCCTGGCC GACGAGGCCG CTCCGCCGAA     240

AGCGGAGAAG GGACCGTGGC GGATGGTCGG TCGCCTGGCG GTCGCTGCCT CGGTGACCCT     300

GGCGGTGCTG GCCGGCGTGC GTCTGTACAA CCAGAACGAC GCCCTGCCGC AAATGGCGCA     360

ACAGGGGACC ACCCCGCAGA TCGCCCTGCC TCAGGTGAAA GGCCCGGCCG TGCTGGCCGG     420

CTACAGCGAA GAGCAGGGGG CGCCGCAGGT GATCACCAAC TCCTCGTCCA GCGATACCCG     480

CTGGCATGAG CAGCGTCTGC CGATCTACCT GCGTCAGCAC GTGCAACAAT CCGCCGTCAG     540

TGGTACAGAG AGCGCGCTGC CCTACGCTCG GGCAGCCAGC CTGGAAAACC GCTGA          595

(2) INFORMATION FOR SEQ ID NO:2:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (xi) SEQUENCE DESCRIPTION: SEQ ID NO:2:

GGGACCCCCC GCA                                                         13

(2) INFORMATION FOR SEQ ID NO:3:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (xi) SEQUENCE DESCRIPTION: SEQ ID NO:3:

GAGCAGGGGC GCC                                                         13

(2) INFORMATION FOR SEQ ID NO:4:

(i) SEQUENCE CHARACTERISTICS:
```

(A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:4:

CAGGGGGCCA GGGGGC                                                      16

(2) INFORMATION FOR SEQ ID NO:5:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:5:

GCCGCACGTC ACGAGC                                                      16

(2) INFORMATION FOR SEQ ID NO:6:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:6:

GAGTCCATCC GCTTCG                                                      16

(2) INFORMATION FOR SEQ ID NO:7:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:7:

CTGTCCGCTG TGATGG                                                      16

(2) INFORMATION FOR SEQ ID NO:8:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:8:

CGCCCCTGCT CCTCGA                                                      16

(2) INFORMATION FOR SEQ ID NO:9:

(i) SEQUENCE CHARACTERISTICS:
        (A) LENGTH: 647 base pairs
        (B) TYPE: nucleic acid
        (C) STRANDEDNESS: single
        (D) TOPOLOGY: linear (xi) SEQUENCE DESCRIPTION: SEQ ID NO:9:

GTCTATCTTG GCAAGACGAT TCGCTGGGAC GCTCGAAGCT CCTCCAGGTT CGAAGAGGAG       60

CTTTCATGCT AACCCAGGAA CAGGATCAGC AACTGGTTGA ACGGGTACAG CGCGGAGACA      120

AGCGGGCTTT CGATCTGCTG GTACTGAAAT ACCAGCACAA GATACTGGGA TTGATCGTGC      180

GGTTCGTGCA CGACGCCCAG GAAGCCCAGG ACGTAGCGCA GGAAGCCTTC ATCAAGGCAT      240

```
ACCGTGCGCT CGGCAATTTC CGCGGCGATA GTGCTTTTTA TACCTGGCTG TATCGGATCG      300

CCATCAACAC CGCGAAGAAC CACCTGGTCG CTCGCGGGCG TCGGCCACCG GACAGCGATG      360

TGACCGCAGA GGATGCGGAG TTCTTCGAGG GCGACCACGC CCTGAAGGAC ATCGAGTCGC      420

CGGAACGGGC GATGTTGCGG GATGAGATCG AGGCCACCGT GCACCAGACC ATCCAGCAGT      480

TGCCCGAGGA TTTGCGCACG GCCCTGACCC TGCGCGAGTT CGAAGGTTTG AGTTACGAAG      540

ATATCGCCAC CGTGATGCAG TGTCCGGTGG GGACGGTACG GTCGCGGATC TTCCGCGCTC      600

GTGAAGCAAT CGACAAAGCT CTGCAGCCTT TGTTGCGAGA AGCCTGA                   647
```

(2) INFORMATION FOR SEQ ID NO:10:

(i) SEQUENCE CHARACTERISTICS:
        (A) LENGTH: 1800 base pairs
        (B) TYPE: nucleic acid
        (C) STRANDEDNESS: single
        (D) TOPOLOGY: linear (xi) SEQUENCE DESCRIPTION: SEQ ID NO:10:

```
TTTGTTGCGA GAAGCCTGAC ACAGCGGCAA ATGCCAAGAG AGGTATCGCT ATGAGTCGTG       60

AAGCCCTGCA GGAAACTCTG TCCGCTGTGA TGGATAACGA AGCGGATGAA CTCGAGTTGC      120

GGCGGGTGCT CGCAGCTTGC GGCGAGGATG CCGAGCTGCG TTCCACCTGG TCGCGTTACC      180

AGTTGGCGCG GTCCGTCATG CACCGCGAGC CTACCCTGCC GAAGCTGGAT ATCGCTGCGG      240

CGGTCTCTGC TGCCCTGGCC GACGAGGCCG CTCCGCCGAA AGCGGAGAAG GGACCGTGGG      300

GGATGGTCGG TCGCCTGGCG GTCGCTGCTC GGTGACCCTG GCGGTGCTGG CCGGCGTGCG      360

TCTGTACAAC CAGAACGACG CCCTGCCGCA AATGGCGCAA CAGGGGACCA CCCCGCAGAT      420

CGCCCTGCCT CAGGTGAAAG GCCCGGCCGT GCTGGCCGGC TACAGCGAAG AGCAGGGGGC      480

GCCGCAGGTG ATCACCAACT CCTCGTCCAG CGATACCCGC TGGCATGAGC AGCGTCTGCC      540

CGATCTACCT GCGTCAGCAC GTGCAACAAT CCGCCGTCAG TGGTACAGAG AGCGCGCTGC      600

CCTACGCTCG GCAGCCAGC CTGGAAAACC GCTGAGGAGA GACATGCGCA CCACCTCCCT      660

GTTGCTTTTG CTTGGCAGCC TGATGGCGGT TCCCGCCACT CAGGCTGCCG ACGCTTCCGA      720

CTGGCTGAAT CGTCTCGCCG AGGCCGATCG CCAGAACAGT TTCCAAGGCA CCTTCGTCTA      780

CGAGCGCAAT GGCAGCTTCT CCACCCATGA GATCTGGCAT CGCGTGGAGA GCGATGGTGC      840

GGTTCGCGAG CGCCTGCTCC AGCTCGACGG CGCGCGCCAG GAAGTGGTCC GGGTCGACGG      900

GCGCACCCAG TGCATCAGCG GCGGCCTTGC CGACCAACTG GCCGATGCCC AGCTGTGGCC      960

GGTGCGCAAG TTCGATCCCT CCCAGCTGGC TTCCTGGTAC GACCTGCGCC TGGTCGGGGA     1020

ATCCCGTGTC GCCGGCCGCC CGGCAGTGGT CCTTGCGGTG ACTCCGCGCG ACCAGCATCG     1080

CTACGGCTTC GAGCTGCACC TGGACCGCGA CACCGGCCTG CCGTTGAAGT CGCTGCTGCT     1140

GAACGAGAAG GGGCAGTTGC TCGAGCGCTT CCAGTTCACC CAGTTGAATA CCGGCGCGGC     1200

ACCTGCCGAA GACCAGTTGC AGGCGGGCGC CGAATGCCAG GTCGTCGGCC CGGCCAAGGC     1260

CGACGGGGAG AAGACCGTGG CCTGGCGCTC GGAATGGCTG CCGCCAGGTT TCACCCTGAC     1320

CCGCAGTTTC ATGCGTCGCA GTCCGGTCAC CCCCGATCCG GTCGCCTGCC TGACCTATGG     1380

CGATGGCCTG GCACGATTCT CGGTGTTCAT CGAGCCGCTG CACGGTGCCA TGGTTGGCGA     1440

CGCGCGCAGC CAGCTCGGCC CGACCGTGGT GGTTTCCAAG CGCCTGCAGA CCGATGACGG     1500

CGGCCAGATG GTGACCGTCG TCGGCGAAGT GCCGCTGGGC ACCGCCGAGC GGGTGGCGCT     1560

GTCCATCCGG CCCGAGGCCG CCGCCCAGAA ATGATCGAGG AGCAGGGGCG AGTGGTGGCG     1620
```

```
ACCGAGCCGG GAGCGGTATG GGTCGAGACC GTGCGCCGAG TACCTGCTCG TCCTGCTCGG      1680

CCAATGCCGG TTGCGGCCAG GGGCTGATGC AGCGCCTGGG CGTCGGCGCG GGGCGTGCCC      1740

GGGTGCGCGC GTTGAGCGAC CTGAGCCTGC GGGTCGGCGA TGCGGTCGTC CTAGGAATTC      1800

(2) INFORMATION FOR SEQ ID NO:11:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:11:

AGCGAAGAGC AGGGGCGCC GCAGGTGATC A                                       31

(2) INFORMATION FOR SEQ ID NO:12:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:12:

GAGCAGGGGG CGCCG                                                        15

(2) INFORMATION FOR SEQ ID NO:13:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:13:

AACAGGGGAC CACCCCGCAG ATCGCC                                            26

(2) INFORMATION FOR SEQ ID NO:14:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (xi) SEQUENCE DESCRIPTION: SEQ ID NO:14:

GGGACCACCC CGC                                                          13

(2) INFORMATION FOR SEQ ID NO:15:

(i) SEQUENCE CHARACTERISTICS:
        (A) LENGTH: 194 amino acids
        (B) TYPE: amino acid
        (C) STRANDEDNESS:
        (D) TOPOLOGY: linear (xi) SEQUENCE DESCRIPTION: SEQ ID NO:15:

Met Ser Arg Glu Ala Leu Gln Glu Thr Leu Ser Ala Val Met Asp Asn
1               5                   10                  15

Glu Ala Asp Glu Leu Glu Leu Arg Arg Val Leu Ala Ala Cys Gly Glu
            20                  25                  30

Asp Ala Glu Leu Arg Ser Thr Trp Ser Arg Tyr Gln Leu Ala Arg Ser
        35                  40                  45
```

-continued

```
Val Met His Arg Glu Pro Thr Leu Pro Lys Leu Asp Ile Ala Ala Ala
    50                  55                  60

Val Ser Ala Ala Leu Ala Asp Glu Ala Ala Pro Pro Lys Ala Glu Lys
65                  70                  75                  80

Gly Pro Trp Arg Met Val Gly Arg Leu Ala Val Ala Ala Ser Val Thr
                85                  90                  95

Leu Ala Val Leu Ala Gly Val Arg Leu Tyr Asn Gln Asn Asp Ala Leu
                100                 105                 110

Pro Gln Met Ala Gln Gln Gly Thr Thr Pro Gln Ile Ala Leu Pro Gln
            115                 120                 125

Val Lys Gly Pro Ala Val Leu Ala Gly Tyr Ser Glu Glu Gln Gly Ala
    130                 135                 140

Pro Gln Val Ile Thr Asn Ser Ser Ser Asp Thr Arg Trp His Glu
145                 150                 155                 160

Gln Arg Leu Pro Ile Tyr Leu Arg Gln His Val Gln Gln Ser Ala Val
                165                 170                 175

Ser Gly Thr Glu Ser Ala Leu Pro Tyr Ala Arg Ala Ala Ser Leu Glu
                180                 185                 190

Asn Arg
```

(2) INFORMATION FOR SEQ ID NO:16:

(i) SEQUENCE CHARACTERISTICS:
        (A) LENGTH: 5 amino acids
        (B) TYPE: amino acid
        (C) STRANDEDNESS:
        (D) TOPOLOGY: linear (xi) SEQUENCE DESCRIPTION: SEQ ID NO:16:

```
Leu Leu Arg Glu Ala
1               5
```

(2) INFORMATION FOR SEQ ID NO:17:

(i) SEQUENCE CHARACTERISTICS:
        (A) LENGTH: 194 amino acids
        (B) TYPE: amino acid
        (C) STRANDEDNESS:
        (D) TOPOLOGY: linear (xi) SEQUENCE DESCRIPTION: SEQ ID NO:17:

```
Met Ser Arg Glu Ala Leu Gln Glu Thr Leu Ser Ala Val Met Asp Asn
1               5                   10                  15

Glu Ala Asp Glu Leu Glu Leu Arg Arg Val Leu Ala Ala Cys Gly Glu
                20                  25                  30

Asp Ala Glu Leu Arg Ser Thr Trp Ser Arg Tyr Gln Leu Ala Arg Ser
            35                  40                  45

Val Met His Arg Glu Pro Thr Leu Pro Lys Leu Asp Ile Ala Ala Ala
    50                  55                  60

Val Ser Ala Ala Leu Ala Asp Glu Ala Ala Pro Pro Lys Ala Glu Lys
65                  70                  75                  80

Gly Pro Trp Arg Met Val Gly Arg Leu Ala Val Ala Ala Ser Val Thr
                85                  90                  95

Leu Ala Val Leu Ala Gly Val Arg Leu Tyr Asn Gln Asn Asp Ala Leu
                100                 105                 110

Pro Gln Met Ala Gln Gln Gly Thr Thr Pro Gln Ile Ala Leu Pro Gln
            115                 120                 125

Val Lys Gly Pro Ala Val Leu Ala Gly Tyr Ser Glu Glu Gln Gly Ala
```

```
            130                 135                 140
Pro Gln Val Ile Thr Asn Ser Ser Ser Asp Thr Arg Trp His Glu
145                 150                 155                 160

Gln Arg Leu Pro Ile Tyr Leu Arg Gln His Val Gln Gln Ser Ala Val
                165                 170                 175

Ser Gly Thr Glu Ser Ala Leu Pro Tyr Ala Arg Ala Ala Ser Leu Glu
                180                 185                 190

Asn Arg (2) INFORMATION FOR SEQ ID NO:18:

(i) SEQUENCE CHARACTERISTICS:
        (A) LENGTH: 316 amino acids
        (B) TYPE: amino acid
        (C) STRANDEDNESS:
        (D) TOPOLOGY: linear (xi) SEQUENCE DESCRIPTION: SEQ ID NO:18:

Met Arg Thr Thr Ser Leu Leu Leu Leu Gly Ser Leu Met Ala Val
1               5                   10                  15

Pro Ala Thr Gln Ala Ala Asp Ala Ser Asp Trp Leu Asn Arg Leu Ala
                20                  25                  30

Glu Ala Asp Arg Gln Asn Ser Phe Gln Gly Thr Phe Val Tyr Glu Arg
            35                  40                  45

Asn Gly Ser Phe Ser Thr His Glu Ile Trp His Arg Val Glu Ser Asp
50                  55                  60

Gly Ala Val Arg Glu Arg Leu Leu Gln Leu Asp Gly Ala Arg Gln Glu
65                  70                  75                  80

Val Val Arg Val Asp Gly Arg Thr Gln Cys Ile Ser Gly Gly Leu Ala
                85                  90                  95

Asp Gln Leu Ala Asp Ala Gln Leu Trp Pro Val Arg Lys Phe Asp Pro
            100                 105                 110

Ser Gln Leu Ala Ser Trp Tyr Asp Leu Arg Leu Val Gly Glu Ser Arg
            115                 120                 125

Val Ala Gly Arg Pro Ala Val Val Leu Ala Val Thr Pro Arg Asp Gln
        130                 135                 140

His Arg Tyr Gly Phe Glu Leu His Leu Asp Arg Asp Thr Gly Leu Pro
145                 150                 155                 160

Leu Lys Ser Leu Leu Leu Asn Glu Lys Gly Gln Leu Leu Glu Arg Phe
                165                 170                 175

Gln Phe Thr Gln Leu Asn Thr Gly Ala Ala Pro Ala Glu Asp Gln Leu
            180                 185                 190

Gln Ala Gly Ala Glu Cys Gln Val Val Gly Pro Ala Lys Ala Asp Gly
        195                 200                 205

Glu Lys Thr Val Ala Trp Arg Ser Glu Trp Leu Pro Pro Gly Phe Thr
        210                 215                 220

Leu Thr Arg Ser Phe Met Arg Arg Ser Pro Val Thr Pro Asp Pro Val
225                 230                 235                 240

Ala Cys Leu Thr Tyr Gly Asp Gly Leu Ala Arg Phe Ser Val Phe Ile
                245                 250                 255

Glu Pro Leu His Gly Ala Met Val Gly Asp Ala Arg Ser Gln Leu Gly
            260                 265                 270

Pro Thr Val Val Ser Lys Arg Leu Gln Thr Asp Gly Gly Gln
        275                 280                 285

Met Val Thr Val Val Gly Glu Val Pro Leu Gly Thr Ala Glu Arg Val
```

```
                290             295             300
Ala Leu Ser Ile Arg Pro Glu Ala Ala Ala Gln Lys
305                 310                 315
```

(2) INFORMATION FOR SEQ ID NO:19:

(i) SEQUENCE CHARACTERISTICS:
        (A) LENGTH: 193 amino acids
        (B) TYPE: amino acid
        (C) STRANDEDNESS:
        (D) TOPOLOGY: linear (xi) SEQUENCE DESCRIPTION: SEQ ID NO:19:

```
Met Leu Thr Gln Glu Gln Asp Gln Gln Leu Val Glu Arg Val Gln Arg
1               5                   10                  15
Gly Asp Lys Arg Ala Phe Asp Leu Leu Val Leu Lys Tyr Gln His Lys
            20                  25                  30
Ile Leu Gly Leu Ile Val Arg Phe Val His Asp Ala Gln Glu Ala Gln
        35                  40                  45
Asp Val Ala Gln Glu Ala Phe Ile Lys Ala Tyr Arg Ala Leu Gly Asn
    50                  55                  60
Phe Arg Gly Asp Ser Ala Phe Tyr Thr Trp Leu Tyr Arg Ile Ala Ile
65                  70                  75                  80
Asn Thr Ala Lys Asn His Leu Val Ala Arg Gly Arg Arg Pro Pro Asp
                85                  90                  95
Ser Asp Val Thr Ala Glu Asp Ala Glu Phe Phe Glu Gly Asp His Ala
            100                 105                 110
Leu Lys Asp Ile Glu Ser Pro Glu Arg Ala Met Leu Arg Asp Glu Ile
        115                 120                 125
Glu Ala Thr Val His Gln Thr Ile Gln Gln Leu Pro Glu Asp Leu Arg
    130                 135                 140
Thr Ala Leu Thr Leu Arg Glu Phe Glu Gly Leu Ser Tyr Glu Asp Ile
145                 150                 155                 160
Ala Thr Val Met Gln Cys Pro Val Gly Thr Val Arg Ser Arg Ile Phe
                165                 170                 175
Arg Ala Arg Glu Ala Ile Asp Lys Ala Leu Gln Pro Leu Leu Arg Glu
            180                 185                 190
Ala
```

(2) INFORMATION FOR SEQ ID NO:20:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:20:

GCCGCACGTC ACGAGC                                                      16

(2) INFORMATION FOR SEQ ID NO:21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:21:

CGCGAACCGC ACCATCGCTC                                             20

(2) INFORMATION FOR SEQ ID NO:22:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:22:

ATCGCTGTCC GGTCGGC          17

(2) INFORMATION FOR SEQ ID NO:23:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:23:

GAGTTCATCC GCTTCG          16

DETECTION OF CONVERSION TO MUCOIDY IN *PSEUDOMONAS AERUGINOSA* INFECTING CYSTIC FIBROSIS PATIENTS

The present application is a continuation-in-part of co-pending U.S. patent application Ser. No. 08/017,114, filed Feb. 12, 1993. The entire text of the above-referenced disclosures is specifically incorporated by reference herein without disclaimer. The government owns rights in the present invention pursuant to grant number AI31139 from the National Institutes of Health).

BACKGROUND OF THE INVENTION

Cystic Fibrosis (CF) is the most common inheritable lethal disease among Caucasians. There are approximately 25,000 CF patients in the U.S.A. The frequency of CF in several other countries (e.g., Canada, United Kingdom, Denmark) is high (ranging from 1 in 400 to 1 in 1,600 live births). There are numerous CF centers in the U.S.A. and Europe—specialized clinical facilities for diagnosing and treating children and adolescents with CF.

Chronic respiratory infections caused by mucoid *Pseudomonas aeruginosa* are the leading cause of high morbidity and mortality in CF. The initially colonizing *P. aeruginosa* strains are nonmucoid but in the CF lung they inevitably convert into the mucoid form. The mucoid coating composed of the exopolysaccharide alginate leads to the inability of patients to clear the infection, even under aggressive antibiotic therapies. The emergence of the mucoid form of *P. aeruginosa* is associated with further disease deterioration and poor prognosis.

The microcolony mode of growth of *P. aeruginosa*, embedded in exopolysaccharide biofilms in the lungs of CF patients (Costerton et al., 1983), among other functions, plays a role in hindering effective opsonization and phagocytosis of *P. aeruginosa* cells (Pier et al., 1987; Pier 1992). Although CF patients can produce opsonic antibodies against *P. aeruginosa* antigens, in most cases phagocytic cells cannot effectively interact with such opsonins (Pressler et al., 1992; Pier et al., 1990; Pier 1992). Physical hindrance caused by the exopolysaccharide alginate and a functionally important receptor-opsonin mismatch caused by chronic inflammation and proteolysis are contributing factors to these processes (Pedersen et al., 1990; Tosi et al., 1990; Pier, 1992). Under such circumstances, the ability of *P. aeruginosa* to produce alginate becomes a critical persistence factor in CF; consequently, selection for alginate overproducing (mucoid) strains predominates in the CF lung.

Synthesis of alginate and its regulation has been the object of numerous studies (Govan, 1988; Ohman et al., 1990; Deretic et al., 1991; May et al., 1991). It has been shown that several alginate biosynthetic genes form a cluster at 34 min of the chromosome (Darzins et al., 1985), and that the algD gene, encoding GDPmannose dehydrogenase, undergoes strong transcriptional activation in mucoid cells (Deretic et al., 1987; 1991). GDP mannose dehydrogenase catalyzes double oxidation of GDP mannose into its uronic acid, a reaction that channels sugar intermediates into alginate production. The transcriptional activation of algD has become a benchmark for measuring molecular events controlling mucoidy (Deretic et al., 1991; Ohman et al., 1990; May et al., 1991). Studies of these processes have lead to the uncovering of several cis- and trans-acting elements controlling algD promoter activity: (i) The algD promoter has been shown to consist of sequences unusually far upstream of the mRNA start site (Mohr et al., 1990). These sequences (termed RB1 and RB2), as well as a sequence closer to the mRNA start site (RB3) are needed for the full activation of algD (Mohr et al., 1990; 1991; 1992). (ii) AlgR, a response regulator from the superfamily of bacterial signal transduction systems (Deretic et al., 1989), binds to RB1, RB2, and RB3, and is absolutely required for high levels of algD transcription (Mohr et al., 1990; 1991; 1992). (iii) Another signal transduction factor, AlgB, also contributes to the expression of genes required for alginate synthesis (Wozniak and Ohman, 1991). (iv) The peculiar spatial organization of AlgR binding sites imposes steric requirements for the activation process. The conformation of the algD promoter appears to be affected by histone like proteins [e.g. Alg ($H_p1$) (Deretic et al., 1992) and possibly IHF (Mohr and Deretic, 1992)], and perhaps by other elements controlling nucleoid structure and DNA topology. (v) The algD promoter does not have a typical −35/−10 canonical sequence (Deretic et al., 1989). It has been proposed that RpoN may be the sigma factor transcribing this promoter; however, several independent studies have clearly ruled out its direct involvement (Mohr et al., 1990; Totten et al., 1990). The present inventors have cloned and characterized a new gene, algU, which plays a critical role in algD expression (Martin et al., 1993). The algU gene encodes a polypeptide product that shows sequence and domainal similarities to the alternative sigma factor SpoOH from Bacillus spp. (Dubnau et al., 1988). SpoOH, although dispensable for vegetative growth, is responsible for the initial events in the triggering of the major developmental processes in *Bacillus subtilis*, viz. sporulation and competence (Dubnau et al., 1988; Dubnau, 1991). These findings suggest that activation of alginate synthesis may represent a cell differentiation process participating in interconversions between planktonic organisms and biofilm embedded forms in natural environments (Martin et al., 1993; Costerton et al., 1987).

Inactivation of algU abrogates algD transcription and renders cells nonmucoid, further strengthening the notion that algU plays an essential role in the initiation of mRNA synthesis at algD (Martin et al., 1993). algU maps in the close vicinity of muc markers that have been demonstrated in the classical genetic studies by Fyfe and Govan (1980) to cause the emergence of mucoid strains constitutively overproducing alginate. The mucoidy-causing property of muc mutations has been based on the ability of different muc alleles (e.g. muc-2, muc-22, and muc-25) to confer mucoidy in genetic crosses (Fyfe and Govan, 1980; 1983). The present application describes the presence of additional genes immediately downstream of algU, termed mucA and mucB, which also play a role in the regulation of mucoidy.

Detection of mucoid *P. aeruginosa* is a standard practice, however, due to the variability in expression of mucoidy on standard clinical media, more objective detection methods are needed. An early detection of conversion to mucoidy will be possible by using the present invention.

SUMMARY OF THE INVENTION

The present invention provides compositions and methods for the early detection and diagnosis of the conversion to mucoidy of *Pseudomonas aeruginosa*. The present invention also provides a molecular mechanism for the conversion from the nonmucoid to the mucoid state, including specific sequence alterations that occur in the mucA gene that cause the conversion and molecular probes for the early detection of this disease state.

"Recombinant," as used herein, means that a protein is derived from recombinant (e.g., microbial) expression systems. "Microbial" refers to recombinant proteins made in bacterial or fungal (e.g., yeast) expression systems. As a product, "recombinant microbial" defines a protein produced in a microbial expression system which is essentially free of native endogenous substances. Protein expressed in most bacterial cultures, e.g., E. coli, will be free of glycan.

"Biologically active," as used throughout the specification means that a particular molecule shares sufficient amino acid sequence similarity with the embodiments of the present invention disclosed herein to be capable of forming a algU-mucA-mucB complex, thereby repressing gene transcription from the algD promoter.

"DNA sequence" refers to a DNA polymer, in the form of a separate fragment or as a component of a larger DNA construct. Preferably, the DNA sequences are in a quantity or concentration enabling identification, manipulation, and recovery of the sequence and its component nucleotide sequences by standard biochemical methods, for example, using a cloning vector. Such sequences are preferably provided in the form of an open reading frame uninterrupted by internal nontranslated sequences. Genomic DNA containing the relevant sequences could also be used. Sequences of non-translated DNA may be present 5' or 3' from the open reading frame, where the same do not interfere with manipulation or expression of the coding regions.

"Nucleotide sequence" refers to a heteropolymer of deoxyribonucleotides. DNA sequences encoding the proteins provided of this invention can be assembled from cDNA fragments and short oligonucleotide linkers, or from series of oligonucleotides, to provide a synthetic gene which is capable of being expressed in a recombinant transcriptional unit.

"Recombinant expression vector" refers to a replicable DNA construct used either to amplify or to express DNA which encodes the fusion proteins of the present invention and which includes a transcriptional unit comprising an assembly of (1) a genetic element or elements having a regulatory role in gene expression, for example, promoters or enhancers, (2) a structure or coding sequence which is transcribed into mRNA and translated into protein, and (3) appropriate transcription and translation initiation and termination sequences. Structural elements intended for use in yeast expression systems preferably include a leader sequence enabling extracellular secretion of translated protein by a host cell. Alternatively, where recombinant protein is expressed without a leader or transport sequence, it may include an N-terminal methionine residue. This residue may optionally by subsequently cleaved from the expressed recombinant protein to provide a final product.

"Recombinant microbial expression system" means a substantially homogeneous monoculture of suitable host microorganisms, for example, bacteria such as E. coli or yeast such as S. cerevisiae, which have stably integrated a recombinant transcriptional unit into chromosomal DNA or carry the recombinant transcriptional unit as a component of a resident plasmid. Generally, cells constituting the system are the progeny of a single ancestral transformant. Recombinant expression systems as defined herein will express heterologous protein upon induction of the regulatory elements linked to the DNA sequence or synthetic gene to be expressed.

The present invention provides a composition of matter comprising a first polynucleotide having the sequence of SEQ ID NO:10, a second polynucleotide complementary to the first polynucleotide or a polynucleotide differing from the first or second polynucleotide by codon degeneracy. Also claimed is a polynucleotide which hybridizes with the first or second polynucleotide, or an oligonucleotide probe for the first or second polynucleotide which hybridizes with said polynucleotide.

A further composition of matter of the present invention is a *Pseudomonas aeruginosa* mucA or mucB gene in substantially pure form. The mucA gene is defined as substantially comprising the sequence of FIG. 2 (SEQ ID NO:10) defined further as excluding the mucB coding region. Also claimed is a mucA gene defined further as differing from having an altered sequence. The alteration may be an insertion or deletion of at least one nucleotide, it may be a frameshift mutation, or a nonsense mutation. Alteration of the gene results in an inactive mucA gene product. In a preferred embodiment of the invention, the altered gene sequence has a deletion of nucleotide "A" from position 371 of the sequence of FIG. 2. In an alternatively preferred embodiment of the invention, the altered gene sequence has a deletion of nucleotide "G" from position 440 of the sequence of FIG. 2. In also a preferred embodiment of the invention, the altered gene sequence has an alteration of nucleotide "C" from position 362 of the sequence of FIG. 2.

The polynucleotide may be a polydeoxyribonucleotide or a polyribonucleotide. The oligonucleotide may be an oligodeoxyribonucleotide or an oligoribonucleotide. A further composition of matter is an oligonucleotide useful as a probe for and which hybridizes with the polynucleotide sequence of FIG. 2 or sequence alterations thereof. A preferred embodiment of the invention is an oligonucleotide comprising a sequence complementary to a region spanning the deletion at position 371. In particular, the oligonucleotide comprises the sequence 5'-GGGACCCCCCGCA-3' (SEQ ID NO:2). The altered sequence of the mucA gene may have a deletion of the nucleotide "G" from position 439 or 440. One skilled in the art would see that since there is a "G" in both positions 439 and 440 it is not possible to know which "G" is deleted in this altered sequence.

A further embodiment of the present invention is an oligonucleotide comprising a sequence complementary to a region spanning the deletion at position 439 or 440. In particular, this oligonucleotide comprises the sequence 5'-GAGCAGGGGCGCC-3' (SEQ ID NO:3).

A further composition of matter of the present invention is a mucA gene having an altered sequence wherein the altered sequence is an insertion of nucleotides 5'-CAGGGGGC-3' between positions 433 and 434. Also claimed is an oligonucleotide comprising a sequence complementary to a region spanning the insertion of the nucleotides 5'-CAGGGGGC-3'. A preferred embodiment is an oligonucleotide comprising 5'-CAGGGGGCCAGGGGGC-3' (SEQ ID NO:4).

A further embodiment of the present invention is the use of these compositions of matter for a method of detecting conversion to mucoidy in *Pseudomonas aeruginosa* comprising detecting a loss of mucA or mucB function. In particular, a method of detecting conversion to mucoidy in *Pseudomonas aeruginosa* having an inactive mucA gene product comprising the detection of an altered sequence in the mucA gene is claimed. A preferred embodiment is a method of detecting conversion to mucoidy in *Pseudomonas aeruginosa* having an inactive mucA gene product comprising the detection of an altered sequence in the mucA gene. In this case, the altered sequence encodes an inactive product and the altered sequence is detected by hybridization with a complementary oligonucleotide. The complementary oligonucleotide may be 5'-GGGACCCCCCGCA-3', 5'-GAGCAGGGGCGCC-3', or 5'-CAGGGGGCCAGGGGGC-3' (SEQ ID NOS:2–4). One skilled in the art could see that an altered sequence may comprise nucleotide changes, insertions, deletions or changes in the sequence leading to a nonsense or stop codon anywhere within this locus between about positions 300 and 500 of the sequence of FIG. 2.

A further embodiment of the present invention is a method of detecting conversion to mucoidy in *Pseudomonas aeruginosa* having an inactive mucA gene comprising the steps of: 1) obtaining *Pseudomonas aeruginosa* suspected of conversion to mucoidy to provide a test sample, and 2) hybridizing the test sample with an oligonucleotide 5'-GGGACCCCCCGCA-3', 5'-GAGCAGGGGCGCC-3', or 5'-CAGGGGGCCAGGGGGC-3' (SEQ ID NOS:2–4). Positive hybridization indicates conversion to mucoidy in *Pseudomonas aeruginosa*:

A further embodiment of the present invention is a *Pseudomonas aeruginosa* algU gene in substantially pure form. The algU gene comprises the sequence of FIG. 1.

The DNA sequences disclosed herein will also find utility as probes or primers in nucleic acid hybridization embodiments. As such, it is contemplated that oligonucleotide fragments corresponding to the sequence(s) of seq id no:1–14 and 20–23. For stretches of between about 10 nucleotides to about 20 or to about 30 nucleotides will find particular utility, with even longer sequences, e.g., 40, 50, 100, even up to full length, being more preferred for certain embodiments. The ability of such nucleic acid probes to specifically hybridize to algU, mucA and mucB-encoding sequences will enable them to be of use in a variety of embodiments. For example, the probes can be used in a variety of assays for detecting the presence of complementary sequences in a given sample. However, other uses are envisioned, including the use of the sequence information for the preparation of mutant species primers, or primers for use in preparing other genetic constructions.

Nucleic acid molecules having stretches of 10, 20, 30, 50, or even of 100 nucleotides or so, complementary to seq id no:1–14, 20–23, will have utility as hybridization probes. These probes will be useful in a variety of hybridization embodiments, such as Southern and Northern blotting in connection with analysing the complex interaction of structural and regulatory genes in diverse microorganisms and in clinical isoltaes from CF patients. The total size of fragment, as well as the size of the complementary stretch(es), will ultimately depend on the intended use or application of the particular nucleic acid segment. Smaller fragments will generally find use in hybridization embodiments, wherein the length of the complementary region may be varied, such as between about 10 and about 100 nucleotides, or even up to full length DNA insert of SEQ ID NOS:1–14, 20–23, according to the complementary sequences one wishes to detect.

The use of a hybridization probe of about 10 nucleotides in length allows the formation of a duplex molecule that is both stable and selective. Molecules having complementary sequences over stretches greater than 10 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 20 nucleotides, or even longer where desired. Such fragments may be readily prepared by, for example, directly synthesizing the fragment by chemical means, by application of nucleic acid reproduction technology, such as the PCR technology of U.S. Pat. No. 4,603,102 (herein incorporated by reference) or by introducing selected sequences into recombinant vectors for recombinant production.

Accordingly, the nucleotide sequences of the invention may be used for their ability to selectively form duplex molecules with complementary stretches of homologous, or heterologous genes or cDNAs. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and\or high temperature conditions, such as provided by 0.02M–0.15M NaCl at temperatures of 50° C. to 70° C. Such selective conditions tolerate little, if any, mismatch between the probe and the template or target strand, and would be particularly suitable for isolating functionally related genes.

Of course, for some applications, for example, where one desires to prepare mutants employing a mutant primer strand hybridized to an underlying template or where one seeks to isolate specific mutant algU, mucA or mucB-encoding sequences from related species, functional equivalents, or the like, less stringent hybridization conditions will typically be needed in order to allow formation of the heteroduplex. In these circumstances, one may desire to employ conditions such as 0.15M–0.9M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, calorimetric indicator substrates are known which can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

Longer DNA segments will often find particular utility in the recombinant production of peptides or proteins. DNA segments which encode peptide antigens from about 15 to about 50 amino acids in length, or more preferably, from about 15 to about 30 amino acids in length are contemplated to be particularly useful, as are DNA segments encoding entire algU, mucA or mucB proteins. DNA segments encoding peptides will generally have a minimum coding length in the order of about 45 to about 150, or to about 90 nucleotides.

The nucleic acid segments of the present invention, regardless of the length of the coding sequence itself, may be combined with other DNA sequences, such as promoters, additional restriction enzyme sites, multiple cloning sites, other coding segments, and the like, such that their overall length may vary considerably. It is contemplated that a nucleic acid fragment of almost any length may be employed, with the total length preferably being limited by the ease of preparation and use in the intended recombinant DNA protocol. For example, nucleic acid fragments may be prepared in accordance with the present invention which are up to 10,000 base pairs in length, with segments of 5,000 or 3,000 being preferred and segments of about 1,000 base pairs in length being particularly preferred.

It will be understood that this invention is not limited to the particular nucleic acid and amino acid sequences of seq id nos:1–23. Therefore, DNA segments prepared in accordance with the present invention may also encode biologically functional equivalent proteins or peptides which have variant amino acids sequences. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged.

DNA segments encoding a algU, mucA or mucB gene may be introduced into recombinant host cells and employed for expressing a algU, mucA or mucB structural or functionally related protein. Alternatively, through the application of genetic engineering techniques, subportions or derivatives of selected algU, mucA or mucB genes may be employed. Equally, through the application of site-directed mutagenesis techniques, one may re-engineer DNA segments of the present invention to alter the coding sequence, e.g., to introduce improvements to the antigenicity of the protein or to test algU, mucA or mucB mutants in order to examine transcription from the algD or related promoter activity at the molecular level. Where desired, one may also prepare fusion peptides, e.g., where the algU, mucA or mucB coding regions are aligned within the same expression unit with other proteins or peptides having desired functions, such as for immunodetection purposes (e.g., enzyme label coding regions).

As mentioned above, modification and changes may be made in the structure of algU, mucA or mucB coding regions and still obtain a molecule having like or otherwise desirable characteristics. As used herein, the term "biological functional equivalent" refers to such proteins. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence (or, of course, its underlying DNA coding sequence) and nevertheless obtain a protein with like or even countervailing properties (e.g., antagonistic v. agonistic). It is thus contemplated by the inventors that various changes may be made in the sequence of algU, mucA or mucB proteins or peptides (or underlying DNA) without appreciable loss of their biological utility or activity.

In still further embodiments, the present invention concerns a method for identifying new compounds that inhibit transcription from the algD promoter, which may be termed as "candidate substances." Such compounds may include anti-sense oligonucleotides or molecule that encourage algU-mucA-mucB mediated repression of the algD promoter. The present invention provides for a method for screening a candidate substance for preventing *P. aeruginosa* conversion to mucoidy comprising: contacting the *E. coli* bacteria as described in Example 6 with an effective amount of a candidate substance; and assaying for reporter gene activity, wherein a decrease in the expression of the reporter gene indicates inhibition of algD promoter activity.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1. DNA sequence (SEQ ID NO:9) of algU. Bent arrows denote the endpoints of deletions: ΔU4/76 suppresses mucoidy and produces P27 (+); U4/33 has no effect on mucoidy and is not capable of producing P27 (−). EcoRV, a site used for insertional inactivation of algU on the chromosome is shown.

FIG. 2A, FIG. 2B and FIG. 2C. The complete nucleotide sequence (SEQ ID NO:10) of mucA and mucB. The open reading frames compatible with the direction of transcription, suppression activity of deletions, and the observed $M_r$ of the mucA gene product [20 kDa (Martin et al., 1992)] and that of the mucB gene product.

FIG. 3A-1 and FIG. 3A-2 Mutations causing mucoidy in *P. aeruginosa* in the region of mucA (SEQ ID NO:1) containing mutations causing conversion to mucoidy is shown [dots indicate omitted sequence. Highlighted are nucleotides missing or substituted in mucoid strains (CF1, CF8, CF14, CF23, and PA0578). Arrows indicate duplicated sequence (eight nucleotides) in PAO568 (mucA2). Boxed are termination codons (TGA or TAG) placed in frame with the mucA sequence as a result of muc mutations.

FIG. 9A-1 and FIG. 9A-2. Second site suppressor mutations in algU and pseudoreversion to nonmucoidy. Partial nucleotide sequence (SEQ ID NO:19) of the algU gene from PAO578 (Accession number L02119). Dots, sequences not shown. Highlighted nucleotides: deleted residue (ΔT) or substitution (A below the sequence). Boxed triplets represent stop codons generated or brought in frame with the coding sequence of algU.

DETAILED DESCRIPTION OF THE PREFERRED EMBODIMENTS

Mucoidy in Pseudomonas aeruginosa is a critical virulence factor associated with chronic infections in cystic fibrosis (CF). The initially colonizing strains are nonmucoid but once in the CF lung, they almost inevitably convert into mucoid phenotype. Three tightly linked genes algU, mucA, and mucB have been identified with a chromosomal region shown by genetic means to represent the site where mutations cause conversion to mucoidy. Mutations causing mucoidy occur in mucA. The complete nucleotide sequence of the mucA gene is shown in FIG. 2A, FIG. 2B and FIG. 2C. The positions of mutations in PAO568 (muc-2), PAO578 (muc-22), and CF isolates (CF1, CF14, and CF23) are also indicated in FIG. 2A, FIG. 2B and FIG. 2C. The oligonucleotides designed to detect such mutations by hybridization.

Figure 10A:
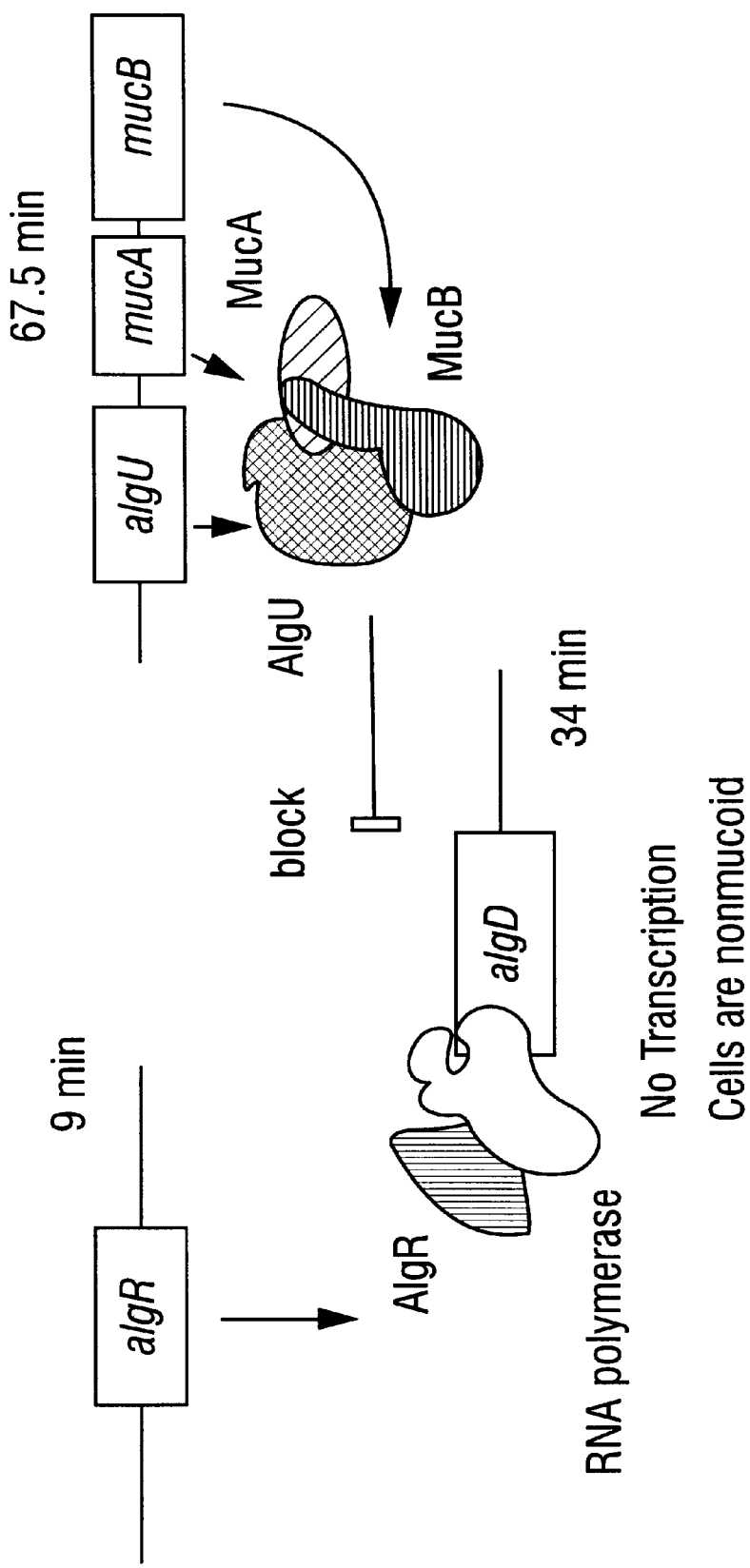
FIG. 10A shows regulatory circuits controlling mucoidy in P. aeruginosa and effects of muc mutations. Under conditions when all genes are complete, MucA and MucB negatively regulate algU. One possibility shown here is that MucA and MucB are complexed with algU. This renders algU inactive or unavailable for transcription of algD the sequestering or inactivity of the sigma factor-like element algU there is no transcription of algD.
Figure 10B:
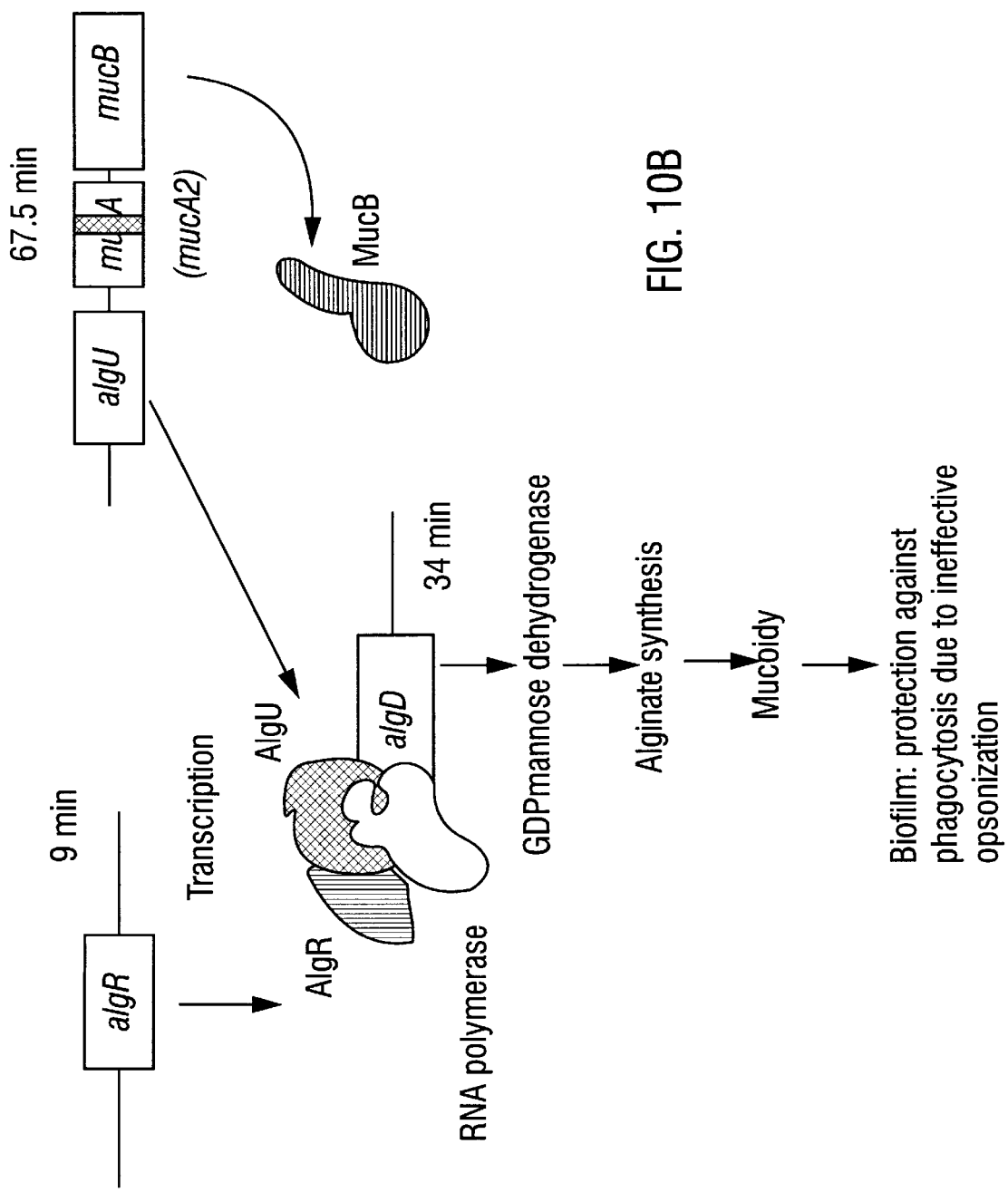
FIG. 10B when mucA is inactivated by a frameshift mutation, algU becomes active and allows initiation of transcription at algD.

The algU gene plays a positive regulatory role in the transcription of algD, a gene encoding GDPmannose dehydrogenase. The algD gene must be expressed at high levels in order for cells to attain mucoid phenotype (FIG. 10A and FIG. 10B) mucA and mucB play a negative regulatory role, and, when active, these genes suppress mucoidy. When either mucA or mucB are inactivated, this results in derepression of algD transcription and conversion to mucoidy (FIG. 10A and FIG. 10B). The present inventors have isolated, sequenced, and characterized the entire region containing algU, mucA, and mucB. When a clone of algU, mucA and mucB, isolated from nonmucoid cells, is placed into mucoid derivatives of the standard genetic strain PAO and in CF isolates, it can cause suppression of mucoidy, viz. the cells become phenotypically nonmucoid and the algD promoter is silenced. Using gene replacements on the chromosome and phage-mediated generalized transduction, the present inventors have shown that algU and the downstream genes described here as mucA and mucB map at about 67.5 minutes on the P. aeruginosa chromosome. These genetic markers represent a site where mutations causing conversion from nonmucoid to mucoid phenotype occur, and have not been previously isolated or characterized. Mutations (deletions and insertions) causing frameshift mutations and premature termination of the mucA open reading frame have been identified through the work described herein.

Even though the invention has been described with a certain degree of particularity, it is evident that many alternatives, modifications, and variations will be apparent to those skilled in the art in light of the foregoing disclosure. Accordingly, it is intended that all such alternatives, modifications, and variations which fall within the spirit and the scope of the invention be embraced by the defined claims.

Even though the invention has been described with a certain degree of particularity, it is evident that many alternatives, modifications, and variations will be apparent to those skilled in the art in light of the foregoing disclosure. Accordingly, it is intended that all such alternatives, modifications, and variations which fall within the spirit and the scope of the invention be embraced by the defined claims.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Characterization of a Locus Determining the Mucoid Status of Pseudomonas aeruginosa: algU Shows Sequence Similarities with a Sigma Factor from Bacillus Several genetic studies have indicated that muc loci have the property to affect mucoidy when present in trans. For example, it has been observed that R' derivatives of R68.45, which carry pruAB$^+$ and an adjacent muc locus from a nonmucoid PAO strain, are capable of switching off (suppressing) alginate production in mucoid strains PAO568, PAO578, and PAO581 (Fyfe, 1985). This effect appeared to be specific since another mucoid PAO derivative, strain PAO579, was not affected (Fyfe, 1985). This suggested to the present inventors that changes in mucoidy could be used as a screening tool to clone and isolate additional regulatory genes. A generation of a comprehensive genomic library from P. aeruginosa has been reported previously (Ratnaningsih et al., 1990). Several cosmids from this library have been successfully used for construction of a combined physical and genetic map of P. aeruginosa PAO (Ratnaningsih et al., 1990). This cosmid library was constructed in pLA2917 (which can replicate in P. aeruginosa) using DNA from a derivative of the strain PAO1 (nonmucoid) (Holloway, 1955; Ratnaningsih et al., 1990). The library was introduced into several mucoid strains by conjugation and ten independent and nonoverlapping clones capable of altering the mucoid character were isolated: pMO010533, pMO010921, pMO011021, pMO011537, pMO011644, pMO011744, pMO011801, pMO011809, pMO011920, and pMO012046. Two of the clones had previously been described as carrying other genetic markers (Ratnaningsih et al., 1990). pMO011809 contains hisI and has been used to demonstrate that this locus resides on the SpeI fragment E in the late region of the chromosome (Ratnaningsih et al., 1990). In the same study, pMO011644 was shown to carry the oruI gene, also mapping in the late region of the chromosome, but hybridizing to a different SpeI fragment. One of the clones, pMO012046, rendered a significant number of strains completely nonmucoid, and was chosen for further study. The locus affecting alginate production on this chromosomal fragment was designated algU.

Media and bacterial growth

E. coli was grown on LB supplemented with 10 μg/ml tetracycline (Tc), 40 μg/ml ampicillin (Ap), and 25 μg/ml kanamycin (Km) when required. P. aeruginosa was grown on LB, minimal media (Deretic et al., 1990; Meile et al., 1982), and Pseudomonas isolation agar (PIA) (DIFCO). The nitrogen free medium (P), used to test the ability to utilize proline (supplemented at the concentration of 20 mM) as the sole carbon and nitrogen source, has been previously described (Meile et al., 1982). Other amino acids were supplied as 1 mM when necessary. Media for environmental modulation by different nitrogen sources (nitrate or ammonia) have been described previously (Deretic et al., 1990; Mohr et al., 1990). 300 mM NaCl was added to LB when required (Deretic et al., 1990). Antibiotics supplements for P. aeruginosa were: 300 μg/ml Tc for PIA, 50 μg/ml Tc for LB and minimal media, and 300 μg/ml carbenicillin (Cb) for all media.

Plasmids and bacterial strains

Strains of P. aeruginosa and plasmids used in this study are shown in Table 1.

TABLE 1

Bacterial strains, plasmids, and bacteriophages

| Species, strain, plasmid, or phage | Relevant properties[a] |
|---|---|
| P. aeruginosa | |
| PAO1 | prototroph Alg$^-$ |
| PAO1293 | prototroph Alg$^-$ |
| PAO568 | FP2$^+$ muc-2 (Alg$^{+i}$) leu-38 |
| PAO578 | FP2$^+$ muc-22 (Alg$^+$) leu-38 |
| PAO579 | FP2$^+$ muc-23 (Alg$^+$) leu-38 |
| PAO581 | FP2$^+$ muc-25 (Alg$^+$) leu-38 |
| PAO540 | cys-5605 his-5075 argA171 Alg$^-$ |
| PAO669 | FP2$^+$ muc-2 (Alg$^{+i}$) leu-38 Cb$^r$ algD$^+$ algD::xylE (Derived from PAO568) |
| PAO670 | FP2$^+$ algU::Tc$^r$ (Alg$^-$) (Derived from PAO568) |
| PAO964 | pru-354 ami-151 hut C107 Alg$^-$ |
| PAM425 | muc-3739 (Alg$^+$) lys-13 |
| Plasmids | |
| pLA2917 | IncP1 mob$^+$ tra cos$^+$Tc$^r$ Km$^r$ |
| pCMob | ColE1 mob$^+$ (RK2) tra cos$^+$ Ap$^r$ (Cb$^r$) Tc$^r$ |
| pSF4 | Ori (p15A) mob$^+$ (RK2) cos$^+$ Tc$^r$ |
| pRK2013 | ColE1 mob$^+$ tra$^+$ (RK2) Km$^r$ |
| pT7-5 | ColE1 Ap$^r$φ10 promoter-EcoRI-polylinker-HindIII |
| pT7-6 | ColE1 Ap$^r$φ10 promoter-HindIII-polylinker-EcoRI |
| pGP1-2 | Ori (p15A) P$_L$T7 gene 1 (T7 RNA polymerase) P$_{lac}$-cI857 Km$^r$ |
| pVDZ'2 | IncP1 mob$^+$ tra lacZ' (lacZ__) Tc$^r$ |
| pCMR7 | algR as 827 bp HindIII-BamHI in pT7-6 |
| pPAOM3 | pVDX18 IngQ/P4 algD::xylE Ap$^r$ (Cb$^r$) |
| pMO011809 | hisI$^+$ (cosmid clone in pLA2917) |
| pMO012046 | algU$^+$ (cosmid clone in pLA2917) |
| pDMU1 | algU$^+$ (a 6 kb HindIII-EcoRI fragment from pMO012046 subcloned on pVDZ'2) |
| pDMU4/76 | algU$^+$as Δ4/76 subcloned on pVDZ'2 |
| pRCW1 | a 6 kb HindIII-NsiI subclone from the cosmid pMO011809 |
| pDMU100 | pUC12 mob$^+$ algU::Tc$^r$ Ap$^r$ (Cb$^r$) |
| pDMDX | pCMobB algD::xylE mob$^+$ Ap$^r$ (Cb$^r$) |
| Phages | |
| F116L | Generalized transduction phage |

[a]Alg$^{+i}$, inducible production of alginate resulting in mucoid phenotype (Deretic et al., 1990). Alg$^+$, mucoid phenotype, Alg$^-$, nonmucoid phenotype.

Strains PAO669 and PAO670 were derivatives of P. aeruginosa PAO568 (muc- 2). The strain PAO669 was generated by integration of a nonreplicative plasmid carrying an algD::xylE fusion on the chromosome of PAO568. An 11.5 kb HindIII fragment carrying algD with xylE inserted in the XhoI site of algD, was cloned in the HindIII site of pCMobB (Mohr and Deretic, 1990), and the resulting plasmid pDMDX conjugated into PAO568. pCMobB and its derivative pDMDX cannot replicate in Pseudomonas but can be effectively mobilized into this bacterium (Mohr and Deretic, 1990). Cb$^r$ exconjugants were obtained and tested for the presence of other plasmid markers [development of a yellow color when sprayed with a solution of catechol (Konyecsni and Deretic, 1989)] and insertions on the chromosome verified by Southern blot analysis. The strain PAO669 was mucoid and produced alginate on inducing media. PAO670, a strain used to determine effects of the inactivation of algU on the chromosome, was constructed by gene replacement of the chromosomal algU with an insertionally inactivated algU (algU::Tc$^r$). This was accomplished as follows: A 2.4 kb HindIII-EcoRI fragment from ΔU4/76 was inserted into pUC12. The resulting construct was digested with EcoRV, and NotI linkers were added. A NotI modified Tc$^r$ cassette (Ishimoto and Lory, 1989) was inserted, and the resulting plasmid digested with EcoRI. Into this site an 1.4 kb EcoRI fragment with mob from pCMobA (originating from pSF4) (Mohr and Deretic, 1990; Selvaraj et al.) was inserted to produce pDMU100. This plasmid was transferred into P. aeruginosa PAO568 by conjugation and exconjugants selected on PIA supplemented with Tc. Since pUC12 and its derivative pDMU100 cannot replicate in Pseudomonas, Tc$^r$ strains had this plasmid integrated on the chromosome via homologous recombination. Double crossover events were identified as Tc$^r$Cb$^s$ strains, chromosomal DNA extracted, digested with appropriate enzymes, and gene replacements verified by Southern blot analysis. CF strains were from a combined collection of mucoid isolates from CF patients in Edinburgh, Scotland, and San Antonio, Tex. Cosmid clones not shown in Table 1 are described in Results. The source of regA was a 1.9 kb PstI-XhoI subclone in mp18 (Hindahl et al., 1988).

The use of E. coli strains for subcloning in pVDZ2 (JM83), triparental conjugations (HB101 harboring pRK2013), and deletion subcloning (WB373) has been described elsewhere (Deretic and Konyecsni, 1989; Konyecsni and Deretic, 1989).

Nucleic acids manipulations and recombinant DNA methods

All DNA manipulations and Southern blot analyses were according to the previously published methods (Deretic and Konyecsni, 1989; Konyecsni and Deretic, 1990; Mohr et al., 1990; Ratnaningsih et al., 1990) or standard recombinant DNA procedures (Ausubel et al., 1989). Radiolabeled probes (Ausubel et al., 1989) were generated using random priming labeling method and [α-$^{32}$P]dCTP (3,00 Ci/mmol; DuPont NEN). RNA extraction and S1 nuclease analysis have been previously published (Deretic and Konyecsni, 1989; Konyecsni and Deretic, 1990). The construction of the cosmid clone library has been reported (Ratnaningsih et al., 1990). Overlapping deletions of the clones in M13 were generated as previously described (Deretic and Koonyecsni, 1989). DNA was sequenced by a modification of the chain termination method with the substitution of dGTP by its analog 7-deaza-dGTP to avoid compressions as previously described (Konyecsni and Deretic, 1990), and using 17 bp or custom made primers when needed. Similarity searches were performed using FASTA program (Pearson and Lipman, 1988) and GenBank databases, as well as through NBRF-PIR protein identification resource network server.

Genetic methods

Clones made in broad host-range plasmids (pVDX18 and pVDZ'2) were transferred into P. aeruginosa by triparental filter matings as described previously (Konyecsni and Deretic, 1989), using E. coli harboring pRK2013 as the helper. Cosmid clones were mobilized into P. aeruginosa from E. coli S17-1 (Simon et al., 1983) as previously reported (Ratnaningsih et al., 1990). Generalized transduction using F116L (Krishnapillai, 1971) was performed as follows: Serially diluted (to achieve near confluency) single plaque preparations of F116L were grown mixed with the donor strain in top agar for 17 h at 37° C. The top agar was scraped and phage eluted in equal volume of TNM (10 mM Tris-HCl pH 7.4, 150 mM NaCl, 10 mM MgSO$_4$), centrifuged at 9000 rpm in SM24 rotor, and supernatant filtered through a 0.45 μm membrane to generate transducing phage stock (used within one month). 500 μl of freshly grown overnight recipient cells was incubated with 500 μl of transducing phage stock (diluted to 5×10$^9$; multiplicity of infection 5:1) for 20 min at 37° C. Cells were centrifuged for 1 min in a microcentrifuge and resuspended in 1 ml of TNM. Aliquots were plated on selective media and incubated for 1 to 2 days, strains purified on selective media, and then spot tested for coinheritance of unselected markers.

Enzyme and alginate assays and scoring of suppression of mucoidy

Catechol 2,3-dioxygenase (CDO), the gene product of xylE, was assayed in cell-free sonic extracts as previously described (Konyecsni and Deretic, 1989). The activity was monitored in 50 mM phosphate buffer (pH 7.5)–0.33 mM catechol by following the increase of $A_{375}$ in a Shimadzu UV160 spectrophotometer. The molar extinction coefficient of the reaction product, 2-hydroxymuconic semialdehyde, is 4.4×10$^4$ at 375 nm. Suppression of mucoidy by plasmid borne genes was monitored on PIA plates unless specified otherwise, and the phenotypic appearance of the colonies scored as mucoid or nonmucoid. A control strain harboring the vector without an insert was always used for comparison. Alginate was assayed by a calorimetric method (Knutson and Jeanes, 1976).

Visualization of gene products using T7 RNA polymerase/promoter system

Polypeptides encoded by cloned genes were visualized by expression in E. coli using a temperature-inducible T7 expression system (plasmid vectors pT7-5 and pT7-6 and T7 RNA polymerase encoded by pGP1-2) (Tabor and Richardson) and protein labeling with [$^{35}$S]methionine and [$^{35}$S]cysteine (Expre$^{35}$S$^{35}$S protein labeling mix; 1000 Ci/mmol; DuPont NEN) with previously described modifications (Konyecsni and Deretic, 1990; Mohr and Deretic, 1990). Proteins were separated on 12% sodium dodecyl sulfate-polyacrylamide gels. $^{14}$C-labeled methylated proteins (Amersham) were used as molecular weight standards. The gels were fixed in 10% acetic acid, washed with H$_2$O, impregnated with 1M salicylic acid, and bands representing radiolabeled polypeptides detected by autofluorography at −70° C.

Pulsed-field gel electrophoresis and Southern blot analysis

Localization of genes on the SpeI map of P. aeruginosa PAO was performed by previously published methods (Ratnaningsih et al., 1990; Shortridge et al., 1991). Identification of SpeI fragments was done by comparison to the lambda phage concatameric ladder ranging in size from 48.5 to 582 kb (Ratnaningsih et al., 1990) as well as based on the hybridization to the previously mapped genes (Ratnaningsih et al., 1990; Shortridge et al., 1991).

Nucleotide sequence accession number

The sequence reported here has been deposited in GenBank (accession number LO2119).

RESULTS

Isolation of cosmid clones affecting mucoidy in trans. Deletion mapping of the algU locus In order to facilitate molecular characterization of algU, this locus was examined by deletion mapping. The subcloning of the ability of algU to suppress alginate production and mucoid phenotype was done using the broad host range subcloning vector pVDZ'2 (Deretic et al., 1987). Initially, a 6 kb HindIII-EcoRI fragment from pMO012046 was found to carry the suppressing activity, and was subjected to further deletion mapping. Two series of consecutive overlapping deletions were produced from each end of the 6 kb fragment, using the previously described deletion-subcloning strategy (Deretic and Konyecsni, 1989). Subclones of these deletion products in pVDZ'2 were transferred by conjugation into PAO568, a mucoid derivative of the standard genetic strain PAO (Fyfe and Govan, 1980). The exconjugants were screened for the loss of mucoid character. All deletion clones which retained the suppressing activity caused phenotypically indistinguishable effect; all negative deletions completely lost the ability to affect mucoidy. The activity was delimited to a region demarcated by the endpoints of deletions ΔU4/76 and ΔUM9.

algU has a strain-specific effect on suppression of mucoidy

It has been shown that different mucoid PAO derivatives and clinical CF isolates display significant differences in algD promoter activity and alginate production in response to modulation by environmental stimuli, such as the salt concentration in the medium or growth on nitrate (Deretic et al., 1990). For example, the algD promoter in strains PAO568 and PAO578 is induced by salt or growth on nitrate (Deretic et al., 1990), although the effects differ in magnitude. PAO568 and PAO578 carry muc determinants designated muc-2 and muc-22 (Fyfe and Govan, 1980), respectively, which map close to each other and to pruAB (Fyfe, 1985; Fyfe and Govan, 1983). PAO579 has a different muc locus (designated muc-23) which maps between hisI and proB and displays a completely opposite response to increased salt concentration in the medium when compared to PAO568 and PAO578 (Deretic et al., 1990).

Genetic map of the late region of the *P. aeruginosa* chromosome indicates that the muc loci is linked to the genetic markers pru-70, pruAB, hisI, and proB. muc-2, muc-22, and algU are cotransducible with pruAB (indicated by arcs). muc-25 and muc-3739 map between hisI and pur-70; it is not known whether they are cotransducible with pruAB (indicated by asterisks). The muc-23 marker maps between hisI and proB. The positions of several genetic markers, alg genes and probes used in this study on a physical map (SpeI) of *P. aeruginosa* PAO. The algD gene hybridizes to two SpeI fragments. The genetic map of the late region and the corresponding SpeI fragments are aligned to permit overlaps of markers known to hybridize to a given fragment, but precise relative positions are not known. Probes known to hybridize, or have been shown to hybridize, to a given SpeI fragment.

Another possibly different muc locus is represented by muc-3739 (strain PAM425) (MacGeorge et al.). When the plasmid pDMU1, containing an active algU locus on the 6 kb HindIII-EcoRI insert in pVDZ'2 was introduced into a panel of strains representative of different mucoid PAO derivatives and CF clinical isolates, a specific pattern of suppression of mucoidy was observed (Table 2).

TABLE 2

Strain specific suppression of mucoidy by algU

| Strain[a] | pVDZ'2 | pDMU1 | Plasmid[b] pRCW1 Suppression of mucoidy[c] |
|---|---|---|---|
| PAO568 (muc-2) | − | + | − |
| PAO578 (muc-22) | − | + | − |
| PAO581 (muc-25) | − | + | − |
| PAO579 (muc-23) | − | − | − |
| PAM425 (muc-3739) | − | − | + |
| CF strains | − (18/18)[d] | + (7/18)[e] | + (3/8)[f] |

[a]PAO strains are isogenic mucoid derivatives of *P. aeruginosa* PAO381 carrying different mapped muc markers (Fyfe and Govan, 1980). PAM425 is a cross between PAO and a mucoid clinical *P. aeruginosa* isolate, Ps3739 (MacGeorge et al., 1986); the corresponding muc-3739 locus has been mapped (MacGeorge et al., 1986). CF strains were mucoid *P. aeruginosa* isolates from different cystic fibrosis patients.
[b]pDMU1 is algU from PAO1 cloned as a 6 kb HindIII-EcoRI fragment on the broad host range vector pVDZ'2 (Deretic et al., 1987). pRCW1 is a subclone of a 6 kb HindIII-NsiI fragment (see Results) from pMO011809 in pVDZ'2.
[c]Suppression was scored on PIA supplemented with Tc as + (transition from mucoid to nonmucoid status when harboring the plasmid) or − (the strain remained mucoid when harboring the plasmid).
[d]Of 18 strains tested none were affected by the vector pVDZ'2.
[e,f]Of 18 strains tested (denominator), 7 lost mucoidy when harboring pDMU1; of 8 strains (denominator) in which pRCW1 was introduced, 3 lost mucoidy. The strains affected by pDMU1 were different from those affected by pRCW1, except in one case with variable results. Not all strains tested with pRCW1 were tested with pDMU1 and vice versa.

pDMU1 rendered muc-2, muc-22 and muc-25 strains (PAO568, PAO578, and PAO581) nonmucoid. In contrast, it had no detectable effect on the muc-23 strain PAO579 and a muc-3739 strain (PAM425). It also affected a substantial number of mucoid clinical isolates (7 out of 18 tested). Congruent with these results was the finding that the mucoid phenotype of some of the strains not affected by algU were affected by a different clone. For example, the strain PAM425 which was not affected by pDMU1 lost its mucoid character when pRCW1, containing a 6 kb HindIII-NsiI subclone from the cosmid pMO011809 (Ratnaningsih et al., 1990), was introduced (Table 2). pRCW1 affected 3 out of 8 CF isolates tested. Thus, the CF strains fell into three categories: (i) Those affected by pDMU1, (ii) those affected by pRCW1, and (iii) those not affected by either of the plasmids.

The results presented in this section indicated that: (i) The suppression of mucoidy in trans was strain dependent; (ii) algU affected a significant number of CF isolates; and (iii) there was a correlation between different muc linkage groups and different clones exerting effects.

Two polypeptides, P27 and P20, are encoded by the region affecting mucoidy in muc-2, muc-22, and muc-25 strains Since deletion inactivation of the algU locus from either end had similar effects, suppression of mucoidy was unlikely to be due to the titration of a diffusable factor (e.g. AlgR) by its binding to DNA. Whether this locus had a coding capacity for a possible trans-acting factor was tested by analysis of [$^{35}$S] methionine and [$^{35}$S] cysteine labeled polypeptides encoded by the insert in a T7 expression system. [$^{35}$S] methionine and [$^{35}$S] cysteine labeled polypeptides encoded by different deletion derivatives of the algU region were separated by SDS-polyacrylamide gel electrophoresis and visualized by autofluorography. Two polypeptides, with apparent $M^r$ of 27.5 kDa (P27) and 20 kDa (P20) were observed as encoded by the algU containing DNA fragment. The consecutive deletions were then used to establish the order of genes and their importance for the suppressing activity. Deletions extending from the HindIII end abolished P27 synthesis while not affecting P20, thus establishing the order of genes as P27 followed by P20. The gene encoding P27 was designated algU. Deletion ΔU4/33, which lost the ability to produce P27, but still directed the synthesis of P20, was no longer capable of suppressing mucoidy. Thus, algU was necessary for the activity of this region.

Suppression of mucoidy by algU is exerted at the level of algD transcription

Both algD and algR undergo transcriptional activation in mucoid cells (Deretic and Konyecsni, 1989). The difference in transcription is very profound at the algD promoter, which remains silent in nonmucoid cells and is highly active in mucoid strains (Deretic et al., 1987; Deretic et al., 1990; Deretic and Konyecsni, 1989). algR is transcribed from two promoters, one distal and constitutive (Mohr and Deretic, 1990; Mohr et al., 1990), and the other proximal and induced in mucoid cells (Deretic and Konyecsni, 1989). The present inventors have investigated whether the presence of algU affected transcription of algD and algR. To assay algD transcription under different conditions in the presence of algU on a plasmid, first a transcriptional fusion of algD and xylE was constructed [used as a reporter gene (Konyecsni and Deretic, 1989)] on the chromosome of PAO568. The strain was constructed as a merodiploid for algD, with one intact copy of algD while the other was inactivated due to the fusion with xylE (strain PAO669; for construction details see Materials and Methods).

The parental strain PAO568 (Fyfe and Govan, 1980) has a remarkable feature in that it displays a broad dynamic range of algD expression (Deretic et al., 1990). Both algD transcription and colony morphology (changing from non-mucoid to mucoid) respond dramatically to inducing conditions (high salt concentration in the medium or growth on nitrate) (Deretic et al., 1990). The strain PAO669 retained these properties (since PAO669 was merodiploid for algD it could synthesize alginate). The induction of algD on the chromosome of PAO669 was analyzed to verify the previously established parameters of algD response to environmental conditions (Deretic et al., 1990; Konyecsni and Deretic, 1989; Mohr et al., 1990). The results of xylE fusion assays and phenotypic induction of mucoidy indicated that the chromosomal fusion reacted to environmental modulation in the same manner previously reported for algD-xylE fusions on plasmids (Table 3).

TABLE 3

Effects of plasmid borne algU from PAO1 on algD transcription in the muc-2 background

| Strain and plasmids[a] | Phenotype[b] | CDO (U/mg)[d] Growth conditions[c] | | | |
|---|---|---|---|---|---|
| | | LB | LB + NaCl | NH$_4$ | NO$_3$ |
| | | CDO (U/mg)[d] | | | |
| PAO669 [None] | M | 0.43 (ND) | 2.84 (ND) | 0.22 (±0.02) | 5.69 (±1.19) |
| PAO669 [pVDZ'2] | M | 0.76 (±0.14) | 4.61 (±1.19) | 0.59 (±0.10) | 3.25 (±0.47) |
| PAO669 [pDMU4/76] | NM | 0.39 (±0.08) | 0.40 (±0.08) | 0.20 (±0.03) | 0.20 (±0.02) |

[a]PAO669 is a derivative of PAO568 (muc-2) in which an algD-xylE fusion has been placed on the chromosome. The plasmid pDMU4/76 was constructed by cloning the deletion product ΔU4/76 into pVDZ'2. This plasmid suppresses mucoidy in muc-2, muc-22, and muc-25 PAO derivatives.
[b]Phenotype was scored on inducing media (PIA, LB + NaCl, and NO$_3$).
M, mucoid; NM, nonmucoid.

TABLE 3-continued

Effects of plasmid borne algU from PAO1 on algD transcription in the muc-2 background

| Strain and plasmids[a] | Phenotype[b] | CDO (U/mg)[d] Growth conditions[c] | | | |
|---|---|---|---|---|---|
| | | LB | LB + NaCl | NH$_4$ | NO$_3$ |
| | | CDO (U/mg)[d] | | | |

[c]Growth conditions and media were as previously reported (Deretic et al., 1990). LB + NaCl, LB supplemented with 300 mM NaCl. NH$_4$ and NO$_3$, minimal media with ammonia or nitrate as the nitrogen source, respectively. The composition and the use of these media for algD induction have been previously described (Detetic et al., 1990; Mohr et al., 1990).
[d]Activity of catechol 2,3 dioxygenase (CDO), the xylE gene product, was determined in cell free extracts as previously described (Konyecsni and Deretic, 1989). One unit of CDO is defined as the amount of enzyme that oxidizes 1 μmol of catechol per min at 24° C. ±, standard error; ND, not determined.

When plasmid pDMU4/76, carrying algU and capable of suppressing mucoidy, was introduced into PAO669, this resulted in a complete loss of alginate synthesis and algD transcription. No induction was observed in response to environmental stimuli known to induce algD in PAO568 (Deretic et al., 1990) (Table 3). When PAO669 harboring pDMU4/76, which displayed nonmucoid colony morphology, was transferred to a medium that no longer supplied selective pressure for plasmid maintenance, colonies segregated into outgrowing mucoid and nonmucoid sectors (data not shown). This was accompanied by a loss of the plasmid in mucoid segregants, as evidenced by the loss of Tc$^r$ in such cells. The Tc$^s$ bacteria (devoid of pDMU4/76) had algD activity restored, as indicated by activities of the chromosomal algD- xylE fusion in strains purified from the corresponding sectors. The mucoid segregants grown on PIA showed CDO (the xylE gene product) activities ranging from 1.76–2.01 U/mg, while the nonmucoid strains originating from the same colonies had CDO activities ranging from 0.401–0.445 U/mg of protein in crude cell extracts. The effects of algU on algD was confirmed by S1 nuclease protection analysis of algD mRNA levels (data not shown). The S1 nuclease protection studies also indicated that neither of the algR promoters were affected in PAO568 harboring algU on a plasmid (not shown). These results strongly suggested that the effect of algU on mucoidy was at the level of algD transcription.

Insertional inactivation of the algU locus on the chromosome of PAO568 renders cells nonmucoid and abrogates algD transcription The studies presented in the previous sections were not sufficient to conclude that algU participates in algD promoter regulation under normal circumstances. In order to investigate this possibility, and to explore whether algU is a positive or a negative regulator of algD transcription, this locus on the chromosome was insertionally inactivated. Transposon mutagenesis of algU on a plasmid using Tn5 proved to be uninterpretable, possibly due to the reported instability of Tn5 in Pseudomonas (Goldberg et al., 1990) and was not pursued further. Instead, a Tc$^r$ cassette was inserted into a conveniently located restriction site within the algU region.

These studies were performed as follows: (i) The presence of two closely spaced EcoRV sites was noted in the region where the gene encoding P27 (algU) resided. This was based on the estimated size of the gene needed to encode a 27.5 kDa polypeptide, the detailed mapping of the coding region of algU using T7 expression studies, and was further confirmed by DNA sequence analysis. Since the endpoint of the last positive deletion still producing P27 was located 540 bp upstream from the first EcoRV site, it was concluded that this site must be within the algU coding region. (ii) A suicide plasmid (pDMU100) was constructed (see Materials and Methods) in which the 2.4 kb HindIII-EcoRI fragment from ΔU4/76 was placed on pUC12 which cannot replicate in *P. aeruginosa*. EcoRV sites within the algU insert were converted into NotI specificity, and a Tc$^r$ cassette (Ishimoto and Lory, 1989), modified as a NotI fragment, was inserted. After addition of a DNA fragment with the mob functions to facilitate plasmid mobilization into Pseudomonas (Selvaraj et al.), the final construct (pDMU100) was conjugated into PAO568 and Tcr exconjugants were selected.

These strains were expected to have the plasmid with algU::Tc$^r$ integrated on the chromosome via homologous recombination. Two possible types of recombinants were anticipated: (i) Merodiploids for algU, retaining an active algU copy, which would have an insertion of the entire plasmid as the result of a single cross-over event; and (ii) true gene replacements, products of double cross-overs, in which case the plasmid moiety and the associated markers would be lost. The present inventors have observed in other gene replacement studies using this procedure that double cross-over events on the *P. aeruginosa* chromosome are frequent and that they range from 10% to 70% for various genes studied (unpublished results), obviating in all cases examined the need for a positive selection against markers encoded by the plasmid moiety. In 9 independent samples with algU::Tc$^r$, 1663 Tc$^r$ exconjugants were examined. Of these 29% lost Cb$^r$ encoded by the plasmid moiety, indicative of double cross-over events. All such Tc$^r$Cb$^s$ strains were nonmucoid and did not produce alginate under any of the conditions tested. Most of the colonies with Tc$^r$ and Cb$^r$ markers (results of single cross-over events and thus expected to have a functional copy of algU) were mucoid, while a portion of such strains showed a delayed mucoid phenotype (mucoidy was developing after 3–4 days as compared with 48 hours needed for the parental strain PAO568). Further studies with Tc$^r$Cb$^s$ recombinants using Southern blotting analysis confirmed that these nonmucoid strains had a true gene replacement with the chromosomal copy of algU disrupted by the Tc$^r$ cassette. Moreover, when the mutation in such strains was purified by transduction (using the generalized transducing phage F116L) into the parental strain PAO568, all Tc$^r$ transductants displayed nonmucoid phenotype. One of the algU::Tc$^r$ derivatives characterized in these studies (strain PAO670) was used to investigate algD transcription. This time, the previously characterized algD-xylE fusion plasmid pPAOM3 (Konyecsni and Deretic, 1989) was introduced into PAO670, and algD promoter activity assayed.

TABLE 4

Analysis of algD transcription in PAO670 (algU::Tc$^r$)

| | Growth conditions[b] | | |
|---|---|---|---|
| | PIA | LB + NaCl | NO$_3$ |
| Strain and plasmid[a] | CDO (U/mg)[c] | | |
| PAO568 [pPAOM3] | 12.10 | 11.54 | 10.95 |
| PAO670 [pPAOM3] | 1.02 | 1.85 | 1.40 |

[a]PAO568 (muc-2) is the mucoid parental strain of PAO670. PAO670 has algU insertionally inactivated on the chromsome. Both strains harbored the algD-xylE transcriptional fusion plasmid pPAOM3.

TABLE 4-continued

Analysis of algD transcription in PAO670 (algU::Tc$^r$)

| | Growth conditions[b] | | |
|---|---|---|---|
| | PIA | LB + NaCl | NO$_3$ |
| Strain and plasmid[a] | CDO (U/mg)[c] | | |

[b]PIA is a rich medium on which all mucoid strains, including PAO568, present their mucoid phenotype. Other media induce mucoidy and algD transcription in PAO568 (Deretic et al., 1990) and are defined in Table 3.
[c]CDO, catechol 2,3 dioxygenase. Relative error did not exceed 20%.

These results (Table 4) indicated that inactivation of the algU locus on the chromosome resulted in a loss of algD transcription, and strongly suggested a positive role for algU in algD expression.

Genetic and physical mapping of algU indicates its close linkage or identity with a subset of muc loci Plasmid borne algU showed specific suppression of mucoidy in strains containing muc-2 and muc-22. These and other muc loci have been suggested to participate in the emergence of mucoid strains (Fyfe and Govan, 1980; MacGeorge et al., 1986), although their nature and the mechanism of action have not been studied. Extensive information is available on the linkage of muc to genetic markers within the late region of the PAO chromosome (Fyfe, 1985; Fyfe and Govan, 1980; Fyfe and Govan, 1983; MacGeorge et al., 1986).

Of particular significance is the cotransducibility of muc-2 and muc-22 with the pru-354 marker [a mutation in pruAB, genes required for the utilization of proline as the sole carbon and nitrogen source (Meile et al., 1982)] demonstrated by F116L bacteriophage mediated genetic exchange (Fyfe, 1985; Fyfe and Govan, 1983). This indicates that these muc loci and the pruAB genes are very close, since F116L can transduce regions in the range of one min of the chromosome.

The present inventors proceeded to localize algU on the chromosome: The first approach was based on the recently determined physical map of *P. aeruginosa* PAO (Ratnaningsih et al., 1990); in these studies algU was used as a probe for Southern hybridization analysis of SpeI fragments separated by pulsed field gel electrophoresis. The second approach was to map algU via F116L transduction; in this case the inventors took advantage of having a strain (PAO670) with the algU gene on the chromosome tagged with the Tc$^r$ cassette and monitored the coinheritance of pruAB with Tc$^r$.

The results of the Southern blot analyses with SpeI digested PAO chromosome subjected to separation by pulse field gel electrophoresis. Physical mapping of algU on the chromosome of *P. aeruginosa* was performed by Southern blot hybridization of various probes with PAO1 DNA digested with SpeI. Fragments were separated on agarose gel by pulsed-field electrophoresis, and blotted onto a membrane. The radiolabeled probes were hybridized, autoradiograms obtained, probes stripped of the filter and checked for completeness of the process, and the blot reprobed with a different gene. Probes: algU; regA, a gene that regulates toxin A synthesis; algR, a response regulator controlling algD transcription; algW, a 6 kb HindIII-NsiI fragment from pMO011809, that also affects mucoidy.

Several consecutively applied probes were used to confirm identification of the SpeI fragments. The algU gene hybridized to the 330 kb SpeI fragment (#6, F) known to carry two genetic markers linked to muc-2 and muc-22, viz. pur-70 at 66 min, and pruAB at 67.5 min (Ratnaningsih et al., 1990). This indicated that algU may be close to the muc-2 and muc-22 markers. To explore this possibility, cotransducibility of pruAB with algU::Tcr was tested. The results of transductional crosses between PAO670 [algU::Tc$^r$ on the chromosome of PAO568 (muc-2)] and PAO964 (pru-354), a mutant in pruAB which cannot grow on proline as the sole carbon and nitrogen source, revealed a high degree of coinheritance of pruAB with algU::Tc$^r$ (Table 5).

TABLE 5

Cotransduction of algU and pruAB[a]

| Donor × Recipient | Selected marker[b] | % coinheritance of the unselected marker[c] | |
|---|---|---|---|
| | | Tc$^r$ | Mucoidy |
| PAO670 × PAO964 | pru-354$^+$ | 20.3 | 0 (<0.3%) |
| PAO670 × PAO540 | hisI$^+$ | 0 (9.25%) | 0 (<0.25%) |

[a]F116L transduction was performed using an algU::Tc$^r$ derivative of PAO568 (muc-2) (strain PAO670) as the donor, and PAO964 (pru-354) or PAO540 (cys-5605 his-5075 argA171) as recipients. PAO670 is nonmucoid due to the inactivation of algU by the insertion of Tc$^r$ cassette. PAO964 and PAO540 are nonmucoid.
[b]pru-354 is a mutant allele of pruAB (Meile et al., 1982). PAO964 (pru-354) cannot grow on proline as the sole carbon and nitrogen source. The selection was performed for pruAB$^+$ or hisI as described in Materials and Methods.
[c]pruAB$^+$ transductants (300 colonies) and hisI transductants (400 colonies) were tested for coinheritance of Tc$^r$. Tc$^r$ in transduction crosses originates from algU::Tc$^r$ on the PAO670 chromosome. No strain displayed mucoid character in at least two independent transduction determinations. In a reciprocal study, in which Tc$^r$ was the selected marker, a 50% coinheritance of pruAB$^+$ with Tc$^r$ was observed (not shown).

The % coinheritance of Tc$^r$ with pruAB corresponded closely to the values previously reported for muc-2 and muc-22 (20–49%) (Fyfe, 1985; Fyfe and Govan, 1983). In a control determination, no coinheritance of hisI and Tc$^r$ was observed using the same transducing phage lysates (Table 5). Significantly, no mucoid transductants (expected from the transfer of muc-2) among over 700 colonies examined were observed in these crosses regardless whether the selection was for pru$^+$ or Tc$^r$. This was in sharp contrast with the results obtained with the recipient strain PAO964 and the donor strain PAO568 (muc-2; the strain parental to PAO670). Normally, 49% of the pru$^+$ colonies are mucoid in transductions involving PAO568 and PAO964 (Fyfe, 1985; Fyfe and Govan, 1983). Although PAO568 had the capacity to transfer the muc-2 marker conferring mucoidy upon the recipient cells, its algU::Tc$^r$ derivative PAO670 completely lost this ability. This effect could be attributed to the insertional inactivation of algU in PAO670. These results indicate that algU is in the close vicinity of the muc loci represented by muc-2 and muc-22 and may even be allelic with these determinants.

AlgU shows sequence similarity with SpoOH, a sigma factor required for developmental processes in *Bacillus subtilis*

In order to gain information about the nature and possible function of genetic elements within the algU region, the nucleotide sequence of the DNA region from the endpoint of the deletion ΔU4/76 (the last 5' deletion positive for suppression of mucoidy and synthesis of P27) and extending through one of the EcoRV sites used for insertional inactivation of algU was determined (FIG. 1). An open reading frame was identified within the region defined as algU by deletion and functional mapping. This sequence contained translational initiation signals, conformed with Pseudomonas codon usage (West and Iglewski, 1988), and was in the direction of transcription determined in T7 expression studies.

When a global homology search was performed using the translated sequence of algU with GenBank and NBRF databases, two known proteins showed statistically significant similarity with AlgU: SpoOH from B. licheniformis and B. subtilis. SpoOH is dispensable for growth, and is primarily required for initiation of sporulation and other developmental processes (competence) in *B. subtilis* (Dubnau et al.; Tatti et al., 1989). The sequence similarity observed (24.9% identity over the entire length of both sequences, and the optimized score of 155), although limited, was equivalent to the extent of similarity of sigma$^H$ to other known sigma factors (ranging between 22% and 31% identity with optimized scores between 113 and 145) (Dubnau et al.).

All regions noted in several sequence compilations and alignments of sigma factors (Helmann and Chamberlin, 1988; Lonetto et al., 1992) were represented in the regions of homology between SpoOH and AlgU. The predicted pI of AlgU was 5.315, similar to the pI of SpoOH (5.052–5.146). A relatively low pI is characteristic of sigma factors (Merrick and Gibbins, 1985) and is known to cause anomalous mobility of several members of this class of proteins during SDS-PAGE (Merrick and Gibbins, 1985). This may help explain a discrepancy in the observed electrophoretic mobility corresponding to 27.5 kDa and predicted $M_r$ of AlgU from the sequence (22,194 Da) which is in the range of discrepancies reported for several sigma factors (Merrick and Gibbins, 1985). B. subtilis sigma$^H$ shows electrophoretic mobility corresponding to 30 kDa, while its predicted $M_r$ is 25,331 (Carter and Moran, 1986).

EXAMPLE 2

Differentiation of *Pseudomonas aeruginosa* into the Alginate Producing Form: Inactivation of mucB Causes Conversion to Mucoidy This example further characterizes genes within the chromosomal region at 67.5 min which play a critical role in determining the mucoid status of *P. aeruginosa*. Two new genes within this locus, mucA and mucB, have been identified, characterized, and demonstrated to participate in the control of mucoidy.

Procedures

References cited herein are listed at the end of the specification.

Bacterial strains, plasmids and growth conditions

All strains of Pseudomonas aeruginosa used in this study are derivatives of the standard genetic strain PAO1. PAO671 was generated by the insertional inactivation of mucB (mucB::Tc$^r$) on the chromosome of the nonmucoid parental strain PAO381 (FP2$^+$ leu-38 mucA$^+$ mucB$^+$; Fyfe and Govan, 1980). This was accomplished using a previously described procedure for allele replacement (Martin et al., 1993). A 2.4 HindIII-EcoRI fragment (U4/76) was inserted into pUC12. A BglII fragment containing the Tc$^r$ cassette was cloned into the unique BglII site within the mucB open reading frame. Next a 1.4-kb EcoRI fragment with mob from pCMobA (Mohr and Deretic 1990; Selvaray et al., 1984) was inserted into a unique EcoRI site resulting in pDMB100. This plasmid was transferred by triparental conjugations into PAO381 to generate PAO671, and additionally into three other nonmucoid PAO strains. Exconjugants were selected on PIA supplemented with tetracycline and double crossovers were identified as Tc$^r$ and Cb$^S$. In all cases, Tc$^r$ Cb$^S$ exconjugants were mucoid, while Tc$^r$ Cb$^r$ (single crossovers) were nonmucoid. Gene replacements in Tc$^r$ Cb$^S$ strains (all mucoid) were verified by Southern blot analysis.

*P. aeruginosa* was grown on LB and Pseudomonas Isolation agar (PIA, Difco). Antibiotic supplements for *P. aeruginosa* were 300 μg/ml tetracycline for PIA, 50 μg/ml of tetracycline for LB and 300 μg/ml carbenicillin for all media. *Escherichia coli* was grown on LB supplemented with tetracycline (10 μg/ml), ampicillin (40 μg/ml) and kanamycin (25 μg/ml) when required. All incubation were at 37° C.

Nucleic acid manipulations and recombinant DNA techniques

All recombinant DNA manipulations and Southern blot analysis were carried out using standard procedures (Ausubel et al., 1989; Martin et al., 1993). DNA sequencing was carried out using the United States Biochemical Sequenase kit with 7-deaza GTP.

Labeling and detection of the mucB gene product

The gene product of mucB was specifically labeled and expressed in *E. coli* using a temperature-inducible T7 RNA polymerase/promoter expression system (plasmid vectors pT7-6 or pT7-5 and T7 RNA polymerase encoded by pGP1-2) (Tabor and Richardson 1985). Nascent polypeptides were labeled with [$^{35}$S]methionine and [$^{35}$S]cysteine (Expre$^{35}$S$^{35}$S protein labeling mix; 1,000 Ci/mmol; DuPont NEN). Proteins were separated on a sodium dodecyl sulfate (SDS)-12% polyacrylamide gel. $^{14}$C-labeled methylated proteins (Amersham) were used as molecular weight standards. Gels were fixed in 10% acetic acid, washed with $H_2O$, impregnated with 1M salicylic acid, and bands representing radiolabeled peptides were detected by autofluorography at −70° C.

Phenotypic scoring, enzyme assays and alginate measurements

Suppression of mucoidy by plasmid-borne genes was monitored on PIA plates, and the phenotypic appearance of the colonies was scored as mucoid or nonmucoid. Alginate was assayed as previously described (Knutson and Jeanes, 1976). Various deletion products of the region containing the genes algU, mucA, and mucB were placed in the broad host range vector pVDZ'2 (Martin et al., 1993) and introduced into PAO568 and PAO581 to test their ability to suppress mucoidy. The plasmid pPAOM3 (Cb$^r$; Konyecsni and Deretic 1988), containing an algD::xylE transcriptional fusion, was introduced into PAO671 carrying mucB::Tc$^r$ and the parental strain PAO381 (Table 6) by triparental conjugation (Konyecsni and Deretic, 1988). Cell- free sonic extracts were assayed for catechol 2,3-dioxygenase (CDO) activity using previously described methods (Konyecsni and Deretic 1988). The activity was monitored in 50 mM phosphate buffer (pH 7.5)–0.33 mM catechol by following the increase of $A_{375}$ in a Shimadzu UV160 spectrophotometer. The molar extinction coefficient of the reaction product, 2-hydroxymuconic semialdehyde, is 4.4×10$^4$ at 375 nm. 1 unit of CDO is defined as the amount of enzyme that oxidizes 1 μmol of catechol per min at 24° C.

Results

Complementation of muc-25 requires two genes downstream of algU

Figure 7:
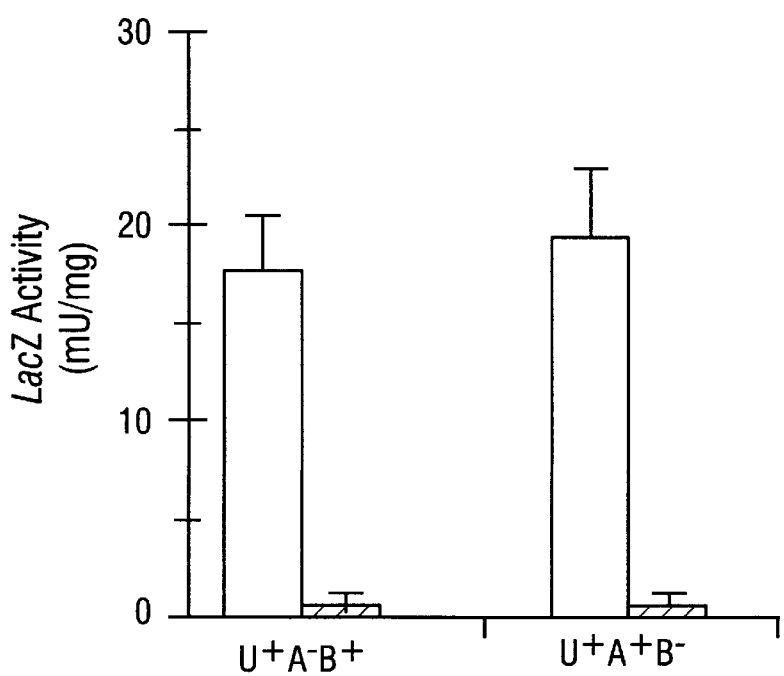
FIG. 7. Suppression of AlgU-dependent algD transcription by in trans complementation of mucA and mucB mutations. The E. coli algD::lacZ transcriptional fusion strain VD1870 harbored plasmids pDM76A (U+A–B+), or pDM76B (U+A+B–). All strains harbored a second plasmid, pMJStac84AB, containing functional but promoterless mucA mucB genes cloned behind the tac promoter on pMJStac84. This plasmid also contains the lacIq gene. Open bars, no IPTG. Filled bars, 1 mM IPTG added to the medium.

The present inventors have discovered that the chromosomal muc mutations can be suppressed to nonmucoidy (Martin et al., 1993). This can be accomplished by in trans complementation with a cosmid clone and its derivatives carrying DNA from a nonmucoid PAO strain (Martin et al., 1993). It has also been shown that this suppression activity was at the level of reducing algD transcription (Martin et al., 1993). The region needed for complementation includes algU, but this process also requires additional sequences downstream of algU (Martin et al., 1993). These studies have also indicated the presence of at least one additional gene, termed mucA, immediately following algU, which encodes a polypeptide (P20) with an apparent $M_r$ of 20 kDa (Martin et al., 1993). algU and mucA are necessary to exert detectable suppression of mucoidy in the PAO568 (muc-2) strain (Fyfe and Govan, 1980). Finer analyses indicated that a region further downstream of mucA was also needed to completely abrogate mucoidy in this strain. Moreover, another isogenic mucoid strain, PAO581, carrying a different muc mutation (muc-25) known to map close to muc-2, was not affected by the DNA fragment containing only algU and mucA unless downstream sequences were included. The present inventors further defined this additional region. The results of these studies are shown in FIG. 7. Based on the size of additional DNA required for the suppression activity, it seemed likely that there was another gene, located downstream of the mucA gene, that was needed for suppression of mucoidy in PAO581. To test this hypothesis it was determined whether a polypeptide product encoded by this DNA region could be detected. T7 expression analysis of mucB expression was studies by separated $^{35}$S labeled polypeptides through, SDS-polyacrylamide gel electrophoresis and visualized by autoradiography. A polypeptide with an apparent $M_r$ of 32.8 kDa (P33) was encoded by the insert required for the suppression of the muc-25 mutation. No polypeptide product was observed when the same inserts were expressed in the opposite direction. However, P33 was expressed relatively poorly when compared to algU and mucA (not shown) (Martin et al., 1993). The gene encoding P33 was designated mucB.

Complete nucleotide sequence of the mucA and mucB genes

In order to further characterize the mucA and mucB genes, the complete nucleotide sequence of this region from the prototype PAO strain PAO1 (nonmucoid), parental to PAO381 and its mucoid derivatives PAO568 and PAO581, was determined. The sequence of algU has been reported previously (Martin et al., 1993). The assignment of open reading frames for mucA and mucB in this region was facilitated by protein expression and other analyses. The only two open reading frames compatible with: (i) the order of genes (mucA followed by mucB); (ii) direction of transcription; (iii) apparent $M_r$ of gene products (P20 and P33); (iv) the endpoints of deletions encroaching on the mucB open reading frame that abrogate the suppression activity in PAO581; and (v) conforming with the codon usage typical of Pseudomonas (West and Iglewski, 1988) are shown in FIG. 2A, FIG. 2B and FIG 2C. The end of the algU gene encoding a polypeptide homologous to sigma factor from Bacillus spp. (Martin et al., 1993) is shown. SD, putative ribosomal binding sites. Stars underneath the sequence, stop codons. The position of the BglII site used to insertionally inactivate much on the *P. aeruginosa* chromosome is shown. The end point of deletion UM9 that does not suppress mucoidy in PAO581 (muc-25) is shown (bent arrow). This deletion still partially suppresses mucoidy in PAO568 (muc-2). These sequence data have been submitted to GenBank (accession numbers LO4794).

The mucA open reading frame, encodes a polypeptide with predicted $M_r$ of 20,997, immediately follows algU. The mucB open reading frame, within the region necessary for suppression of mucoidy in PAO581 encodes a polypeptide with predicted $M_r$ of 34,471 kDa. To further confirm the correct assignment of the genes, this same region was cloned using PCR from several different strains, including PAO381, and in each case the complete nucleotide sequence was determined in multiple PCR clones confirming the one presented in FIG. 2A, FIG. 2B and FIG. 2C.

Insertional inactivation of mucB on the chromosome of the nonmucoid strain PAO381 results in mucoid phenotype Any explanation of the requirement for all three genes (algU, mucA, and mucB) for suppression of mucoidy must take into account that algU plays a positive regulatory role in algD expression, possibly as the sigma factor required for mRNA initiation at the algD promoter (Martin et al., 1993). One of the models compatible with this function of algU in conjunction with the requirement for mucA and mucB (from a nonmucoid strain) to complement muc mutations and suppress mucoidy, is that mucA and mucB counteract the activity of algU and are needed for the maintenance of nonmucoid phenotype. If this is the case, then inactivation of mucB on the chromosome of P. aeruginosa should result in the mucoid phenotype.

To test this hypothesis the mucB on the chromosome of the nonmucoid strain PAO381 was inactivated. This strain is parental to the mucoid derivatives PAO568 (muc-2), and PAO581 (muc-25) that have muc mutations mapping in the same chromosomal region (67.5 min) as the algU-mucAB cluster (Fyfe and Govan, 1980; 1983; Martin et al., 1993). Thus, PAO381 is capable of conversion to mucoidy via mutations in the muc genes. To inactivate mucB, the algU-mucAB cluster was first cloned on pUC12. The conveniently located BglII site (FIG. 2A, FIG. 2B and FIG. 2C) within the coding region of mucB was used to insert a $Tc^r$ cassette (Totten, et al., 1990), resulting in the disruption of mucB, as described in Procedures. To this construct was added a fragment containing mob functions (to facilitate its mobilization into P. aeruginosa), resulting in the plasmid pDMB100. Since pUC12 and its derivative pDMB100 cannot replicate in Pseudomonas, upon a transfer of this plasmid into P. aeruginosa via triparental conjugation (see Procedures), any $Tc^r$ exconjugants must carry this marker integrated on the chromosome. This can occur via homologous recombination involving the algU-mucAB region through single crossover or double crossover events. In the case of single crossovers, the exconjugants are expected to be merodiploids, and should also display $Cb^r$ ($Ap^r$; encoded by the vector moiety); in the case of double crossovers, a true gene replacement is expected to take place with the vector moiety of the plasmid being lost, and thus the resulting strains should be sensitive to carbenicillin ($Cb^S$). Of 129 $Tc^r$ P. aeruginosa exconjugants obtained from 4 independent crosses between E. coli JM83 harboring pDMB100 and PAO381, 28% of exconjugants were $Cb^r$, indicative of a single crossover event. As expected, all such strains were nonmucoid, since they were merodiploids, and contained a functional copy of mucB. These strains were indistinguishable from the parental strain PAO381. In contrast, all $Tc^r$ exconjugants that were $Cb^S$ (72% of total $Tc^r$ exconjugants), thus indicative of double crossover events, became mucoid. Thus, a complete and stable conversion to mucoidy was achieved by inactivating mucB on the chromosome of a previously nonmucoid strain. A true gene replacement event of mucB with mucB::$Tc^r$ on the chromosome of such strains was further confirmed by Southern blot hybridization.

To determine whether inactivation of mucB resulted in transcriptional activation of algD, one such mucB::$Tc^r$ strain (PAO671) was further examined. A plasmid containing algD-xylE transcriptional fusion was introduced into PAO671 and the levels of algD transcription in the parental strain PAO381 (mucB$^+$) and its mucoid derivative PAO671 (mucB::$Tc^r$) were compared.

The results of these studies indicated a 26-fold activation of algD in PAO671 vs PAO381, under identical growth conditions (Table 6). Thus, inactivation of mucB is an event that results in increased algD transcription, alginate overproduction, and the establishment of mucoid phenotype.

TABLE 6

Effects of mucB inactivation on algD promoter activity

| Strain[a] | Phenotype[b] | algD::xylE activity[c] (U/mg of CDO) |
|---|---|---|
| PAO381 (mucB$^+$) | NM | 0.4 |
| PAO671 (mucB::$Tc^r$) | M | 10.5 |

[a]All strains harbored the algD::xylE transcription fusion plasmid pPAOM3 (Konyecsni and Deretic, 1989; Mohr et al., 1990).
[b]Phenotype was scored as mucoid (alginate producing) or nonmucoid after growth for 24 h on PIA.
[c]The activity was expressed as units of catechol 2,3 deoxygenase (CDO; the xylE gene product) per milligram of total protein in crude extracts. Standard error did not exceed 20%. Growth conditions, extract preparation, activity measurements, and unit definitions (see Procedures) are as previously described (Martin et al., 1992; Konyecsni and Deretic, 1989).

The studies presented here demonstrate that inactivation of genes such as mucB can lead to a derepression of the algD promoter and conversion to mucoid (alginate overproducing) status. More importantly, using an isogenic series of strains, different frameshift mutations within the mucAB region that were present in several mucoid strains including CF isolates and absent in the nonmucoid strains have been detected, see Example 3.

A model founded on recently reported evidence (Martin et al., 1993), the results presented in this work, and studies by others (Fyfe and Govan, 1980; 1983; Costerton et al., 1983), is based on the premise that the synthesis of alginate and the emergence of alginate overproducing strains may be a developmental or a cell-differentiation process. Signal transduction involving response regulators such as AlgR and AlgB (Deretic et al., 1989; 1991; Wozniak and Ohman, 1991), nucleoid structure (Deretic et al., 1992; Mohr and Deretic, 1992), and activation of the specific sigma factor(s) (Martin et al., 1993) are most likely different contributing mechanisms for activation of alginate synthesis in natural environments. In the CF lung, while this environment may also be conducive to the induction of the alginate system, due to strong selective pressures (e.g. increased resistance of mucoid forms to phagocytosis, physical clearance mechanisms, antibiotic treatments, etc.) mutants are being selected that overproduce alginate and render cells constitutively mucoid. Such mutants, once extracted from the CF lung, retain mucoid character (Govan, 1988; Martin et al., unpublished results). Mutations in the algU-mucAB region, e.g. inactivation of mucA by frameshift mutations (see Example 3), or mutations affecting mucB activity, represent major pathways for conversion into the mucoid phenotype. Understanding of the principles of signal transduction processes activating the alginate system at several levels, as well as the precise definition of the mutations causing mucoidy in CF strains which is currently in progress, will provide improved diagnostic tools and present potential targets for therapeutic interventions.

EXAMPLE 3

Figure 3B:
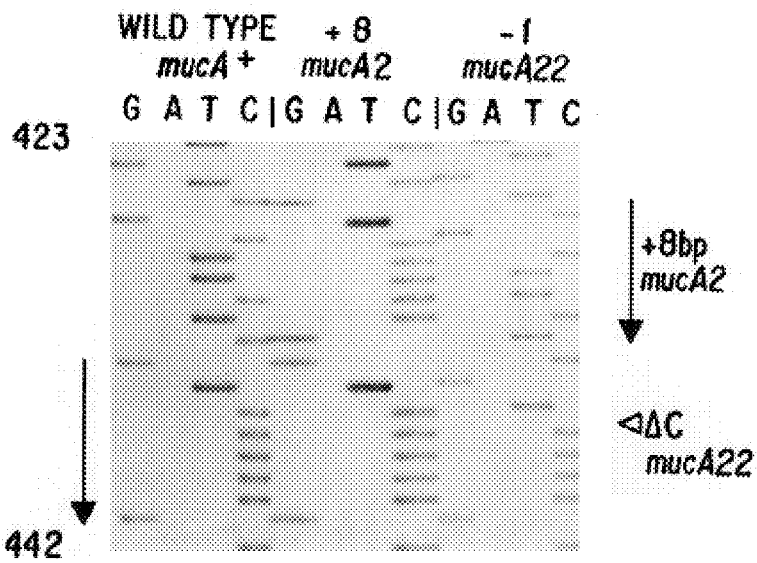
FIG. 3B DNA sequence (from position 423 to 442) of the wild-type mucA⁺, mucA2, and mucA22 alleles. The location of the duplicated sequence in mucA2 (+8 bp) is indicated by arrows; triangle and ▲C denote a missing nucleotide (−1 bp) in mucA22.
Figure 3C:
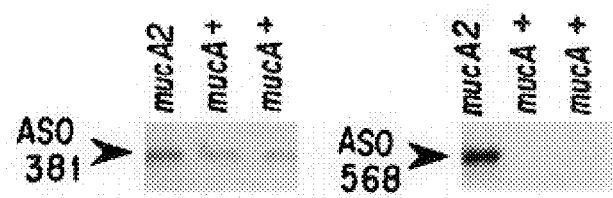
FIG. 3C detection of muc mutations by hybridization with ASOs. PCR-amplified sequences containing mucA from PA0568 (mucA2) and PAO381 (mucA⁺) were blotted onto nitrocellulose membrane and hybridized with ASO 381 or ASO 568. Under the conditions used, ASO 568 hybridizes to mucA2 only while ASO 381 hybridizes to most mucA alleles.

Mechanism of Conversion to Mucoidy in P. aeruginosa Infecting Cystic Fibrosis Patients: Frameshift Mutations of mucA Cause Conversion to Mucoidy In the course of performing gene replacements with algU in the mucoid strain PAO568 (carrying the muc-2 mutation), the present inventors discovered an informative class of recombinants. The gene replacements on the chromosome were carried out via homologous recombination with algU::Tc$^r$ on a plasmid that cannot replicate in Pseudomonas. A set of studies was performed using a deletion that simultaneously removed the 3' end of algU and the 5' end of the downstream gene mucA. Two types of recombinants were expected: (i) Nonmucoid strains containing true gene replacements with inactivated algU (results of double crossovers); and (ii) mucoid strains that were merodiploids (results of single crossovers). As expected, all double crossovers were nonmucoid since they lost a functional algU. The majority of merodiploids were mucoid, since they retained a functional copy of algU. However, a third class of recombinants was also observed which consisted of nonmucoid merodiploids. Since the plasmid DNA came from the nonmucoid strain PAO1, parental to the PAO568 lineage, a plausible explanation for the existence of nonmucoid merodiploids was that the crossover took place between the deletion in mucA on the plasmid and a putative mutation (muc-2) in mucA on the chromosome of the mucoid strain PAO568. Only such a crossover could restore a wild type copy of mucA resulting in nonmucoid merodiploids. The mutation had to be located between the EcoRV site of mucA, where the 5' deletion in the plasmid construct ended, and the 3' end of mucA. In order to test this hypothesis, the present inventors cloned the corresponding region from the strain PAO568 by PCR and determined its complete nucleotide sequence in multiple independent clones. A duplication of 8 nucleotides at position 433 was observed within mucA in all PCR clones from PAO568. The existence of this mutation was further confirmed by hybridization with allele specific oligonucleotides, oligo 381 and oligo 568, to PCR amplified chromosomal sequences from PAO568 (muc-2) and its direct nonmucoid parental strain PAO381 (FIG. 3C). Next, the entire algU-mucAB region was cloned by PCR from PAO568 and its parental strain PAO381, and the complete nucleotide sequence of this region was determined in at least three independent clones. FIG. 3A contains the sequence of the mucA gene and encoded protein. The only difference between PAO381 (muc$^+$) and PAO568 (muc-2) was the octanucleotide duplication in mucA. The present inventors concluded that this was the muc-2 mutation and the mucA allele was designated mucA2. The muc-2 mutation results in a frameshift causing premature termination of mucA at a downstream TGA codon (see FIG. 3A, and Example 5).

Amplification of algU-mucA-mucB sequences and hybridizations with allele specific oligonucleotides The algU-mucA-mucB region was amplified using the following pairs of oligonucleotides: (i) UL5 GCCGCACGT-CACGAGC and UR16 GAGTCCATCCGCTTCG for sequences containing mostly algU and a 5' portion of mucA; and (ii) UL3 CTGTCCGCTGTGATGG and UR12 CGC-CCCTGCTCCTCGA for sequences containing most of mucA and the entire mucB gene. For amplification of genomic sequences, a loopful of bacteria from a *P. aeruginosa* colony was washed in 0.85% saline, centrifuged, resuspended in 500 μl H$_2$O, boiled for 10 min, and stored at −20° until use. One μl of boiled preparations is sufficient to obtain necessary amounts of products for amplification by polymerase chain reaction (PCR). PCR was carried out in 50 μl volumes using standard procedures. Amplification products were tested by electrophoresis on agarose gels. Equal amounts of amplification products were electrophoretically separated on 1% agarose gels and then blotted onto a nitrocellulose filter using standard methods. After the transfer, and crosslinking using UV light (254 nm), blots were prehybridized in 10×SSC, 5×Denhardt solution (without BSA) for at least 30 min. Allele specific oligonucleotides were kinased with $^{32}$p following standard methods, purified using chromatography on Sep-Pak C$_{18}$ columns (Waters) and lyophilized by evaporation in a Savant SpeedVac apparatus. Hybridization with radiolabeled allele specific oligonucleotides was performed in 10 ml of 10×SSC, 5×Denhardt solution for 12 h at 42° C. Membranes were washed 3× for 10 min at 42° C. and autoradiograms taken overnight at −70° C. The blots were boiled for 3 min between hybridizations with different probes.

A simplified version of differential hybridization was also carried out using dot blots. In this case, 5 μl taken directly from the PCR mixture was blotted onto a nitrocellulose or nylon membrane presoaked in 10×SSC, and after denaturation, neutralization, crosslinking (by standard methods or as described above), hybridized and processed as explained for Southern blots.

Results

The present inventors examined whether the allele specific oligonucleotides could be used to screen other mapped muc mutations in PAO and mucoid CF isolates. Although the oligonucleotide probe 568 (specific for the mucA2 allele) did not hybridize with the PCR amplified sequences from several strains, the control oligonucleotide (381) did hybridize but with a reduced intensity relative to PAO381. This suggested that although the tested strains did not have the octanucleotide duplication observed in mucA2, there were other alterations within the region complementary to the oligonucleotide probe. The corresponding regions from several strains hybridizing weakly with the oligonucleotide 381 were cloned and examined. The following strains were included: PAO578 (mucoid derivative of PAO381 with the mutation muc-22 mapping close to muc-2 as determined by transduction) and representative clinical mucoid isolates obtained from different cystic fibrosis patients. Following the procedure outlined for cloning and sequencing of the region encompassing the muc-2 mutation, the corresponding nucleotide sequences in the strain PAO578, and the clinical isolates tested were determined. Instead of the duplication of the octanucleotide sequence in PAO568, there was a deletion of a G residue within a string of 5 Gs within the same general region (see FIG. 3B). Since this was a deletion of one nucleotide, the net result was a similar frameshift as in PAO568, placing the same TGA termination codon in frame with the mucA sequence. The results of these analyses were additionally confirmed by designing an allele specific oligonucleotide designed for this mutation (oligo 578). The mutant allele in PAO578 was designated mucA22.

Figure 3D:
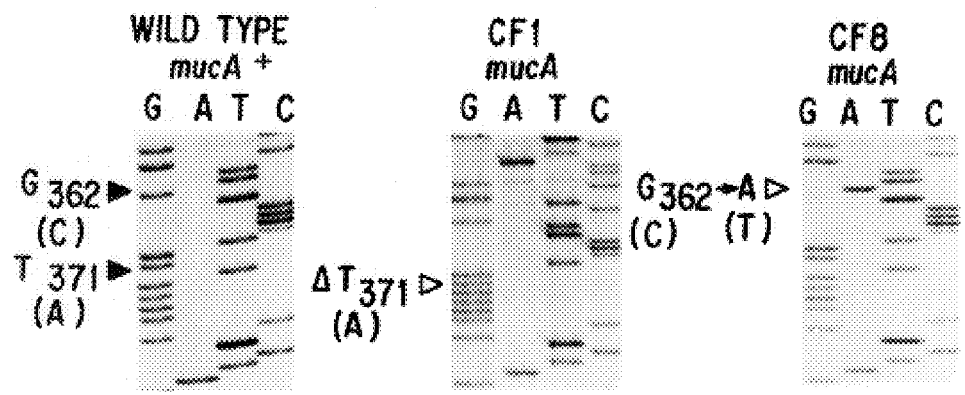
FIG. 3D the sequence of mucA mutations in CF1 (deletion of a nucleotide at 371) (Center) and CF8 (C-362—T-362 transition) (Right) are compared to the wild-type sequence of the nonmucoid strain PAO1 (Left). The antisense strand is shown (nucleotides in parentheses correspond to the residues in A).
Figure 4A:
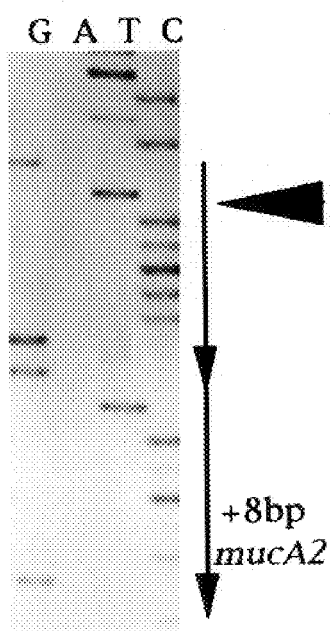
FIG. 4A DNA sequence analysis of gene replacement from the mucoid mucA2 mutation in PAO381a2-3.
Figure 4B:
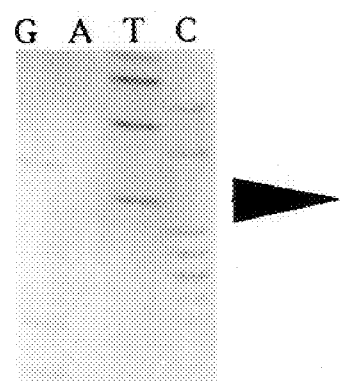
FIG. 4B DNA sequence analysis of gene replacement from the parental non-mucoid strain.
Figure 4C:
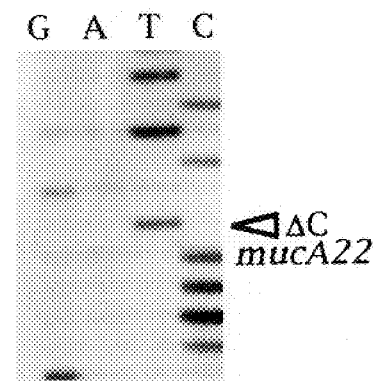
FIG. 4C DNA sequence analysis of gene replacement from the mucoid mucA22 mutation in PAO381a22-1.

Next, the strains that were complemented by plasmids carrying the algU-mucAB region from PAO1 but did not show reduced hybridization with the oligonucleotides were examined. One such cystic fibrosis isolate was subjected to the same cloning and sequencing procedure as outlined above. No changes were detected within the location of the mucA2 and mucA22 mutations. Instead, a deletion of a single nucleotide at the position 371 was detected (see FIG. 3D). This deletion was confirmed by sequencing multiple clones and by hybridizations with an allele specific oligonucleotide CF1. This frameshift mutation also results in a premature termination of mucA although at an upstream termination codon (see FIG. 3A). Another strain, PAO581, that did not show differential hybridization with the allele specific oligonucleotides was also examined. PAO581 carries a muc mutation (muc-25) which has not be mapped by transduction. In this case the present inventors could not find any sequence differences between PAO581 and PAO381 within the region examined here. Similar to PAO581, several mucoid CF strains did not show detectable alterations in mucA.

The work described herein identifies a major site of mutations causing mucoidy in *P. aeruginosa*. The mucA gene and a tightly linked downstream gene, mucB are both required for suppression of mucoidy. When these functions are lost by insertional inactivation on the chromosome of previously nonmucoid strains, provided that the first gene of the cluster (algU) is intact, this results in a strong activation of algD transcription and conversion to mucoidy.

Mucoidy in *P. aeruginosa* has received attention mainly due to its association with CF. However, almost all strains of *P. aeruginosa* have the genetic capacity to synthesize alginate suggesting that this system must play a role in other ecological niches. The vast majority of *P. aeruginosa* biomass in nature exists as the form embedded in the exopolysaccharide biofilm attached to surfaces. It has been shown that *P. aeruginosa* undergoes interconversions between the free floating planktonic form and the sessile form in biofilms, a process which has been viewed as a developmental or cell differentiation phenomenon. Regulation of alginate production by a factor (algU) homologous to an alternative sigma factor SpoOH, controlling the initial stages of development in Bacillus spp. (e.g. sporulation and competence), may reflect the nature of regulatory processes controlling development of biofilms. The genetic data indicate that mucA and mucB suppress the function of algU. There are now ample examples of accessory factors associated with or linked to alternative sigma factors in Bacillus and other organisms that post-translationally modify (e.g. inhibit) their function. By analogy, MucA and MucB may play a similar role. This system, along with signal transduction regulators and histone-like elements, is likely designed to control development of biofilms in response to appropriate environmental cues. Mutations in mucA that lock the system in its constitutive state, which is favorable due to the antiphagocytic properties of the mucoid coating, are being selected in the course of chronic respiratory infection in CF.

In addition to the improved understanding of the molecular mechanisms controlling an important bacterial virulence factor, several aspects of the regulation of mucoidy presented here shed light on developmental processes in Gram negative organisms. The finding that algU shows similarities with a sigma factor specializing in developmental processes of a Gram positive sporulating organism, suggests that bacterial cell differentiation phenomena (e.g. sporulation, biofilm development, and bacterial encystment) may share common regulatory mechanisms.

EXAMPLE 4

Complementation of a mucA Mutation by the Wild-Type mucA Gene Results in Suppression of Alginate Production and Nonmucoid Phenotype Frameshift mutations in mucA, which result in conversion to mucoidy and activation of the algD promoter, suggest a negative regulatory role for the mucA gene product. If this is correct, then it should be possible to complement a mutation in mucA to nonmucoidy by the plasmid-borne wild-type mucA gene. To test this hypothesis, a 852-bp Bst YI fragment containing the mucA gene from the nonmucoid strain PAO1 was cloned behind the tac promoter on the broad-host-range plasmid pVDtac24, resulting in the construct termed "ptac-mucA$^+$." This plasmid also carries the lacI$^q$ gene, which renders tac transcription dependent on the presence of the inducer IPTG. The plasmid was transferred into the mucoid strain PAO568 (mucA2) by triparental conjugation, and exconjugants were examined for colony morphology and alginate production on plates supplemented with 1 mM IPTG or in the absence of the inducer. The colonies grown in the absence of IPTG showed a mucoid morphology identical to that of the parental strain PAO568.

Next the exchange or mucA$^+$ with mucA2 caused activation of algD was examined. Mucoidy is dependent on a strong transcription activation of the algD gene encoding a key biosynthetic enzyme for the mucoid exopolysaccharide alginate. The plasmid pPAOM3 containing an algD::xylE transcriptional fusion was introduced into one such mucoid strain, and the reporter gene activity was determined (Table 7). The results of such measurements indicated that the gene replacement with the mucA2 allele resulted in a 320-fold activation of the algD promoter, which correlated with the levels of alginate production.

TABLE 7

Conversion to mucoidy and activation of algD transcription as a result of gene replacement with the mucA2 allele

| Strain* | Phenotype$^\alpha$ | Alginate production$^\tau$ | algD::xylE activity, units/mg of CDO$^\S$ |
|---|---|---|---|
| PAO381 (mucA$^+$) | NM | <0.1 | 0.14 ± 0.03 |
| PAO381a2–3 (mucA2) | M | 64.9 | 44.9 ± 1.0 |

*For transcriptional fusion measurements, all strains harbored pPAOM3 with an algD::xylE transcriptional fusion. PAO381a2–3 was one of several mucoid isolates generated by exchange of the chromosomal mucA$^+$ in PAO381 with plasmid borne mucA2.
$^\alpha$Phenotype was scored as mucoid (M) or nonmucoid (NM).
$^\tau$Alginate production was expressed in μg of alginate per mg of wet cell weight.
$^\S$Transcriptional activity was expressed as units of catechol 2, 3-deoxygenase (CDO; the xylE gene product) per mg of crude protein extracts ± SEM.

When the same strain harboring ptac-mucA$^+$ was grown in the presence of 1 mM IPTG, it displayed a nonmucoid phenotype. This was accompanied by a decrease in detectable alginate production by a factor of 15 (Table 8).

TABLE 8

Complementation of the mucA2 mutation to nonmucoidy in PAO568 harboring ptac-mucA$^+$

| IPTG | Phenotype | Alginate production, μg/mg of wet cell weight |
|---|---|---|
| — | M | 59.8 |
| 1 mM | NM | 3.6× |

IPTG was used as inducer of tac transcription. M, mucoid; NM, nonmucoid.

These experiments showed that mucoid phenotype can be complemented by a functional mucA gene alone, thus additionally confirming that the observed muc mutations are responsible for mucoid phenotype and that mucA plays a negative regulatory role.

EXAMPLE 5

Detection of mucA Mutations in Mucoid *P. aeruginosa* Isolates from CF Patients

To determine whether similar mutations in mucA occur in mucoid CF isolates, several strains from different patients were tested. Strains previously shown to be complemented with plasmids carrying the algU-mucAB region from PAO1 were examined. Two randomly chosen strains that showed a reduced hybridization with ASO 381 were subjected to PCR and sequence analysis. These strains, CF14 and CF23, displayed a mutation identical to the mucA22 allele (a loss of one G within the string of five G residues in the wild-type mucA), resulting in a premature termination of mucA at the same position as in PAO578.

Next, the strains that did not show reduced hybridization with ASO 381 were examined. One such cystic fibrosis isolate (CF1) was subjected to the same cloning and sequencing procedure as outlined above. No changes were detected within the location of the mucA2 and mucA22 mutations. Instead, a deletion of a single nucleotide at the position 371 was detected (FIG. 3A-1, FIG. 3A-2 and FIG. 3D). This deletion was confirmed by sequencing multiple cones. This frameshift mutation also results in a premature termination of mucA, although at an upstream termination codon (position 396). Another CF strain from this category, CF8, was examined, and a different mutation was observed. There was a transition of C into a T (FIG. 3A-1, FIG. 3A-2 and FIG. 3D) at position 362 of the mucA sequence. Interestingly, this mutation, although not causing a frameshift, generates a stop codon (TAG), known as a nonsense mutation, at this position (FIG. 3A-1, and FIG. 3A-2). These results showed that mutations inactivating mucA, identical or similar to the mucA mutations responsible for conversion of PAO to mucoidy, can be observed in clinical CF isolates.

Strains that can be complemented with algU-mucAB from PAO1 were also found in which no mutation in mucA could be detected in the two general areas where mucA could be detected in the areas where mucA2 (and mucA22) or mutations in CF1 (and CF8) were observed. Similar to these strains, PAO581, a mucoid PAO derivative that carries a muc mutation (muc-25) which has not been mapped by transduction, did not have sequence differences relative to its nonmucoid parent PAO381 within the regions examined here. These results are consistent with the existence of additional types of mutations within the algU-mucAB region or participation of additional sites or processes affecting conversion to mucoidy.

EXAMPLE 6

Functional Analysis in a Heterologous Host and Role in the Instability of Mucoidy In the preceeding examples the present inventors have demonstrated that the conversion to mucoidy is caused by the overproduction of the exopolysaccharide alginate in laboratory and cystic fibrosis strains of *Pseudomonas aeruginosa* that occur via frameshift or nonsense mutations in the second gene of the algU mucA mucB cluster. A model system was developed to characterize novel compounds for use in controlling conversion to mucoidy. To that end, the wild type algU mucA mucB cluster from the standard genetic strain PAO1 was used to reconstitute algD transcription in *Escherichia coli*. Transcription of a algD::lacZ chromosomal fusion in *E. coli* was detected upon introduction of plasmid borne algU mucA mucB. Moreover, when either mucA or mucB were insertionally inactivated, this resulted in further stimulation of transcriptional activity from the algD promoter.

This activation was dependent on algU, since a double algU mucA mutation abrogated transcription of algD. These studies suggest that the phenotypic manifestations of muc mutations, i.e. increased algD expression and mucoid phenotype, depend upon the presence of an active algU gene, and that algU and the downstream factors interact.

Bacterial strains, plasmids, and bacteroiophages

Strains, plasmids, and phages used in this study are shown in Table 1. *P. aeruginosa* strains PAO57874, PAO578160 and PAO57800 were spontaneous nonmucoid derivatives of *P. aeruginosa* PAO578, obtained from initially pure mucoid cultures of PAO578 by repeated passages on Pseudomonas isolation agar (PIA) (DIFCO).

Figure 5A:
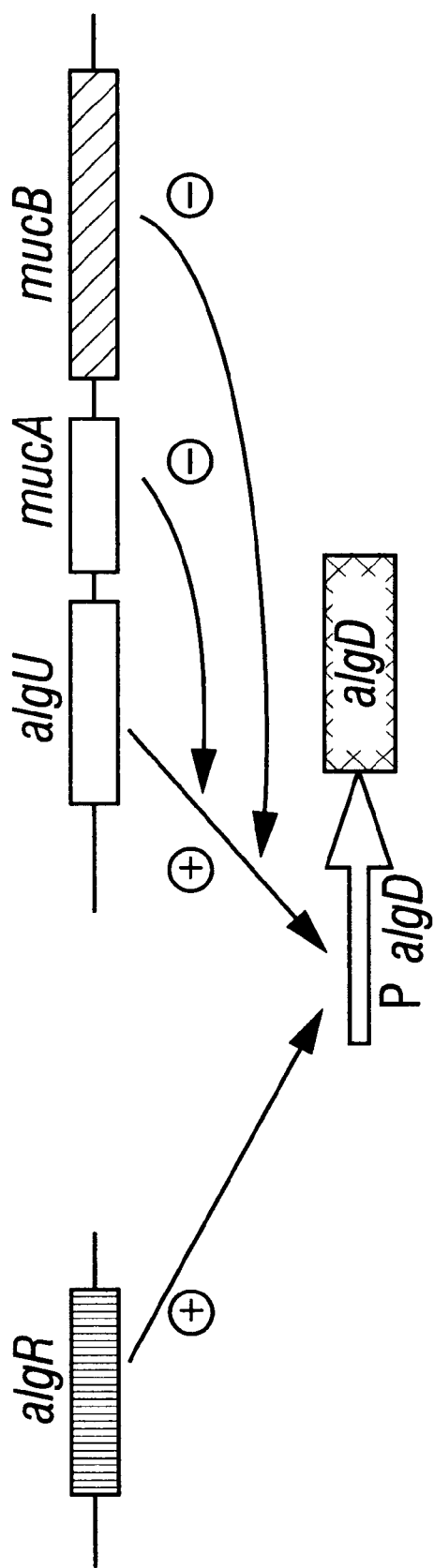
FIG. 5A. Regulatory interactions of algU, mucA, mucB, and algR in the control of the algD promoter (PalgD).

Plasmids pDM76, pDMU76A, pDMU76B, and pDM76UA represent a series of pUC12 derivatives (FIG. 5C) carrying the wild type algU mucA mucB cluster from PAO1, or its insertionally inactivated variants of mucA, mucB, or both algU and mucA, respectively. Plasmid pDMU76UA also has a deletion spanning the region beginning 105 bp upstream of the 3' end of algU, and ending 180 bp downstream of the 5' end of mucA. This deletion was generated by digestion with EcoRV, modification of the ends into the NotI specificity followed by insertion of a NotI linkered tetracycline resistance (Tcr) cassette in this position. Plasmid pDMU76A contained a BglII Tcr cassette inserted into the unique BclI site of mucA. Plasmid pDMU76B contained the same Tcr cassette inserted into the unique BglII site of mucB.

The plasmid vector pMJStac84 was constructed by cloning the 2.45 kb BamH1 fragment (containing the lacIq gene, the tac promoter, and the multiple cloning site from pUC12) from pVDtac24 into the BamHI site of pACYC184. This new vector is based on the p15A replicon, which is fully compatible with ColE1 replicon-based plasmids, and can be used for carrying out studies that require two-plasmid systems. The useful cloning sites are BglII, SmaI, and SstI, in the order of their positions downstream of the tac promoter. The plasmid pMJStac84AB was constructed by cloning the 1.9 kb mucA-mucB containing fragment from PAO1 as BstBI-EcoRI, which was made blunt by incubation with Klenow fragment of DNA polymerase I, into the SmaI site of pMJStac84 in the direction of tac transcription. pMJStac84R was constructed by cloning the 826 bp BamHI algR containing fragment from pCMR7 into pMJStac84.

Media and Bacterial Growth

*E. coli* was grown on LB supplemented with 10 ?g/ml tetracycline (Tc), 100 µg/ml ampicillin (Ap), 25 µg/ml kanamycin (Km) and 0.7 mM isopropyl-D-thio galactopyranoside (IPTG), and 40 µg/ml of 5-bromo-4-chloro-indolyl-β-D-galactopyramoside (XGal) when required. *P. aeruginosa* was grown on LB or PIA. When necessary, PIA was supplemented with 300 µg/ml carbenicillin, or 300 µg/ml Tc. All incubation were at 37° C.

Construction of algD::lacZ lysogens in *E. coli*

Using the strategy of Simons, et al. (1987) single copy chromosomal fusions in *E. coli* were generated. A 1.2 kb HindIII-EcoRI fragment carrying the algD promoter from *P. aeruginosa* PAO was excised from pPAOM3, converted at the HindIII end into the BamHI specificity, and cloned as a BamHI-EcoRI fragment into the BamHI and EcoRI digested transcriptional fusion plasmid pRS550. The resulting plasmid pBED, carrying the algD::lacZ fusion, was introduced in *E. coli* strain DR459, which was then infected with the bacteriophage λRS74. This λ phage derivative carries a 7.9 kb EcoRI insert that matches the genes flanking the lacZ fusion in pRS550, and thus permits genetic exchange between the plasmid and the λ phage. Such in vivo recombinational events can be selected based on the associated transfer of Kmr from the plasmid to the phage. *E. coli*

DR459 was infected with λ phage lysates prepared on E. coli harboring pBED. λ phage lysogens carrying the algD::lacZ fusion integrated on the chromosome were selected as Kmr colonies. Several strains were obtained and the presence of single-copy intact algD::lacZ fusion was verified by Southern blot analysis. One such strain, designated VD1870, was used in further studies.

DNA amplification, Cloning and Sequencing

Oligonucleotides UL5 (5'-GCCGCACGTCACGAGC-3') (SEQ ID NO:20) and UR20 (5'-CGCGAACCGCACCATCGCTC-3') (SEQ ID NO:21) were used for PCR amplification of the sequences beginning 120-bp upstream of the algU initiation codon and ending 193-bp past the stop codon of mucA resulting in a 1.5-kb PCR product. Where indicated, direct cycle sequencing of PCR products was performed using AmpliTaq Cycle Sequencing kit (Perkin-Elmer). Sequences illustrating algU mutations were generated with the sequencing primers UR14 (5'ATCGCTGTCCGGTCGGC3') (SEQ ID NO:22) and UR16 (5'GAGTTCATCCGCTTCG3') SEQ ID NO:23.

Transcriptional Fusion and Alginate Assays

For xylE transcriptional fusion measurements, all strains harbored the algD::xylE transcriptional fusion plasmid pPAOM3 which was introduced into P. aeruginosa by triparental filter matings. Activity of the xylE gene product, catechol 2,3 dioxygenase (CDO), was assayed as previously described. Expression of the algD::lacZ fusion was measured by following β-galactosidose activity in sonic extracts obtained from cells harboring various plasmids and grown for 48 h on LB plates supplemented with Ap, Km, Tc, and IPTG. The specific activity of β-galactosidase was determined by hydrolysis of o-nitrophenyl β-D-galactopyranoside (ONPG) at 420 nm in a spectrophotometer and expressed in mU/mg. One unit is defined as the amount of enzyme hydrolyzing 1 nmole of ONPG in 1 min. Molar extinction coefficient of the reaction product, o-nitrophenol, is 4500. Alginate measurements were performed in triplicate by the method of Knutson and Jeanes (1976).

Reconstitution of algU-dependent algD transcription in E. coli

Figure 5B:
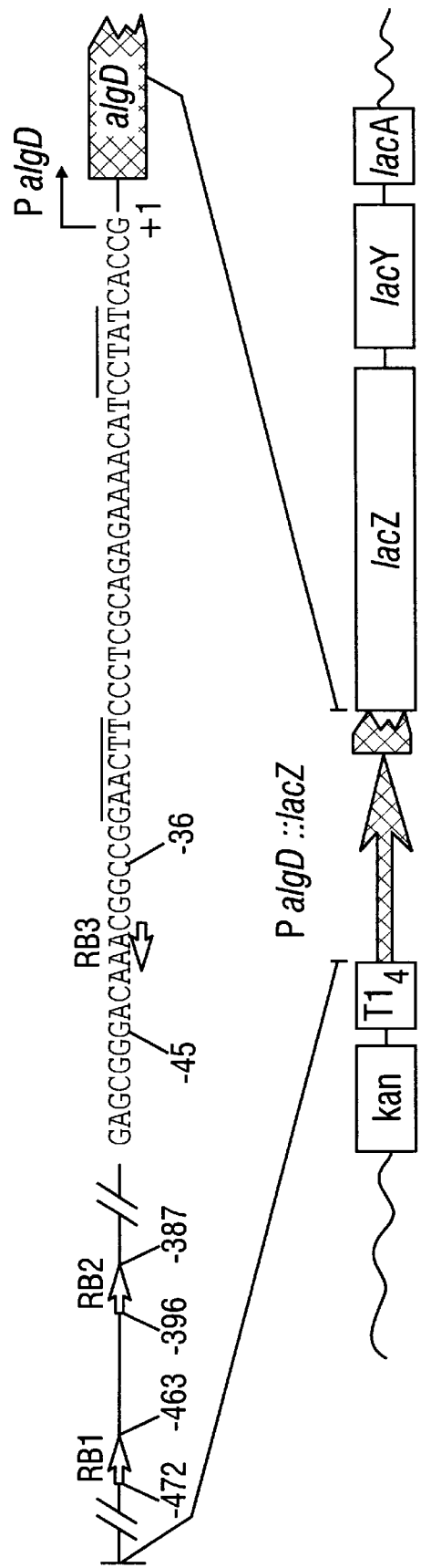
FIG. 5B. Partial nucleotide sequence and organization of the algD promoter. T
Figure 5C:
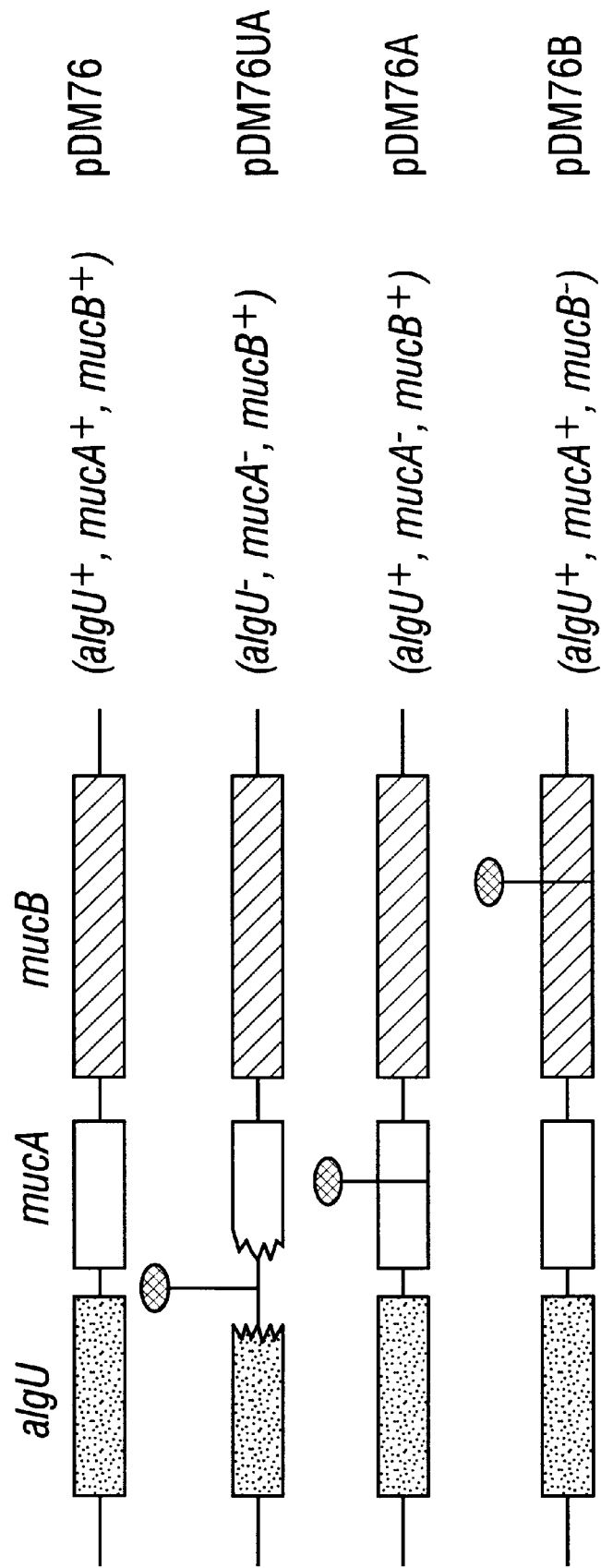
FIG. 5C. Diagram depicting the inserts of plasmids pDM76, pDM76UA, pDM76A, and pDM76B, used in this study. Balloons indicate the locations of the Tcr cassette used for insertional inactivation of genes on the plasmid pDM76. Jagged edges of the boxes corresponding to algU (stippled) and mucA (open) indicate that the 3' end of algU and the 5' end of mucA have been deleted in the construct pDM76UA.

The algD promoter is a critical site for the regulation of mucoidy. All known elements required for the full activation of this promoter are contained within the region beginning at −533 and extending to +112 relative to the algD mRNA start site. A 1.2 kb DNA fragment including this region (extending from the HindIII site, located 1.1 kb upstream, to the EcoRI site located at +112 downstream of the algD mRNA start site) was modified and cloned as a BamHI-EcoRI fragment into pRS550. This way, the algD promoter was positioned upstream of the promoterless lacZYA operon. The lacZ transcriptional fusion vector pRS550 permits in vivo transfer of the in vitro generated fusions from the plasmid to a companion λ phage via genetic recombination of the regions flanking the fusion. After exchange of algD::lacZ carrying region with the phage λRS74, the algD-::lacZ lysogen E. coli strain VD1870 was constructed (FIG. 5B). The nucleotide sequence of the region immediately upstream of the mRNA start site is shown; overlined bold letters indicate the conserved −35 and −10 motifs of promoters regulated by AlgU homologs. The three AlgR binding sites RB1, RB2, and RB3 have the highly conserved core sequence 5'ACCGTTGTC3'-3', which in the case of RB3 runs in the opposite direction of RB1 and RB2, and due to two mismatches has a lower affinity for AlgR. Numbers underneath the sequence denote positions of the core sequences relative to the algD mRNA start site (+1). A 1.2 kb fragment containing the algD promoter was used to generate the transcriptional fusion with lacZ in the E. coli lysogen VD1870 carrying chromosomally integrated algD-::lacZ (PalgD::lacZ). Other symbols: kan, kanamycin resistance; T14, four tandem copies of the strong transcriptional terminator T1 of the E. coli rrnB operon. Wavy lines indicate the E. coli chromosome.

Figure 6:
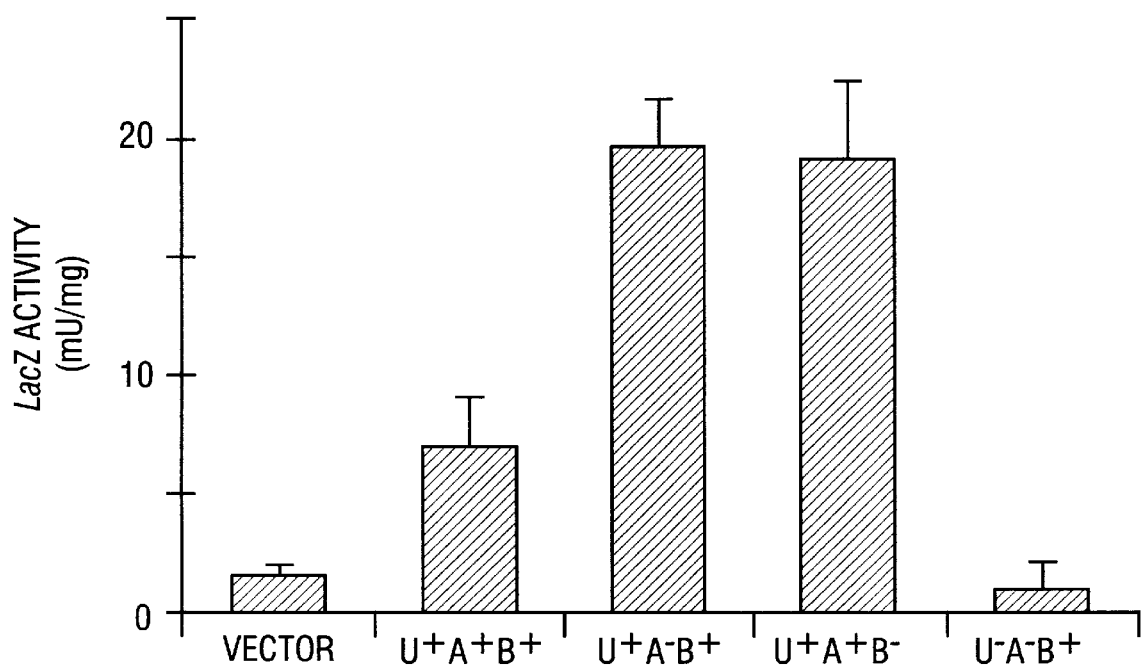
FIG. 6. Stimulation of algD::lacZ expression by algU. LacZ (β-galactosidase) activity (expressed in mU per mg of total cell protein) was determined in sonic extracts of the algD::lacZ lysogen strain VD1870 harboring one of the following plasmids: pUC12 (vector); pDM76 carrying the wild type algU mucA mucB cluster from PAO1 (U+A+B+); pDM76A carrying the same cluster except that the mucA gene was insertionally inactivated (U+A–B+); pDM76B (U+A+B–) carrying the cluster with insertionally inactivated mucB; pDM76UA, with a deletion of the 3' end of algU and the 5' end of mucA (U–A–B+). T bars, standard error.

To assess whether algU directly activates algD transcription, the present inventors attempted to clone the algU gene alone on a plasmid and to introduce such a construct into VD1870. This presented difficulties, since transformants containing plasmid constructs with inserts carrying algU devoid of mucA and mucB quickly lost their viability. However, when algU was cloned together with mucA and mucB in pUC12, this permitted its stable maintenance in E. coli. When the resulting plasmid pDM76 was introduced into the algD::lacZ transcriptional fusion strain VD1870, the transformant colonies displayed a light blue color on plates supplemented with XGal. β-galactosidase activity was detectable in sonic extracts prepared from VD1870 harboring pDM76 (FIG. 6). These results indicated that algD transcription can be initiated, albeit at a low level, by algU in the presence of its presumptive negative regulators mucA and mucB. A very low β-galactosidase activity was also detectable in sonic extracts of VD1870 carrying the pUC12 vector only, indicating that a background algD transcription was present in E.coli.

Inactivation of mucA or mucB results in stimulation of algD transcription

The inventors determined whether this phenomenon could be reconstructed in E. coli. When VD1870 was transformed with the variants of the plasmid pDM76 carrying insertionally inactivated mucA (pDM76A) or mucB (pDM76B), this further increased the transcription of algD-::lacZ on the chromosome as evidenced by a darker blue coloration of colonies on plates supplemented with XGal and accompanied increase of β-galactosidase activity in sonic extracts (FIG. 6). This activation was dependent on the presence of a functional algU gene, since the plasmid pDM76UA with a double mutation, which simultaneously inactivated algU and mucA, did not stimulate algD transcription over the background level (FIG. 5). Furthermore, it was possible to complement mucA and mucB mutations on pDM76A and pDM76B, respectively, by introducing a compatible second plasmid carrying mucA and mucB cloned behind the tac promoter. Introduction of such a construct, pMJStac84AB, which also carries the lacI$^q$ gene, into the strain VD1870 harboring plasmids with insertionally inactivated mucA or mucB (pDM76A or pDM76B) but carrying an active algU, did not significantly affect algD::lacZ expression. When transcription of mucA and mucB on pMJStac84AB was further induced by IPTG, algD::lacZ expression was completely abrogated (FIG. 7), bringing the levels of β-galactosidase activity significantly below the values observed in the control strains (e.g. VD1870 harboring pUC12, FIG. 6). These experiments suggest that: (i) mucA and mucB play a direct negative regulatory role in algD transcription; and (ii) they exert this effect via algU, since loss of algU was epistatic to the inactivation of mucA.

Effects of AlgR on algD Transcription in E. coli

Many different regulatory elements have been proposed to cooperate in the process of algD activation. One of the better studied factors is the response regulator AlgR, which has been shown to bind to three sites within the algD promoter (FIG. 5B) defined by the recognition sequence ACCGT-TGTC. In order to examine whether algR could affect the function of the reconstituted system of algD transcription in

Figure 8:
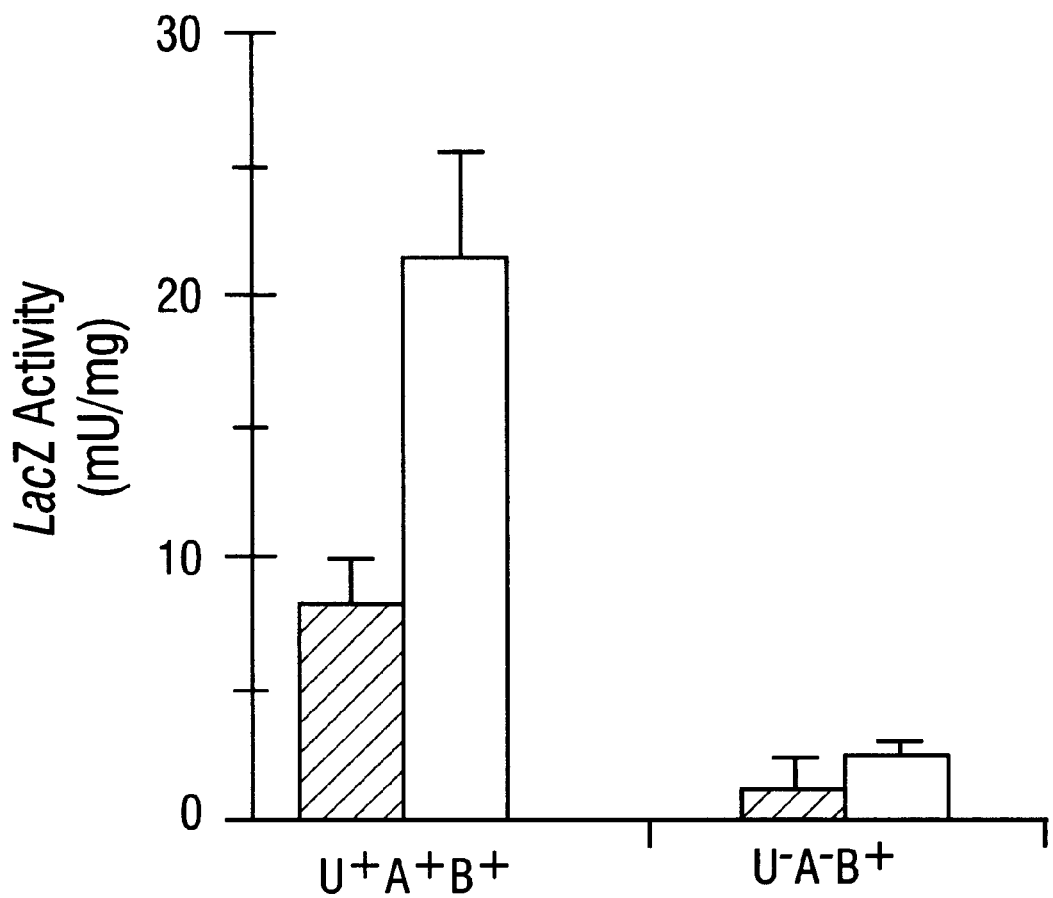
FIG. 8. AlgR stimulates algD expression in E. coli. VD1870 (algD::lacZ lysogen E. coli) harbored plasmids pDM76 (U+A+B+) or pDM76UA (U–A–B+). Stippled bars, no algR; open bars, algR present on the second plasmid pMJStac84R.

*E. coli*, the algR gene was subcloned on a vector compatible with pUC12. This construct, pMJStac84R, was introduced into the algD::lacZ lysogen VD1870 and the resulting strain secondarily transformed with pDM76. The presence of algR additionally stimulated algD transcription over the levels obtained with pDM76 alone (FIG. 8). However, the algR-dependent transcription of algD was significantly lower vis-a-vis algU-dependent stimulation of algD expression (FIG. 8). Moreover, when the medium was supplemented with 1 mM IPTG to increase algR expression, this resulted in a decreased algD transcription. The reasons for this are currently not known, but the status of AlgR-phosphorylation and a number of other phenomena could account for this observation.

EXAMPLE 7

Instability of mucoidy in *P. aeruginosa* and second site suppressor mutations in algU The role of mutations at the algU loci were also conducted. Further support for the mechanism of reversion to nonmucoidy in *P. aeruginosa*, a phenomenon frequently referred to as the instability of mucoid phenotype, was found. Spontaneous nonmucoid derivatives of the mucoid strain PAO578 carrying the mucA22 mutation were examined for the presence of alterations within the algU mucA mucB locus. Point mutations which inactivated algU were detected in some, but not all, nonmucoid revertants. No reversion of the original mucA22 mutation (a deletion of one C) was observed in any of the investigated strains. This suggests that the process of conversion to nonmucoidy can be explained, at least partially, by second site suppressor mutations, and that a fraction of such mutations occurs in algU.

The mucoid phenotype of *P. aeruginosa* is frequently unstable and nonmucoid variants can be observed upon repeated passages on standard laboratory media (Govan, (1988), and Ohman, et al., (1990). The fact that conversion to mucoid phenotype in some strains is a result of mucA inactivation (Martin, et al. (1993)) suggests that in such mutants the presence of uncontrolled AlgU could interfere with the normal physiology of the cell. It is thus not surprising that in the absence of selective pressure to maintain mucoid phenotype, e.g. once the strains are extracted form the CF lung, nonmucoid variants emerge. Based on the studies with the epistatic nature of algU relative to mucA mutations presented here, and the fact that algU mutants are viable in the laboratory, it was hypothesized that conversion to nonmucoid phenotype could be due to mutations in algU.

In order to demonstrate this possibility, the strain PAO578 was chosen for further study. PAO578 has the following relevant characteristics: (i) It consistently displays a relatively high level instability of the mucoid phenotype and nonmucoid variants can be readily obtained; and (ii) it carries the fully characterized mucA22 mutation (a deletion of a single nucleotide within a string of 5 Cs in the coding region of mucA), which has been shown in the previous Examples, by gene replacements to cause conversion to mucoidy. In the process of isolating spontaneous nonmucoid variants, it was observed that PAO578 gave rise to at least 3 morphologically distinct types differing from the mucoid appearance of the parent PAO578. The different morphotypes of PAO578 and its derivatives were classified based on their phenotype on two media, PIA and LB: Type I was mucoid on PIA and LB [the original PAO578]; type II was mucoid on PIA, but lost its mucoid appearance on LB; type III was nonmucoid on both PIA and LB; and type IV displayed a very low level but detectable mucoidy on both media after prolonged incubation. This suggested that there were several ways the system could adjust to the presence of a mucA mutation. Type III was further examined to investigate mechanisms contributing to complete conversion to nonmucoidy, and to test whether the original mutation in mucA had been repaired in such strains.

Three randomly chosen, independently obtained type III isolates were subjected to further analysis. First, the levels of alginate production and algD transcription were determined, in order to rule out mutations that did not affect algD expression (e.g., altered export of the exopolysaccharide, etc.). The strains, PAO57874, PAO578160, displayed dramatic reduction in detectable uronic acids, and algD transcription relative to PAO578 (Table 9).

TABLE 9

Alginate production and algD transcription in PAO578 and its spontaneous nonmucoid derivatives PAO57874 and PAO578160

| Strain[a] | Pheno-type[b] | algU mucA alleles | Alginate production (μg/mg of wet cell weight) | CDO[c] (U/mg) |
|---|---|---|---|---|
| PAO578 | M | algU + mucA22 | 100.33 ± 19.2 | 60.51 ± 21.1 |
| PAO57874 | NM | algU74 mucA22 | 0.57 ± 0.065 | 0.014 ± 0.001 |
| PAO578160 | NM | algU160 mucA22 | 0.60 ± 0.23 | 0.017 ± 0.003 |

[a]PAO578160 and PAO57874 are spontaneous, type III (see text) nonmucoid derivatives of PAO578.
[b]Phenotype was scored as mucoid (M) or nonmucoid (NM) on PIA.
[c]For transcriptional fusion measurements, all strains harbored pPAOM3 carrying an algD::xylE transcriptional fusion. Activity was expressed as units of catechol 2,3 deoxygenase (CDO; the xylE gene product) per mg of crude protein extracts ± SE.

Figure 9B:
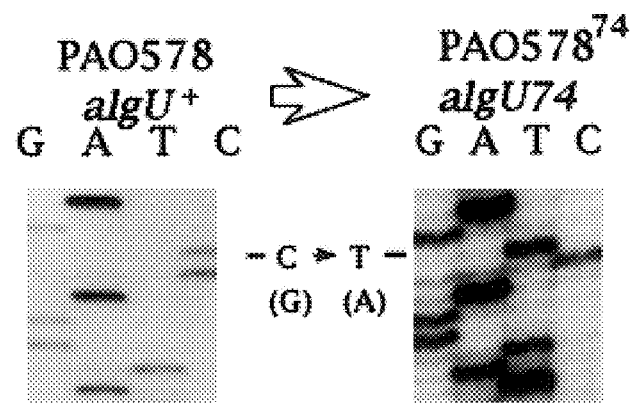
FIG. 9B Illustration of the sequence alterations within algU in spontaneous nonmucoid derivatives (type III) of the mucoid strain PAO578 (mucA22). Gel sections show the corresponding regions of algU from strains PAO578 (algU+ mucA22, mucoid), PAO57874 (algU74 mucA22, nonmucoid) and PAO578160 (algU160mucA22, nonmucoid). Bars show positions of deleted or substituted nucleotides. The sequences in B are that of the anti-sense strand; nucleotides in parenthesis indicate corresponding residues in the sense strand.
Figure 9C:
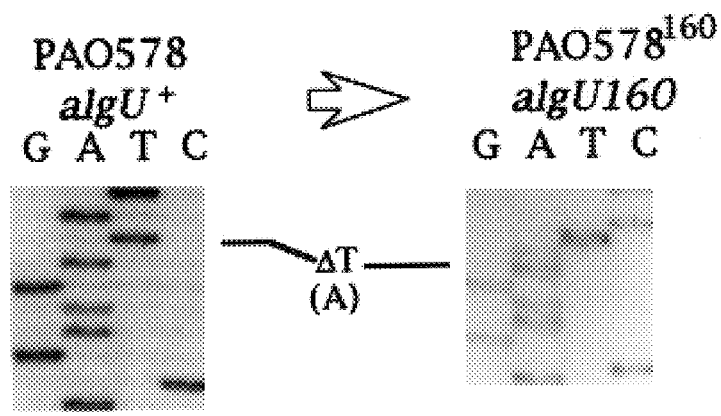
FIG. 9C Illustration of the sequence alterations within algU in spontaneous nonmucoid derivatives (type III) of the mucoid strain PAO578 (mucA22). Gel sections show the corresponding regions of algU from strains PAO578 (algU+ mucA22, mucoid), PAO57874 (algU74 mucA22, nonmucoid) and PAO578160 (algU160mucA22, nonmucoid).

This was also the case with the third isolate studied, PAO57800. Next, the chromosomal regions encoding algU and mucA were amplified by PCR from these strains, and subjected to direct nucleotide sequencing of the PCR products. When the sequences of mucA were examined, all strains displayed the presence of the original mucA22 mutation. In contrast, when algU was sequenced, the results of these analyses showed that the strains PAO57874 and PAO578160 had acquired new mutations in algU that were not present in the parental mucoid strain PAO578 (FIG. 9A-1 and FIG. 9A-2). The lesion in PAO57874 was a nonsense mutation, which resulted in conversion of the codon specifying Trp74 into a stop codon. The strain PAO578160 had a frameshift mutation (deletion of a T residue within the codon specifying Asp160) which brought in frame a premature stop codon 10 nucleotides downstream of the deletion. However, the third strain tested, PAO57800, did not have any alterations within the algU coding region. This strain still carried the original mucA22 mutation, thus ruling out the possibility that its change into the nonmucoid phenotype was due to the repair of the lesion in mucA.

To ascertain whether the detected algU lesions were responsible for conversion to nonmucoidy in PAO57874 and PAO578160, gene replacements of the respective algU alleles with the wild type algU gene from PAO1 were carried out. The plasmid pDMUM13 carrying the wild type algU mucA genes were introduced into PAO57874 and PAO578160 by triparental filter matings, and Tcr exconjugants selected. The resulting strains were nonmucoid, but gave rise to rare mucoid colonies detectable on a lawn of nonmucoid cells harboring the plasmid. Such mucoid derivatives were candidates for gene replacements of the mutant chromosomal algU gene (alleles algU74 and algU176) with the wild type copy of algU (algU+). This was verified by plasmid curing, purification of mucoid derivatives which were TcS and thus had lost the plasmid, followed by amplification of the algU sequences and their direct sequencing. The results of these experiments confirmed that the chromosomal alleles algU74 and algU160 had been replaced by the functional wild type copies of algU in all mucoid colonies that were tested. This served as a demonstration that the algU mutations in PAO57874 and PAO578160 were responsible for conversion to nonmucoidy. These findings suggest, that although multiple mechanisms exists, one pathway of reverting to nonmucoid phenotype in *P. aeruginosa* is through inactivation of algU.

The present inventors have also achieved the algU-dependent algD transcription in a heterologous host. This work provides further characterization of the gene cluster controlling conversion to mucoidy in *P. aeruginosa* and provides the means for identifying compounds that may inhibit alginate production. The genetic reconstitution experiments, presented herewith, have been carried out in a heterologous host which does not produce alginate, and therefore is expected to lack the necessary elements for expression of alg genes. This strongly suggests that AlgU acts directly on algD.

Efforts to overproduce and purify AlgU have indicated that expression clones of the algU gene are highly unstable. The reasons for this are currently not known, but one possible explanation is that the gene product is toxic to bacterial cells. The present inventors have noticed that *E. coli* strains transformed with high copy number plasmids carrying algU can form colonies on selection media but are difficult or impossible to propagate. It is worth mentioning that the initial analysis of the algU mucA mucB locus via deletion subcloning approach has resulted in a series of deletions from both the 5' and 3' ends of the algU mucA mucB cluster. The deletion clones generated from the 5' end represent an unbiased series of overlapping clones with more or less evenly distributed deletion end points. Interestingly, in contrast to this the 3' end deletions never extended into the mucA gene while leaving algU intact on the same fragment. Thus, the only recovered deletion clones from the 3' end of the cluster either contained the complete algU and mucA genes, or had deletion end points encroaching on the coding region of algU. This further supports the notion that the algU gene product may be toxic to the cells, and also suggests that this putative toxicity is counteracted by the presence of mucA (and possibly mucB).

One explanation for this effect of mucA is that it suppresses the activity of AlgU. Such negative regulation of algU by mucA has been addressed and established in the studies presented here. For example, insertional inactivation of mucA derepresses algU-dependent algD transcription in the genetically reconstructed system in *E. coli*. This is in keeping with the observations that mucoid strains of *P. aeruginosa* can emerge both in vitro (Fyfe, et al. (1980) and in vivo (Martin, et al. (1993A)) via spontaneous frameshift or nonsense mutations in mucA on the chromosome. One could then expect that mutations which inactivate mucA could generate strong selective pressure to contain or suppress the unattended and presumably toxic AlgU. Thus, it is not surprising that many mucoid CF isolates, and laboratory strains which have been converted to mucoidy via genetic manipulations of mucA or mucB (Martin, et al. (1993B), in absence of selective pressures to maintain mucoid phenotype, show tendency to convert into nonmucoid or attenuated alginate producing forms. One mechanism underlying these processes has been presented herewith, and is based on occurrence of second site suppressor mutations in algU which can override the effects of mucA mutations. However, this is not the only mechanism of conversion to nonmucoid phenotype. The analysis of PAO578 variants displaying various medium-dependent patterns and attenuated levels of alginate production, and the absence of algU mutation in the nonmucoid derivative type III PAO57800, strongly suggest that pseudoreversion to a nonmucoid state can occur via several alternative pathways. These mechanisms of attenuating constitutive alginate production are currently investigated since they may help uncover additional factors that interact with AlgU.

PROPHETIC EXAMPLE 8

Screening for Candidate Mucoid Inhibitors

The present invention also provides candidate substance screening methods which are based upon whole cell assays and which, preferably, employ the LacZ reporter gene that confers on its recombinant hosts a readily detectable phenotype that emerges only under conditions where the protein products of algU, mucA and mucB, control transcription of the algD gene. Generally, reporter genes encode a polypeptide not otherwise produced by the host cell which is detectable by analysis of the cell culture, e.g., by fluorometric, radioisotopic or spectrophotometric analysis of the bacterial culture. Exemplary enzymes include esterases, phosphatases, proteases (tissue plasminogen activator or urokinase) and other enzymes capable of being detected by their activity, as will be known to those skilled in the art. A preferred example is *E. coli* beta-galactosidase, which produces a color change upon cleavage of an indigogenic substrate.

The polypeptide products of the reporter gene are secreted, intracellular or, as noted above, membrane bound polypeptides. If the polypeptide is not ordinarily secreted it is fused to a heterologous signal sequence for processing and secretion. In other circumstance the signal is modified in order to remove sequences that interdict secretion. Preferably, however, the products of the reporter gene are lodged in the intracellular or membrane compartments, and may be released as described in Example 7 through sonication. Then they can be fixed to the culture container, e.g., microtiter wells, in which they are grown, followed by addition of a detectable signal generating substance such as a chromogenic substrate for reporter enzymes.

In general, the proteins of the present invention are employed to control transcription and expression of the reporter gene. The process which in its entirety leads to enhanced transcriptional promotion is termed "activation." The mechanism by which a successful candidate substance acts is not material since the objective is to promote the expression of wild-type algU, mucA and mucB in order to inhibit algD expression or function, and particularly the activity of the algD gene product in alginate sysnthesis, by whatever means will function to do so. The use of the entire gene loci is preferred as it will most closely model the therapeutic target, and given the surprising difficulties in expressing algU alone.

The host cells used in the screening assay herein generally are *E. Coli* cells, and are preferably cell lines which may be used in connection with Example 6. These bacteria should be relatively easy to grow in large scale culture, and may be tested in microtiter plates. Also, as provided for in Example 8, the native background can be easily accounted for, and may serve to examine both agonists and antagonists of algD gene expression.

The screening assay typically is conducted by growing the transformants to confluency in microtiter wells, adding serial molar proportions of candidate substances to a series of wells, and the signal level determined after an incubation period that is sufficient to demonstrate β-galactosidase activity in controls incubated alone. The throughput of samples can be greatly enhanced through the use of automated ELISA readers, scanning at an optical density of 410 nm. The wells containing varying proportions of candidate are then evaluated for signal activation. Candidates that demonstrate dose related enhancement or repression of reporter gene transcription or expression are then selected for further evaluation as clinical therapeutic agents. The stimulation of transcription may be observed in the absence of added candidate, in which case the candidate compound might be a positive stimulator of algD gene transcription. Alternatively, the candidate compound might only give a stimulation in the presence of algU, mucA and mucB, which would indicate that it functions to oppose the algU-mediated suppression of the algD promoter. Candidate compounds of either class might be useful therapeutic agents that would stimulate production of algU and thereby preclude *P. aeruginosa* mucoidy in CF patients.

It should be understood that the screening method herein is useful notwithstanding that effective candidates may not be found, since it would be a practical utility to know that algU activators do not exist. The invention consists of providing a method for screening for such candidates, not in finding them.

The term "capable of activating algU-mucA-mucB mediated inhibition of algD" means that upon contacting the bacteria, with the algU-mucA-mucB repressed algD reporter system, for example, under appropriate conditions of ionic strength, temperature, pH and the like, specific binding will occur, and thereby repression of algD promoter driven transcription. The interaction may occur due to specific electrostatic, hydrophobic, entropic or other interaction of certain amino acid residues of the one protein, with specific amino acid residues of the second protein, particularly algU binding to mucA and mubB, to form a stable complex under the conditions effective to promote the interaction. The interaction may alter the three dimensional conformation of either or both proteins or polypeptides involved in the interaction and it may also alter the function or activity of either or both proteins or polypeptides involved in the interaction. For example, the interaction of algU with other protein may alter the ability of the RNA polymerase complex to bind other proteins, such as sigma factors, and to bind or recognize specific regions of DNA, to act as a substrate for a phosphorylation or dephosphorylation or other enzymatic reaction, or to catalyze or effect any enzymatic reaction involving other substrates and reactants.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

Allen, L. N., and R. S. Hanson. 1985. Construction of broad host range cloning vectors: identification of genes necessary for growth of Methylobacterium organophilum on methanol. J. Bacteriol. 161:955–962.

Anwar, H., J. L. Strap, and J. W. Costerton. 1992. Establishment of aging biofilms: possible mechanism of bacterial resistance to antimicrobial therapy. Antimicrob. Agents Chemother. 36:1347–1351.

Ausubel, F. M., R. Brent, R. E. Kingston, D. D. Moore, J. G. Seidman, J. A. Smith, and K. Struhl. 1989. Current protocols in molecular biology. John Wiley & Sons, Inc., New York.

Ausubel, F. M., Brent, R., Kingston, R. E., Moore, D. D., Seidman, J. G., Smith, J. A., and Struhl, K. (1989) Current protocols in molecular biology. John Wiley & Sons, Inc., New York.

Barry, C. E. III, S. F. Hayes, and T. Hackstadt. 1992. Nucleoid condensation in *Escherichia coli* that express a chlamydial histone homolog. Science 256:377–379.

Berry, A., DeVault, J. D., and Chakrabarty, A. M. (1989) High osmolarity is a signal for enhanced algD transcription in mucoid and nonmucoid *Pseudomonas aeruginosa* strains. J. Bacteriol. 171:2312–2317.

Burbulys, D., Trach, K. A., and Hoch, J. A. (1991) Initiation of sporulation in B. subtilis is controlled by a multicomponent phosphorelay. Cell 64:545–552.

Carter, H. L., III, and C. P. Moran, Jr. 1986. New RNA polymerase_factor under spoO control in *Bacillus subtilis*. Proc. Natl. Acad. Sci. USA 83:7438–9442.

Chater, K., C. J. Bruton, K. A. Plaskitt, M. J. Buttner, C. Mendex, and J. D. Helmann. 1989. The developmental fate of S. coelicolor hyphae depends upon a gene product homologous with the mobility_factor of *B. subtilis*. Cell 59:133–143.

Chitnis et al., 1990, "Cloning of *Pseudomonas aeruginosa* algG, which controls alginate structure", J. Bacteriol. 172(6):2894–2900.

Costerton, J. W., Lam, J., Lam, K., and Chan, R. (1983) The role of the microcolony mode of growth in the pathogenesis of Pseudomonas aeruginosa infections. Rev. Infect. Dis. 5:S867–S873.

Costerton, J. W., K.-J. Cheng, G. G. Geesey, T. I. Ladd, J. C. Nickel, M. Dasgupta, T. J. Marrie. 1987. Bacterial biofilms in nature and disease. Ann. Rev. Microbiol. 41:435–464.

Costerton, J. W., Cheng, K.-J., Geesey, G. G., Ladd, T. I., Nickel, J. C., Dasgupta, M., Marrie, T. J. (1987) Bacterial biofilms in nature and disease. Ann. Rev. Microbiol. 41:435–464.

Costerton, J. W., J. Lam, K. Lam, and R. Chan. 1983. The role of the microcolony mode of growth in the pathogenesis of *Pseudomonas aeruginosa* infections. Rev. Infect. Dis. 5:S867–S873.

Darzins, A., Wang, S. K., Vanags, R. I., and Chakrabarty, A. M. (1985) Clustering of mutations affecting alginic acid biosynthesis in mucoid *Pseudomonas aeruginosa*. J. Bacteriol. 164:516–524.

Deretic, V., and W. M. Konyecsni. 1989. Control of mucoidy in *Pseudomonas aeruginosa*: transcriptional regulation of algR and identification of the second regulatory gene, algQ. J. Bacteriol. 171:3680–3688.

Deretic, V., W. M. Konyecsni, C. D. Mohr, D. W. Martin, and N. S. Hibler. 1989. Common denominators of promoter control in Pseudomonas and other bacteria. Bio/Technology 7:1249–1254.

Deretic, V., J. R. W. Govan, W. M. Konyecsni, and D. W. Martin. 1990. Mucoid *Pseudomonas aeruginosa* in cystic fibrosis: mutations in the muc loci affect transcription of the algR and algD genes in response to environmental stimuli. Mol. Microbiol. 4:189–196.

Deretic, V., S. Chandrasekharappa, J. F. Gill, D. K. Chatterjee, and A. M. Chakrabarty. 1987. A set of cassettes and improved vectors for genetic and biochemical characterization of Pseudomonas genes. Gene 57:61–72.

Deretic, V., J. H. J. Leveau, C. D. Mohr, and N. S. Hibler. 1992. In vitro phosphorylation of AlgR, a regulator of mucoidy in *Pseudomonas aeruginosa*, by a histidine protein kinase and effects of small phospho-donor molecules. Mol. Microbiol. 6:2761–2767.

Deretic, V., J. F. Gill, and A. M. Chakrabarty. 1987. Gene algD coding for GDPmannose dehydrogenase is transcriptionally activated in mucoid *Pseudomonas aeruginosa*. J. Bacteriol. 169:351–358.

Deretic, V., and W. M. Konyecsni. 1990. A prokaryotic regulatory factor with a histone Hi-like carboxy-terminal domain: clonal variation of repeats within algP, a gene involved in regulation of mucoidy in *Pseudomonas aeruginosa*. J. Bacteriol. 172:5544–5554.

Deretic, V., N. S. Hibler, and S. C. Holt. 1992. Immunocytochemical analysis of AlgP ($H_p1$), a histonelike element participating in control of mucoidy in *Pseudomonas aeruginosa*. J. Bacteriol. 174:824–831.

Deretic, V., C. D. Mohr, and D. W. Martin. 1991. Mucoid *Pseudomonas aeruginosa* in cystic fibrosis: signal transduction and histone-like elements in the regulation of bacterial virulence. Mol. Microbiol. 5:1557–1583.

Deretic, V., R. Dikshit, W. M. Konyecsni, A. M. Chakrabarty, and T. K. Misra. 1989. The algR gene, which regulates mucoidy in *Pseudomonas aeruginosa*, belongs to a class of environmentally responsive genes. J. Bacteriol. 171:1278–1283.

Deretic, V., Hibler, N. S. and Holt, S. C. (1992) Immunocytochemical analysis of AlgP ($H_p1$), a histonelike element participating in control of mucoidy in *Pseudomonas aeruginosa*. J. Bacteriol. 174:824–831.

Deretic, V., Govan, J. R. W., Konyecsni, W. M., and Martin, D. W. (1990) Mucoid *Pseudomonas aeruginosa* in cystic fibrosis: mutations in the muc loci affect transcription of the algR and algD genes in response to environmental stimuli. Mol. Microbiol. 4:189–196.

Deretic, V., Mohr, C. D., and Martin, D. W. (1991) Mucoid *Pseudomonas aeruginosa* in cystic fibrosis: signal transduction and histone-like elements in the regulation of bacterial virulence. Mol. Microbiol. 5:1557–1583.

Deretic, V., Konyecsni, W. M., Mohr, C. D., Martin, D. W., and Hibler, N. S. (1989) Common denominators of promoter control in Pseudomonas and other bacteria. Bio/Technology 7:1249–1254.

Deretic, V., Gill, J. F., and Chakrabarty, A. M. (1987) Gene algD coding for GDPmannose dehydrogenase is transcriptionally activated in mucoid *Pseudomonas aeruginosa*. J. Bacteriol. 169:351–358.

Deretic, V., Dikshit, R., Konyecsni, W. M., Chakrabarty, A. M., and Misra, T. K. (1989) The algR gene, which regulates mucoidy in *Pseudomonas aeruginosa*, belongs to a class of environmentally responsive genes. J. Bacteriol. 171:1278–1283.

DeVault, J. D., Kimbara, K., and Chakrabarty, A. M. (1990) Pulmonary dehydration and infection in cystic fibrosis: evidence that ethanol activates alginate gene expression and induction of mucoidy in *Pseudomonas aeruginosa*. Mol. Microbiol. 4:737–745.

Dubnau, D. (1991) The regulation of genetic competence in *Bacillus subtilis*. Mol. Microbiol. 5:11–18.

Dubnau, D. 1991. The regulation of genetic competence in *Bacillus subtilis*. Mol. Microbiol. 5:11–18.

Dubnau, E., J. Weir, G. Nair, L. Carter III, C. Moran, Jr., and I. Smith. Bacillus sporulation gene spo0H codes for $\_^{30}$ ($\_^{4}$). Bacteriol. 170:1054–1062 . . . F-4.

Dubnau, E., Weir, J., Nair, G., Carter III, L., Moran, Jr., C., and Smith, I. (1988) Bacillus sporulation gene spo0H codes for $^{30}$ ($^{4}$). J. Bacteriol. 170:1054–1062.

Figurski, D. H., and D. R. Helinski. 1979. Replication of an origin-containing derivative of plasmid RK2 dependent on a plasmid function provided in trans. Proc. Natl. Acad. Sci. USA 76:1648–1652.

Flynn, J. L., and D. E. Ohman. 1988. Cloning of genes from mucoid *Pseudomonas aeruginosa* which control spontaneous conversion to the alginate production phentotype. J. Bacteriol. 170:1452–1460.

Flynn, J. L., and Ohman, D. E. (1988) Cloning of genes from mucoid *Pseudomonas aeruginosa* which control spontaneous conversion to the alginate production phentotype. J. Bacteriol. 170:1452–1460.

Flynn, J. L., and Ohman, D. E. (1988b) Use of gene replacement cosmid vector for cloning alginate conversion genes from mucoid and nonmucoid *Pseudomonas aeruginosa* strains: algS controls expression of algT. J. Bacteriol. 170:3228–3236.

Fyfe, J. A. M., and J. R. W. Govan. 1983. Synthesis, regulation and biological function of bacterial alginate. In Progress in inductrial microbiology, vol. 18 (Bushell, M. E., ed.). Elsevier, Amsterdam, pp. 45–83.

Fyfe, J. A. M. 1985. Studies on some unusual characteristics expressed by *Pseudomonas aeruginosa* associated with chronic respiratory infections. Ph.D. Thesis. University of Edinburgh.

Fyfe, J. A. M., and Govan, J. R. W. (1983) Synthesis, regulation and biological function of bacterial alginate. In Progress in inductrial microbiology, vol. 18 (Bushell, M. E., ed.). Elsevier, Amsterdam, pp. 45–83.

Fyfe, J. A. M., and J. R. W. Govan. 1980. Alginate synthesis in mucoid *Pseudomonas aeruginosa*: a chromosomal locus involved in control. J. Gen. Microbiol. 119:443–450.

Fyfe, J. A. M., and Govan, J. R. W. (1980) Alginate synthesis in mucoid *Pseudomonas aeruginosa*: a chromosomal locus involved in control. J. Gen. Microbiol. 119:443–450.

Goldberg et al., 1992, "*Pseudomonas aeruginosa* algB which modulates the expression of alginate, is a member of the NTrC subclass of prokaryotic regulators", *Mol. Microbiol.* 6(1):59–66.

Goldberg, J. B., J. Won, and D. E. Ohman. 1990. Precise excision and instability of the transposon Tn5 in *Pseudomonas aeruginosa*. J. Gen. Microbiol. 136:789–796.

Govan, J. R. W., and G. S. Harris. 1986. *Pseudomonas aeruginosa* and cystic fibrosis: unusual bacterial adaptation and pathogenesis. Microbiol. Sci. 3:302–308.

Govan et al. 1992, "Mucoid *Pseudomonas aeruginosa* and cystic fibrosis: The role of mutations in muc loci" *FEMS MICROBIOL. LETT.* 100(1–3):323–329.

Govan, J. R. W. (1988) Alginate biosynthesis and other unusual characteristics associated with the pathogenesis of *Pseudomonas aeruginosa* in cystic fibrosis. p. 67–96.

In E. Griffiths, W. Donachie, and J. Stephen, (eds.), Bacterial infections of respiratory and gastrointestinal mucosae. IRL Press, Oxford.

Govan, J. R. W. 1988. Alginate biosynthesis and other unusual characteristics associated with the pathogenesis of *Pseudomonas aeruginosa* in cystic fibrosis. p. 67–96. In E. Griffiths, W. Donachie, and J. Stephen, (eds.), Bacterial infections of respiratory and gastrointestinal mucosae. IRL Press, Oxford.

Helmann, J. D., and M. J. Chamberlin. 1988. Structure and function of bacterial sigma factors. Ann. Rev. Biochem. 57:839–872.

Hindahl, M. S., D. W. Frank, A. Hamood, and B. H. Iglewski. 1988. Characterization of a gene that regulates toxin A synthesis in *Pseudomonas aeruginosa*. Nucleic Acids Res. 16:5699.

Holloway, B. W. 1955. Genetic recombination in *Pseudomonas aeruginosa*. J. Gen. Microbiol. 13:572–581.

Ishimoto, K., and S. Lory. 1989. Formation of pilin in *Pseudomonas aeruginosa* requires the alternative factor (RpoN) of RNA polymerase. Proc. Natl. Acad. Sci. USA 86:1954–1957.

Kalman, S., Duncan, M. L., Thomas, S. M., and Price, C. W. (1990) Similar organization of the sigB and spoIIA operons encoding alternate sigma factors of *Bacillus subtilis* RNA polymerase. J. Bacteriol. 172:5575–5585.

Kato, J., and A. M. Chakrabarty. 1991. Purification of the regulatory protein AlgR1 and its binding in the far upstream region of the algD promoter in *Pseudomonas aeruginosa*. Proc. Natl. Acad. Sci. USA 88:1760–1764.

Kato, J., T. K. Misra, and A. M. Chakrabarty. 1990. AlgR3, a protein resembling eukaryotic histone H1, regulates alginate synthesis in *Pseudomonas aeruginosa*. Proc. Natl. Acad. Sci. USA 87:2887–2891.

Kimbara, K., and A. M. Chakrabarty. 1989. Control of alginate synthesis in *Pseudomonas aeruginosa*: regulation of the algR1 gene. Biochem. Biophys. Res. Com. 164:601–608.

Knutson, C. A., and A. Jeanes. 1976. A new modification of the carbazole reaction: application to heteropolysaccharides., Anal. Biochem. 24:470–481.

Knutson, C. A., and Jeanes, A. (1976) A new modification of the carbazole reaction: application to heteropolysaccharides. Anal. Biochem. 24:470–481.

Konyecsni et al., 1990, "DNA Sequence and Expression analysis of algP and algQ, components of the multigene system transcriptionally regulating mucoidy in *Pseudomonas aeruginosa*: algP contains multiple direct repeats", *J. Bacteriol.* 172(5):2511–2520.

Konyecsni, W. M., and V. Deretic. 1990. DNA sequence and expression analysis of algP and algQ, components of the multigene system transcriptionally regulating mucoidy in *Pseudomonas aeruginosa*: algP contains multiple direct repeats. J. Bacteriol. 172:2511–2520.

Konyecsni, W. M., and V. Deretic. 1989. Broad-host-range plasmid and M13 bacteriophage-derived vectors for promoter analysis in *Escherichia coli* and *Pseudomonas aeruginosa*. Gene 74:375–386.

Konyecsni, W. M., and Deretic, V. (1989) Broad-host-range plasmid and M13 bacteriophage-derived vectors for promoter analysis in *Escherichia coli* and *Pseudomonas aeruginosa*. Gene 74:375–386.

Krieg, D., R. Helmke, V. German, and J. Mangos. 1988. Resistance of mucoid *Pseudomonas aeruginosa* to opsonic phagocytosis by alveolar macrophages in vitro. Infect. Immun. 56:3173–3179.

Krishnapillai. V. 1971. A novel transducing phage. Its role in recognition of a possible new host-controlled modification system in *Pseudomonas aeruginosa*. Mol. Gen. Genet. 114:134–143.

Lonetto, M., M. Gribskov, and C. A. Gross. 1992. The $\_^{70}$ family: sequence conservation and evolutionary relationships. J. Bacteriol. 174:3843–3849.

Losick, R., P. Youngman, and P. J. Piggot. 1986. Genetics of endospore formation in *Bacillus subtilis*. Ann. Rev. Genet. 20:625–669.

Losick, R., Youngman, P., and Piggot, P. J. (1986) Genetics of endospore formation in *Bacillus subtilis*. Ann. Rev. Genet. 20:625–669.

MacGeorge, J., V. Korolik, A. F. Morgan, V. Asche, and B. W. Holloway. 1986. Transfer of a chromosomal locus responsible for mucoid colony morphology in *Pseudomonas aeruginosa* isolated from cystic fibrosis patients to *P. aeruginosa* PAO. J. Med. Microbiol. 21:331–336.

Martin, D. W., Holloway, B. W., and Deretic, V. (1993) Characterization of a locus determining the mucoid status of Pseudomonas aeruginosa: algU shows sequence similarities with a Bacillus sigma factor. J. Bacteriol. 175:000–000.

Martin, D. W, M. J. Schurr, M. H. Mudd, J. R. W. Govan, B. W. Holloway. and V. Deretic. 1993A. Mechanism of conversion to mucoidy in *Pseudomonas seruginosa* infecting cystic fibrosis patients. Proc. Natl. Acad. Sci. USA 90:8377–8381.

Martin, D. W, M. J. Schurr, M. H. Mudd, and V. Deretic. 1993B. Differentiation of *Pseudomonas aeruginosa* into the alginate-producing form: inactivation of mucB causes conversion to mucoidy. Mol. Microbiol. 9:495–506.

May, T. B., Shinaberger, D., Maharaj, R., Kato, J., Chu, L., DeVault, J. D., Roychoudhury, S., Zieleinski, N. A., Berry, A., Rothmel, R. K., Misra, T. K., and Chakrabarty, A. M. (1991) Alginate synthesis by *Pseudomonas aeruginosa*: a key pathogenic factor in chronic pulmonary infections in cystic fibrosis. Clin. Microbiol. Rev. 4:191–206.

Meile, L., L. Soldati, and T. Leisinger. 1982. Regulation of proline catabolism in *Pseudomonas aeruginosa* PAO. Arch. Microbiol. 132:189–193.

Merrick, M. J. and J. R. Gibbins. 1985. The nucleotide sequence of the nitrogen-regulation gene ntrA of Klebsiella pneumoniae and comparison with conserved features in bacterail RNA polymerase sigma factors. Nucleic Acids Res. 13:7607–7620.

Miller, J. F., J. J. Mekalanos, and S. Falkow. 1989. Coordinate regulation and sensory transduction in the control of bacterial virulence. Science 243:916–922.

Mohr, C. D. and V. Deretic. 1990. Gene-Scrambling Mutagenesis: Generation and Analysis of Insertional Mutations in the Alginate Regulatory Region of *Pseudomonas aeruginosa*. J. Bacteriol. 172:6252–6260.

Mohr, C. D., J. H. J. Leveau, D. P. Krieg, N. S. Hibler, and V. Deretic. 1992. AlgR-binding sites within the algD promoter make up a set of inverted repeats separated by a large intervening segment of DNA. J. Bacteriol. 174:000–000.

Mohr, C. D. M., N. S. Hibler, and V. Deretic. 1991. AlgR, a response regulator controlling mucoidy in *Pseudomonas aeruginosa*, binds to the FUS sites of the algD promoter located unusually far upstream from the mRNA start site. J. Bacteriol. 173:5136–5143.

Mohr, C. D., Leveau, J. H. J., Krieg, D. P., Hibler, N. S., and Deretic, V. (1992) AlgR-binding sites within the algD promoter make up a set of inverted repeats separated by a large intervening segment of DNA. J. Bacteriol. 174:6624–6633.

Mohr, C. D. M., Hibler, N. S., and Deretic, V. (1991) AlgR, a response regulator controlling mucoidy in *Pseudomonas aeruginosa*, binds to the FUS sites of the algD promoter located unusually far upstream from the mRNA start site. J. Bacteriol. 173:5136–5143.

Mohr, C. D., D. W. Martin, W. M. Konyecsni, J. R. W. Govan, S. Lory, and V. Deretic. 1990. Role of the far-upstream sites of the algD promoter and the algR and rpoN genes in environmental modulation of mucoidy in *Pseudomonas aeruginosa*. J. Bacteriol. 172:6576–6580.

Mohr, C. D., Martin, D. W., Konyecsni, W. M., Govan, J. R. W., Lory, S., and Deretic, V. (1990) Role of the far-upstream sites of the algD promoter and the algR and rpoN genes in environmental modulation of mucoidy in *Pseudomonas aeruginosa*. J. Bacteriol. 172:6576–6580.

Mohr, C. D., and Deretic, V. (1992) In vitro interactions of the histone-like protein IHF with the algD promoter, a critical site for control of mucoidy in *Pseudomonas aeruginosa*. Biochem. Biophys. Res. Com. 189:837–844.

Ohman, D. E., J. B. Goldberg, and J. L. Flynn. 1990. Molecular analysis of the genetic switch activating alginate production. In: S. Silver, A. M. Chakrabarty, B. Iglewski, and S. Kaplan (eds.), Pseudomonas biotransformations, pathogenesis, and evolving biotechnology. American Society for Microbiology, Washington, D.C.

Ohman, D. E., Goldberg, J. B., and Flynn, J. L. (1990) Molecular analysis of the genetic switch activating alginate production. In: S. Silver, A. M. Chakrabarty, B. Iglewski, and S. Kaplan (eds.), Pseudomonas biotransformations, pathogenesis, and evolving biotechnology. American Society for Microbiology, Washington, D.C.

Ohnishi, K., Kutsukake, K., Suzuki, H., and Ino, T. (1992) A novel transcriptional regulation mechanism in the flagellar regulon of *Salmonella typhimurium*: an anti-sigma factor inhibits the activity of the flagellum-specific sigma factor, $\_^F$. Mol. Microbiol. 6:3149–3157.

Pearson, W. R., and D. J. Lipman. 1988. Improved tools for biological sequence comparison. Proc. Natl. Acad. Sci. USA 85:2444–2448.

Pedersen, S. S., Kharazmi, A., Espersen, F., and Hoiby, N. (1990) *Pseudomonas aeruginosa* alginate in cystic fibrosis sputum and the inflammatory response. Infect. Immun. 58:3363–3368.

Pier, G. B., Saunders, J. M., and Ames, P. (1987) Opsonophagocytic killing antibody to *Pseudomonas aeruginosa* mucoid exopolysaccharide in older, non-colonized cystic fibrosis patients. N. Engl. J. Med. 317:793–798.

Pier, G. B. (1992) Role of opsonic antibodies in defense against *Pseudomonas aeruginosa* in cystic fibrosis. Pediatric Pulm. S8:163–164.

Pier, G. B., Small, G. J., and Warren, H. B. (1990) Protection against mucoid *Pseudomonas aeruginosa* in rodent models of endobronchial infections. Science 249:537–540.

Predich, M., N. Gopal, and I. Smith. 1992. *Bacillus subtilis* early sporulation genes kinA, spo0F, and spo0A are transcribed by the RNA polymerase containing $\_^H$. J. Bacteriol. 174:2771–2778.

Pressler, T., Pandey, J. P., Espersen, F., Pedersen, S. S., Fomsgaard, A., Koch, C., and Hoiby, N. (1992) Immunoglobulin allotypes and IgG subclass antibody response to Pseudomonas aeruginosa antigens in chronically infected cystic fibrosis patients. Clin. Exp. Immunol. 90:209–214.

Rappuoli, R., B. Arico, and V. Scarlato. 1992. Thermoregulation and reversible differentiation in Bordetella: a model for pathogenic bacteria. Mol. Microbiol. 6:2209–2211.

Ratnaningsih, E., S. Dharmsthiti, V. Krishnapillai, A. Morgan, M. Sinclair, and B. W. Holloway. 1990. A combined physical and genetic map of *Pseudomonas aeruginosa* PAO. J. Gen. Microbiol. 136:2351–2357.

Sadoff, H. L. 1975. Encystment and germination in Azotobacter vinelandii. Bacteriol. Rev. 39:516–539.

Sadoff, H. L. (1975) Encystment and germination in Azotobacter vinelandii. Bacteriol. Rev. 39:516–539.

Schmidt, R., Margolis, P., Duncan, L., Coppolecchia, R., Moran, C. P., Jr., and Losick, R. (1990) Control of developmental transcription factor $\_^F$ by sporulation regulatory proteins SpoIIAA and SpoIIAB in *Bacillus subtilis*. Proc. Natl. Acad. Sci. USA 87:9221–9225.

Selvaraj, C., Fong, Y. C., and Iyer, V. N. (1984) A portable DNA sequence carrying the cohesive site (cos) of bacteriophage and the mob (mobilization) region of the broad-host-range plasmid RK2: a module for the construction of new cosmids. Gene 32:235–241.

Selvaraj, C., Y. C. Fong, and V. N. Iyer. A portable DNA sequence carrying the cohesive site (cos) of bacteriophage and the mob (mobilization) region of the broad-host-range plasmid RK2: a module for the construction of new cosmids. Gene 32:235–241.

Shortridge, V. D., M. L. Pato, A. I. Vasil, and M. L. Vasil. 1991. Physical mapping of virulence-associated genes in *Pseudomonas aeruginosa* by transverse alternating-field electrophoresis. Infect. Immun. 59:3596–3603.

Simon, R., V. Priefer, and A. Puhler. 1983. A broad host range mobilization system for in vivo genetic engeneering: transposon mutagenesis in gram negative bactera. Bio/Technology 1:784–791.

Stock, J. B., A. J. Ninfa, and A. M. Stock. 1989. Protein phosphorylation and the regulation of adaptive responses in bacteria. Microbiol. Rev. 53:450–490.

Stragier, P., Kunkel, B., Kroos, L., and Losick, R. (1989) Chromosomal rearrangements generating a composite gene for a developmental transcription factor. Science 243:507–512.

Tabor, S., and Richardson, C. C. (1985) A bacteriophage T7 RNA polymerase/promoter system for controlled expression of specific genes. Proc. Natl. Acad. Sci. USA 82:1074–1078.

Tabor, S., and C. C. Richardson. A bacteriophage T7 RNA polymerase/promoter system for controlled expression of specific genes. Proc. Natl. Acad. Sci. USA 82:1074–1078.

Tatti, K. M., H. L. Carter III, A. Moir, and C. P. Moran, Jr. 1989. Sigma H-directed transcription of citG in *Bacillus subtilis*. J. Bacteriol. 171:5928–5932.

Terry, J. M., Pina, S. E., and Mattingly, S. J. (1991) Environmental conditions which influence mucoid conversion in *Pseudomonas aeruginosa* PAO1. Infect. Immun. 59:471–477.

Tosi, M. F., Zakem, H., and Berger, M. (1990) Neutrophil elastase cleaves C3bi on opsonized Pseudomonas as well as CR1 on neutrophils to create a functionally important opsonin receptor mismatch. J. Clin. Invest. 86:300–308.

Totten, P. A., Lara, J. C., and Lory, S. (1990) The rpoN gene product of *Pseudomonas aeruginosa* is required for expression of diverse genes, including the flagellin gene. J. Bacteriol. 172:389–396.

Trempy, J. E., Morrison-Plummer, J., and Haldenwang, W. G. (1985) Synthesis of $\_^{29}$, and RNA polymerase specificity determinant, is a developmentally regulated event in *Bacillus subtilis*. J. Bacteriol. 161:340–346.

West, S. E., and Iglewski, B. H. (1988) Codon usage in *Pseudomonas aeruginosa*. Nucleic Acids Res. 16:9323–9335.

West, S. E., and B. H. Iglewski. 1988. Codon usage in *Pseudomonas aeruginosa*. Nucleic Acids Res. 16:9323–9335.

Woodruff, W. A., D. J. Hassett, and D. E. Ohman. 1992. Sequence analysis of *Pseudomonas aeruginosa* DNA containing the alginate gene algT revealed the adjacent gene nadB encoding aspartate oxidase. Abstracts of the General Meeting, New Orleans 1992, American Society for Microbiology, Washington D.C., p. 103.

Wozniak, D. J., and D. E. Ohman. 1991. *Pseudomonas aeruginosa* AlgB, a two-component response regulator of the NtrC family, is required for algD transcription. J. Bacteriol. 173:1406–1413.

Wozniak, D. J., and Ohman, D. E. (1991) *Pseudomonas aeruginosa* AlgB, a two-component response regulator of the NtrC family, is required for algD transcription. J. Bacteriol. 173:1406–1413.

Zielinski et al., 1992, "Alginate Synthesis in *Pseudomonas aeruginosa*: environmental regulation of the algC promoter", *J. Bacteriol.* 174(23):7680–7688.

We claim:

1. The mucA gene of FIG. 3 wherein the nucleotide "G" from position 440 is absent.

2. A purified DNA comprising a sequence of about 13 to 15 nucleotides complementary to a region spanning a deletion of nucleotide "G" from position 440 of the *Pseudomonas aeruginosa* mucA gene.

3. A purified DNA consisting essentially of about 13 to 15 nucleotides and comprising the sequence 5'-GAGCAGGGGCGCC-3' (SEQ ID NO:3).

4. A mucA gene having '-5'-CAGGGGGC-3' inserted between positions 433 and 434 of *Pseudomonas aeruginosa* mucA gene.

5. A purified DNA comprising a sequence of about 16–40 nucleotides complementary to a region spanning an insertion of 5'-CAGGGGGC-3' between positions 433 and 434 of the *Pseudomonas aeruginosa* mucA gene.

6. An oligonucleotide consisting essentially of about 16–40 nucleotides and comprising the sequence 5'-CAGGGGGCCAGGGGGC-3' (SEQ ID NO:4) of the *Pseudomonas aeruginosa* mucA gene.

7. The mucA gene of FIG. 3 wherein the nucleotide "C" from position 362 has been replaced with a "T" nucleotide.

8. A method of detecting conversion to mucoidy in *Pseudomonas aeruginosa* having an inactive mucA gene product comprising detecting an altered sequence in the mucA gene.

9. The method of claim 8 wherein the altered sequence encodes an inactive product.

10. The method of claim 8 wherein the altered sequence comprises at least one nucleotide change, insertion or deletion between positions 300 and 500 of the sequence of (SEQ ID NO:10).

11. The method of detecting conversion to mucoidy in *Pseudomonas aeruginosa* of claim 8, wherein the detecting comprises using a labeled nucleic acid.

12. The method of detecting conversion to mucoidy in *Pseudomonas aeruginosa* of claim 11, wherein the nucleic acid is labeled with a radioisotope, a detectable nucleotide analog, or a chemiluminescent moiety.

13. A purified DNA consisting essentially of a polynucleotide which codes for the amino acid sequence (SEQ ID NO:19).

14. A host cell transformed with an expression vector that comprises an insert consisting of a coding region for mucA (SEQ ID NO: 17), wherein the host cell is a bacteria, yeast, animal, or plant.

15. A host cell transformed with an expression vector that comprises an insert consisting of a coding region for mucB (SEQ ID NO: 18), wherein the host cell is a bacteria, yeast, animal, or plant.

16. A host cell transformed with an expression vector that comprises an insert consisting of a coding region for algU (SEQ ID NO: 19), wherein the host cell is a bacteria, yeast, animal, or plant.

17. A method for screening a candidate substance for preventing *P. aeruginosa* conversion to mucoidy comprising:

(a) obtaining an *E. coli* cell that expresses a reporter gene under the transcriptional control of the AlgD promoter;

(b) contacting the *E. coli* cell with a candidate substance; and (c) assaying for reporter gene activity, wherein a decrease in the expression of the reporter gene indicates inhibition of algD promoter activity.

18. A purified DNA having the MucA sequence of FIG. 2 wherein the MucA sequence contains a frameshift or nonsense mutation.

19. A purified DNA having the MucA sequence of FIG. 2 wherein the MucA sequence contains a frameshift mutation.

20. A purified DNA having the MucA sequence of FIG. 2 wherein the MucA sequence contains a frameshift mutation comprising an insertion or deletion of from 1 to about 10 nucleotides.

21. A purified DNA having the MucA sequence of FIG. 2 wherein the MucA sequence contains a frame shift or nonsense mutation and wherein the nucleotide "A" from position 371 is absent.

* * * * *

UNITED STATES PATENT AND TRADEMARK OFFICE
CERTIFICATE OF CORRECTION

PATENT NO. : 6,083,691
DATED : July 4, 2000
INVENTOR(S) : Deretic et al.

It is certified that error appears in the above-identified patent and that said Letters Patent is hereby corrected as shown below:

On the title page, item [63], Related U.S. Application Data, after "Pat. No. 5,591,838", please add -- Continuation-in-Part of application No. 08/260,202, June 15, 1994, Pat. No. 5,573,910. -- therefor.

In column 1, line 5, after "The present application is" please add -- a continuation-in-part of application No. 08/260,202, filed June 15, 1994, now Pat. No. 5,573,910, which is -- therefor.

Signed and Sealed this

Fifteenth Day of May, 2001

Attest:

NICHOLAS P. GODICI

Attesting Officer     Acting Director of the United States Patent and Trademark Office